US008637475B1

(12) United States Patent
Storer et al.

(10) Patent No.: US 8,637,475 B1
(45) Date of Patent: Jan. 28, 2014

(54) MODIFIED 2' AND 3' NUCLEOSIDE PRODRUGS FOR TREATING FLAVIVIRIDAE INFECTIONS

(75) Inventors: Richard Storer, Kent (GB); Gilles Gosselin, Monpellier (FR); Jean-Pierre Sommadossi, Cambridge, MA (US)

(73) Assignees: Idenix Pharmaceuticals, Inc., Cambridge, MA (US); University of Cagliari, Cagliari (IT); The Centre National de la Recherché Scientifique, Paris (FR); L'Universite Montpelier II, Montpelier (FR)

( * ) Notice: Subject to any disclaimer, the term of this patent is extended or adjusted under 35 U.S.C. 154(b) by 0 days.

(21) Appl. No.: 13/168,895

(22) Filed: Jun. 24, 2011

Related U.S. Application Data

(60) Continuation of application No. 12/131,868, filed on Jun. 2, 2008, which is a division of application No. 10/608,907, filed on Jun. 27, 2003, now Pat. No. 7,608,600.

(60) Provisional application No. 60/392,350, filed on Jun. 28, 2002, provisional application No. 60/466,194, filed on Apr. 28, 2003, provisional application No. 60/470,949, filed on May 14, 2003.

(51) Int. Cl.
*A61K 31/70* (2006.01)
*C07H 19/00* (2006.01)

(52) U.S. Cl.
USPC ............... 514/43; 514/42; 514/45; 514/49; 536/27.1; 536/28.1; 536/28.6

(58) Field of Classification Search
None
See application file for complete search history.

(56) References Cited

U.S. PATENT DOCUMENTS

| | | | |
|---|---|---|---|
| 5,118,672 | A | 6/1992 | Schinazi et al. |
| 5,149,794 | A | 9/1992 | Yatvin et al. |
| 5,455,339 | A | 10/1995 | Chu et al. |
| 6,071,922 | A | 6/2000 | Schinazi et al. |
| 6,348,587 | B1 | 2/2002 | Schinazi et al. |
| 6,784,161 | B2 * | 8/2004 | Ismaili et al. .................. 514/43 |
| 7,429,572 | B2 | 9/2008 | Clark |
| 7,601,820 | B2 | 10/2009 | Wang et al. |
| 7,608,600 | B2 | 10/2009 | Storer et al. |
| 2002/0120129 | A1 | 8/2002 | Beigelman et al. |
| 2005/0009737 | A1 | 1/2005 | Clark |

FOREIGN PATENT DOCUMENTS

| | | |
|---|---|---|
| GB | 1209654 | 10/1970 |
| WO | WO 97/12033 | 4/1997 |
| WO | WO 99/43691 | 9/1999 |
| WO | WO01/06315 | * 8/2001 |
| WO | WO 01/79246 | 10/2001 |
| WO | WO 01/90121 | 11/2001 |
| WO | WO 01/92282 | 12/2001 |
| WO | WO 01/96353 | 12/2001 |
| WO | WO 02/18369 | 3/2002 |
| WO | WO 02/18404 | 3/2002 |

OTHER PUBLICATIONS

Rong et al., Tetrahedron, vol. 50 (16), Apr. 1994, abstract.*
Camaras et al., Journal of Medicinal Chemistry, 1992, vol. 35, pp. 2721-2727.*
Samano et al., Journal of American Chemical Society, 1992, vol. 114, pp. 4007-4008.*
D'Clercq, Erick, "Antiviral drugs: current state of the art," Journal of Clinical Virology, 22:73-89 (2001).
Raifeld et al., "Synthesis of 3-Substituted (Azido, Acylthio, Chloro or Fluoro)-2,3-dideoxy-D-erythro-pentoses and 3-Methyl-3-substituted-2,3-dideoxy-D-erythro-pentoses," Tetrahedron, 50(29):8603-8616 (1994).
Shutalev et al., "Sythesis and Crystal Structure of 3'-Fluoro-3'-Methyl-2',2'-Dideoxythymidine. Inhibitory Properties of 3'-Fluoro-3'-Methyl-2',3'-Dideoxythymidine-5'-Triphosphate in the Synthesis of DNA in Cell-Free Media," Bioorganic & Medicinal Chemistry Letters, 4(5):761-768 (1994).
Sorrell, Thomas N., Organic Chemistry, pp. 156-158 and 1431, Sausalito, CA (1997).
U.S. Appl. No. 60/392,350, filed Jun. 28, 2002, Sommadossi.
U.S. Appl. No. 60/466,194, filed Apr. 28, 2003, Sommadossi.
U.S. Appl. No. 60/470,949, filed May 14, 2003, Sommadossi.
U.S. Appl. No. 60/474,368, filed May 30, 2003, Clark.
U.S. Appl. No. 10/608,907, filed Jun. 27, 2003, Sommadossi.
U.S. Appl. No. 11/854,218, filed Sep. 12, 2007, Clark.
U.S. Appl. No. 12/131,868, filed Jun. 2, 2008, Sommadossi.
U.S. Appl. No. 12/878,262, filed Sep. 9, 2010, Clark.
Interference 105,871, Notice to Declare Interference dated Feb. 22, 2012.
Interference 105,871, Sommadossi Clean Claims dated Mar. 7, 2012.
Interference 105,871, Sommadossi Notice of Real Parties in Interest dated Mar. 7, 2012.
Interference 105,871, Sommadossi Notice of Related Proceedings dated Mar. 7, 2012.
Interference 105,871, Sommadossi File Copy Request dated Mar. 7, 2012.
Interference 105,871, Clark Real Party-In-Interest dated Mar. 7, 2012.
Interference 105,871, Clark Clean Claims dated Mar. 7, 2012.

(Continued)

*Primary Examiner* — Traviss C McIntosh, III
(74) *Attorney, Agent, or Firm* — Jones Day

(57) ABSTRACT

2' and/or 3' prodrugs of 1', 2', 3' or 4'-branchednucleosides, and their pharmaceutically acceptable salts and derivatives are described. These prodrugs are useful in the prevention and treatment of Flaviviridae infections, including HCV infection, and other related conditions. Compounds and compositions of the prodrugs of the present invention are described. Methods and uses are also provided that include the administration of an effective amount of the prodrugs of the present invention, or their pharmaceutically acceptable salts or derivatives. These drugs may optionally be administered in combination or alteration with further anti-viral agents to prevent or treat Flaviviridae infections and other related conditions.

11 Claims, 4 Drawing Sheets

(56) References Cited

OTHER PUBLICATIONS

Interference 105,871, Clark Request for File Copies dated Mar. 7, 2012.
Interference 105,871, Clark Notice of Related Proceedings dated Mar. 7, 2012.
Interference 105,871, Sommadossi Motions List dated Apr. 11, 2012.
Interference 105,871, Clark List of Intended Motions dated Apr. 11, 2012.
Interference 105,871, Order Authorizing Motions dated Apr. 24, 2012.
Interference 105,871, Order Large Exhibits dated May 17, 2012.
Interference 105,871, Clark Notice dated May 31, 2012.
Interference 105,871, Sommadossi Priority Statement dated Jun. 5, 2012.
Interference 105,871, Sommadossi Substantive Motion 1 dated Jun. 5, 2012.
Interference 105,871, Sommadossi Motion 5 dated Jun. 5, 2012.
Interference 105,871, Sommadossi Exhibit List dated Jun. 5, 2012.
Interference 105,871, Clark Notice Regarding Filing Priority Statement dated Jun. 5, 2012.
Interference 105,871, Clark Priority Statement dated Jun. 5, 2012.
Interference 105,871, Clark Substantive Motion 1 dated Jun. 5, 2012.
Interference 105,871, Clark Substantive Motion 2 dated Jun. 5, 2012.
Interference 105,871, Clark Substantive Motion 3 dated Jun. 5, 2012.
Interference 105,871, Clark Substantive Motion 6 dated Jun. 5, 2012.
Interference 105,871, Order Authorizing Responsive Motion dated Jun. 18, 2012.
Interference 105,871, Notice Regarding Sommadossi Substantive Motion 5 dated Jun. 22, 2012.
Interference 105,871, Sommadossi Substantive Motion 18 dated Jun. 22, 2012.
Interference 105,871, Sommadossi Exhibit 1101 dated Jun. 28, 2012.
Interference 105,871, Sommadossi Exhibit 1136 dated Jun. 28, 2012.
Interference 105,871, Sommadossi Exhibit 1013 dated Jun. 28, 2012.
Interference 105,871, Sommadossi Exhibit 1088 dated Jun. 28, 2012.
Interference 105,871, Clark Submission of Sommadossi Declarations dated Jun. 28, 2012.
Interference 105,871, Sommadossi Submission of Clark Declarations dated Jun. 28, 2012.
Interference 105,871, Order Cross Examination of Witnesses dated Jul. 5, 2012.
Interference 105,871, Clark Notice of Change in Related Proceedings dated Jul. 6, 2012.
Interference 105,871, Order Authorizing Miscellaneous Motion dated Jul. 16, 2012.
Interference 105,871, Sommadossi Miscellaneous Motion 19 dated Jul. 18, 2012.
Interference 105,871, Clark Opposition 19 dated Jul. 25, 2012.
Interference 105,871, Sommadossi Reply 19 dated Jul. 30, 2012.
Interference 105,871, Clark Notice 2 dated Aug. 14, 2012.
Interference 105,871, Order Regarding Miscellaneous Motion and Notion Numbering dated Aug. 16, 2012.
Interference 105,871, Sommadossi Opposition 1 dated Aug. 17, 2012.
Interference 105,871, Sommadossi Opposition 2 dated Aug. 17, 2012.
Interference 105,871, Sommadossi Opposition 3 dated Aug. 17, 2012.
Interference 105,871, Sommadossi Opposition 6 dated Aug. 17, 2012.
Interference 105,871, Clark Opposition 1 dated Aug. 17, 2012.
Interference 105,871, Clark Opposition 6 dated Aug. 17, 2012.
Interference 105,871, Order Cross Examination of Marquez dated Sep. 27, 2012.
Interference 105,871, Sommadossi Reply 1 dated Oct. 11, 2012.
Interference 105,871, Sommadossi Reply 6 dated Oct. 11, 2012.
Interference 105,871, Clark Reply 1 dated Oct. 11, 2012.
Interference 105,871, Clark Reply 2 dated Oct. 11, 2012.
Interference 105,871, Clark Reply 3 dated Oct. 11, 2012.
Interference 105,871, Clark Reply 6 dated Oct. 11, 2012.
Interference 105,871, Clark Corrected Reply 1 dated Oct. 11, 2012.
Interference 105,871, Clark Corrected Reply 6 dated Oct. 11, 2012.
Interference 105,871, Clark Submission of Corrected Replies 1 and 6 dated Oct. 11, 2012.
Interference 105,871, Sommadossi Responses to Material Facts of Clark Corrected Reply 1 dated Oct. 18, 2012.
Interference 105,871, Sommadossi Responses to Material Facts of Clark Reply 2 dated Oct. 18, 2012.
Interference 105,871, Sommadossi Responses to Material Facts of Clark Reply 3 dated Oct. 18, 2012.
Interference 105,871, Sommadossi Responses to Material Facts of Clark Corrected Reply 6 dated Oct. 18, 2012.
Interference 105,871, Sommadossi Miscellaneous Motion 8 dated Oct. 23, 2012.
Interference 105,871, Sommadossi Request for Oral Argument dated Oct. 23, 2012.
Interference 105,871, Clark Miscellaneous Motion 7 dated Oct. 23, 2012.
Interference 105,871, Clark Request for Oral Arguments dated Oct. 23, 2012.
Interference 105,871, Sommadossi Opposition 7 dated Nov. 13, 2012.
Interference 105,871, Clark Opposition 8 dated Nov. 13, 2012.
Interference 105,871, Order Denying Requests for Oral Argument dated Nov. 16, 2012.
Interference 105,871, Sommadossi Reply 8 dated Nov. 19, 2012.
Interference 105,871, Clark Reply 7 dated Nov. 19, 2012.
Interference 105,871, Sommadossi Filing of the Record dated Nov. 28, 2012.
Interference 105,871, Clark Final Exhibit List dated Nov. 28, 2012.
Interference 105,871, Clark Submission of Record dated Nov. 28, 2012.
Curriculum Vitae of Jeffrey S. Glenn, M.D., Ph.D.
Declaration of Jeffrey S. Glenn, M.D., Ph.D., signed Jun. 2, 2012.
Curriculum Vitae of Masad José Damha, Ph.D., F.C.I.C.
Curriculum Vitae of Stanley M. Lemon, M.D.
Declaration of Stanley M. Lemon, M.D., signed Jun. 4, 2012.
Declaration of Masad J. Damha, Ph.D., signed Jun. 2, 2012.
Transcript of Deposition of Christoph Seeger, Ph.D., taken Sep. 28, 2012.
Transcript of Deposition of Victor E. Marquez, Ph.D., taken Sep. 26, 2012.
Curriculum Vitae of Barry M. Trost, Ph.D.
Declaration of Barry M. Trost, Ph.D., signed Jun. 20, 2012.
2nd Declaration of Christoph Seeger, Ph.D.
2nd Declaration of Victor E. Marquez, Ph.D.
Transcript of Deposition of Victor E. Marquez, Ph.D., taken Jul. 27, 2012.
Transcript of Deposition of Christoph Seeger, Ph.D., taken Jul. 25, 2012.
Feb. 9, 2011 Material Transfer Agreement.
Dec. 1, 2010 Mutual Non-Disclosure Agreement.
Dec. 15, 2005 Consulting Agreement.
Declaration and Curriculum Vitae of Jean-Pierre Sommadossi, Ph.D., Interference No. 103,906, Apr. 3, 1998.
Substitute Declaration of Victor E. Marquez, Ph.D.
Victor E. Marquez, Ph.D. curriculum vitae.
Substitute Declaration of Christoph Seeger, Ph.D.
Christoph Seeger, Ph.D. curriculum vitae.
E-mail from Anthony M. Zupcic to Thomas E. Friebel on Oct. 10, 2012.
U.S. Appl. No. 60/474,368 Provisional Appln. Cover Sheet dated May 30, 2003.
U.S. Appl. No. 60/474,368, Petition to Correct Inventorship dated Jul. 11, 2005.
U.S. Appl. No. 10/608,907 Declaration and Power of Attorney filed Jan. 12, 2004.
U.S. Appl. No. 10/608,907 Amendment filed May 25, 2006.
U.S. Appl. No. 10/608,907 Amendment filed Feb. 15, 2007.
U.S. Appl. No. 10/608,907 Amendment filed Aug. 20, 2007.
U.S. Appl. No. 10/608,907 Supplemental Amendment filed Oct. 30, 2007.

(56) References Cited

OTHER PUBLICATIONS

U.S. Appl. No. 10/608, 907 Amendment filed Jul. 24, 2008.
U.S. Appl. No. 10/608,907 Amendment filed Jan. 20, 2009.
U.S. Appl. No. 10/608,907 Notice of Allowance dated Apr. 7, 2009.
U.S. Appl. No. 12/131,868 filed Jun. 2, 2008.
U.S. Appl. No. 12/131,868 Declaration and Power of Attorney filed Jun. 2, 2008.
U.S. Appl. No. 12/131,868 Preliminary Amendment filed Jun. 2, 2008.
U.S. Appl. No. 12/131,868 Response to Notice to File Corrected Application Papers dated Sep. 17, 2008.
U.S. Appl. No. 12/131,868 Response to Restriction Requirement dated Dec. 14, 2010.
U.S. Appl. No. 12/131,868 Office Action dated Mar. 3, 2011.
U.S. Appl. No. 12/131,868 Amendment dated May 27, 2011.
U.S. Appl. No. 12/131,868 Office Action dated Aug. 16, 2011.
U.S. Appl. No. 12/131,868 Amendment dated Sep. 20, 2011.
U.S. Appl. No. 12/131,868 Amendment dated Jun. 21, 2012.
U.S. Appl. No. 12/131,868 Substitute Specification (marked up version).
U.S. Appl. No. 12/131,868 Substitute Specification (clean version).
U.S. Appl. No. 12/150,327 Amendment dated Nov. 16, 2010.
U.S. Appl. No. 11/005,469 Amendment dated Apr. 5, 2007.
U.S. Appl. No. 11/005,469 Amendment dated Dec. 14, 2007.
U.S. Appl. No. 11/005,444 Amendment dated Apr. 6, 2009.
U.S. Appl. No. 11/005,444 Amendment dated Apr. 4, 2008.
U.S. Appl. No. 11/005,446 Amendment dated May 7, 2007.
U.S. Appl. No. 11/854,218 Amendment dated Jun. 20, 2011.
U.S. Appl. No. 11/854,218 Office Action dated Dec. 23, 2010.
U.S. Appl. No. 11/854,218 Amendment dated Oct. 11, 2010.
U.S. Appl. No. 11/854,218 Office Action dated Jul. 22, 2010.
U.S Appl. No. 11/854,218 Preliminary Amendment dated Sep. 12, 2007.
U.S. Appl. No. 12/878,262 Office Action dated Jun. 8, 2011.
U.S. Appl. No. 12/878,262 Preliminary Amendment dated Sep. 9, 2010.
U.S. Patent No. 7,429,572 Restriction Requirement dated Sep. 5, 2006.
U.S. Appl. No. 60/392,350 Provisional Application filed Jun. 28, 2002.
U.S. Appl. No. 60/392,350 Corrected Filing Receipt dated Jan. 17, 2008.
European Patent Appln. No. 03761744 Office Action dated Apr. 16, 2012.
Apath.com webpage at http://www.apath.com/Blazing_Blight_7.htm.
Awad, Laila Fathy, et al., A Synthesis of Methyl 3-O-(β-D-Mannopyranosyl)-α-Dmannopyranoside from Sulfonate Intermediates, Bull. Chem. Soc. Jpn., vol. 59, pp. 1587-1592 (1986).
Awano et al., Arch. Pharm., 329: 66-72 (1996).
Bartenschlager and Lohmann, Antiviral Res. 52: 1-17 (2001).
Beard et al., Hepatology 30: 316-24 (1999).
Beauchamp, L.M., et al , Amino Acid Ester Prodrugs of Acyclovir, Antiviral Chemistry & Chemotherapy, vol. 3, No. 3, pp. 157-164 (1992).
Behrens et al., EMBO J. 15: 12-22 (1996).
Blight et al., Science 290: 1972-74 (2000).
Bourne, Nigel, et al., Screening for Hepatitis C Virus Antiviral SctivityWith A Cell-based Secreted Alkaline Phosphatase Reporter Replicon System, Antiviral Research, vol. 67, pp. 76-82 (2005).
Briot, Anne, et al., Benzylsulfonyl: A Valuable Protecting and Deactivating Group in Phenol Chemistry, Tetrahedron Letters, vol. 44, pp. 965-967 (2003).
*Calif. Inst. of Technol.* v. *Enzo Life Sciences, Inc.*, Interference 105,496, Paper 120 (BPAI Sep. 22, 2010).
Carroll and LaFemina, Antiviral Research: Strategies in Antiviral Drug Discovery 153-166 (Robert L. LaFemina, Ph.D., ed., 2009).

Choi, Yongseok, et al., A Conformationally Locked Analogue of the Anti-HIV Agent Stavudine. An Important Correlation between Pseudorotation and Maximum Amplitude, J. Med. Chem., vol. 46, pp. 3292-3299 (2003).
Chu et al., FEMS Microbiology Letters 202: 9-15 (2001).
Clark, J.L. et al., Design, Synthesis, and Antiviral Activity of 2'-Deoxy-2'-fluoro-2'-C-methylcytidine, a Potent Inhibitor of Hepatitis C Virus Replication, J. Med. Chem., vol. 48, pp. 5504-5508 (2005).
Clark, Jeremy L., et al., Synthesis of 2-Deoxy-2-Fluoro-2-C-Methyl-DRibofuranoses, Journal of Carbohydrate Chemistry, vol. 25, pp. 461-470 (2006).
Clark, Jeremy L., et al., Synthesis and antiviral activity of 2'-deoxy-2'-fluoro-2'-Cmethyl purine nucleosides as inhibitors of hepatitis C virus RNA replication, Bioorganic & Medicinal Chemistry Letters, vol. 16, pp. 1712-1715 (2006).
Clarke, Baillière's Clin. Gastroenterol. 14: 293-305 (2000).
Cohen, Science 285: 26-30 (1999).
Commentary, Science 285: 9 (1999).
Condit, R.C., Principles of Virology (Chapter 2), in Knipe, D.M. et al., eds., Fields Virology, Fourth Edition, Philadelphia, Lippincott Williams & Wilkins (2001).
Condit, R.C., Principles of Virology (Chapter 2), in Knipe, D.M. et al., eds., Fields Virology, Fifth Edition, Philadelphia, Lippincott Williams & Wilkins (2007).
Cox et al., Principles of Biochemistry, p. 330 (1993).
Cramer and Pfleiderer, Helvetica Chimica Acta 79: 2114-2136 (1996).
Damha et al., Curr. Protocols in Nucleic Acid Chem.: 1.7.1-1.7.19 (2002).
Damha et al., Nucleosides, Nucleotides & Nucleic Acids 22: 1343-1346 (2003).
Damha et al., J. Org. Chem., 71(3): 921-925 (2006).
Désiréand Prandi, Carbohydrate Research 317: 110-118 (1999).
Dhanak, D., et al., Identification and Biological Characterization of Heterocyclic Inhibitors of the Hepatitis C Virus RNA-dependent RNA Polymerase, J. Biol. Chem. vol. 277, No. 41, pp. 38322-38327 (2002).
Diamond et al., J. Virol. 74: 4957-66 (2000).
Di Bisceglie and Bacon, Sci. Am. 281: 80-85 (1999).
Di Bisceglie, Hepatology 35: 224-31 (2002).
Eldrup et al., "Structure-Activity Relationship of Heterobase-Modified 2'-C-Methyl Ribonucleosides as Inhibitors of Hepatitis C Virus RNA Replication," J. Med. Chem., 47:5284-5297 (2004).
Ferrari et al., J. Virol. 73: 1649-54 (1999).
Fournier-Caruana et al., Biologicals 28: 33-40 (2000).
Frese et al., J. Gen. Virol. 82: 723-33 (2001).
Frese et al., Hepatology 35: 694-703 (2002).
Friebe et al., J. Virol. 75: 12047-57 (2001).
Furman et al., Antiviral Res. 91: 120-132 (2011).
GenBank accession No. AJ242652 at http://www.ncbi.nlm.nih.gov/nuccore/5441834?sat=8&satkey=803423.
*Genentech, Inc.* v. *Chiron Corp.*, Interference 105,048, Paper 258 (BPAI Nov. 30, 2004) (non-precedential).
*Goeddel* v. *Sugano* Interference 105,334, Paper 109, at 40-42 (BPAI Sep. 29, 2008), rev'd on other grounds, 617 F.3d 1350 (Fed. Cir. 2010).
Goldman, Bruce, Potential New Class of Drugs to Combat Hepatitis C Identified by Scientists, Stanford School of Medicine, http://med.stanford.edu/ism/2010/january/glenn.html (Jan. 20, 2010).
Grakoui et al., Hepatology 33: 489-95 (2001).
Greene and Wuts, Protective Groups in Organic Synthesis (3rd ed.): 76-81, 95-96, 102-106, 150, 173-176 and 197-198 (1999).
Guo, J.-T., Bichko, V.V., Seeger, C., Effect of Alpha Interferon on the Hepatitis C Virus Replicon, J. Virol., vol. 75, pp. 8516-8523 (2001).
Harrison, Steadman D., et al., Therapeutic Synergism of Tiazofurin and Selected Antitumor Drugs against Sensitive and Resistant P388 Leukemia in Mice, Cancer Research, vol. 46, pp. 3396-3400 (1986).
Harry-O'kuru, Rogers E., et al., A Short, Flexible Route toward 2'-C-Branched Ribonucleosides, J. Org. Chem., vol. 62, pp. 1754-1759 (1997).
Hirooka et al., Bull. Chem. Soc. Jpn. 74(9): 1679-1694 (2001).
Hong et al., Virology 256: 36-44 (1999).

(56) References Cited

OTHER PUBLICATIONS

Hostetler, Karl Y., et al., Synthesis and Antiretroviral Activity of Phospholipid Analogs of Azidothymidine and Other Antiviral Nucleosides, The Journal of Biological Chemistry, vol. 265, No. 11, pp. 6112-6117 (1990).
*Hudziak v. Ring*, Interference 105,266, 2005 WL 3694322 (BPAI 2005).
Husson van Vilet, Biologicals 18: 25-27 (1990).
Ikeda et al., J. Virol. 76: 2997-3006 (2002 (received Oct. 3, 2001, accepted for publication Dec. 20, 2001).
Ishii et al., Hepatology 29: 1227-35 (1999).
Jeong, Lak S. et al., Unanticipated Retention of Configuration in the DAST Fluorination of Deoxy-4'-thiopyrimidine Nucleosides with "Up" Hydroxyl Groups, Tetrahedron Letters, vol. 35, No. 41, pp. 7569-7572 (1994).
Jordan et al., J. Infect. Dis. 182: 1214-17 (2000).
Julander et al., Antiviral Res. 86: 261-7 (2010).
Kim et al., Biochem. Biophys. Res. Commun. 290: 105-12 (2002).
Kolykhalov et al., Science 277: 570-74 (1997).
Krieger et al., J. Virol. 75: 4614-24 (2001).
Kuroboshi et al., Synlett 987-988 (1995).
Lal, G. Sankar, et al., Electrophilic NF Fluorinating Agents, Chem. Rev., vol. 96, pp. 1737-1755 (1996).
Lalezari, J., et al., Potent Antiviral Activity of the HCV Nucleoside Polymerase Inhibitor R7128 with PEG-IFN and Ribavirin: Interim Results of R7128 500mg BID for 28 Days, J. Hepatology, vol. 48, Supplement 2, p. S29 (2008).
Lalezari, J., et al., Potent Antiviral Activity of the HCV Nucleoside Polymerase Inhibitor, R7128, in Combination with PEG-IFN α-2a and Ribavirin, 43rd Annual Meeting of EASL, Milan, Italy, Apr. 23-27, 2008.
Lam et al., Antimicrob. Agents Chemother. 55: 2566-2575 (2011).
Lam et al., Antimicrob. Agents Chemother. 54: 3187-3196 (2010).
Lanford and Bigger, Virology 293: 1-9 (2002).
Lawitz et al., Abstract 7, J. Hepatol. 56: S4 (2012).
Lawitz et al., Abstract 102, Global Antiviral J. 5: 96.
Lesburg et al., Curr. Opin. Investig. Drugs 1: 289-96 (2000).
Leyssen et al., Clin. Microbiol. Rev. 13: 67-82 (2000).
Limbach, Patrick A., et al., Summary: The Modified Nucleosides of RNA, Nucleic Acids Research, vol. 22, No. 12, pp. 2183-2196 (1994).
Lindenbach, B.D. and Rice, C.M., Flaviviridae: The Viruses and Their Replication (Chapter 32) in Knipe, D.M. et al., eds., Fields Virology, 4th ed. Philadelphia, Lippincott Williams & Wilkins (2001).
Lohmann et al., J. Virol. 71: 8416-28 (1997).
Lohmann et al., Virology 249: 108-18 (1998).
Lohmann, V., et al., Replication of Subgenomic Hepatitis C Virus RNAs in a Hepatoma Cell Line, Science, vol. 285, pp. 110-113 (1999).
Lohmann et al. 1999, J. Biol. Chem. 274: 10807-15.
Lohmann et al., J. Virol. 75: 1437-49 (2001).
Markland et al., Antimicrob. Agents Chemother. 44: 859-66 (2000).
Marshall, Science 290: 1870-71 (2000).
Matsuda et al., Chem. Pharm. Bull. 36(3): 945-953 and 3967-3970 (1988).
McGuigan et al, Antiviral Chem. & Chemother. 12: 293-300 (2001).
McGuigan et al., Antiviral Chem. Chemother. 5: 271-277 (1994).
McKenzie, Robin, M.D., et al., Hepatic Failure and Lactic Acidosis Due to Fialuridine (FIAU), an Investigational Nucleoside Analogue for Chronic Hepatitis B, The New England Journal of Medicine, vol. 333, No. 17, pp. 1099-1105 (1995).
McManus, Appl. Environ. Microbiol. 31: 35-38 (1976).
The Merck Index, 2001, 13th ed., 4401.
W.J. Middleton, J. Org. Chem. 40(5): 574-578 (1975).
Milne, H. Bayard and Peng, Chi-Hsieh, The Use of Benzylsulfonyl Chloride in Peptide Syntheses, J. Am. Chem. Soc., vol. 79, pp. 639-644 (1956).

Moradpour et al., J. Biol. Chem. 277: 593-601 (2002).
Mottola et al., Virology 293: 31-43 (2002).
Murakami et al., J. Biol. Chem. 285: 34337-34347 (2010).
Ness and Fletcher, J. Org. Chem. 22: 1470-1473 (1957).
News & Analysis, Nature Reviews 10: 891 (2011).
Oh et al., J. Virol. 73: 7694-702 (1999).
Oxtoby, David W., et al., Principles of Modern Chemistry, Fourth Edition, pp. A.41-A.49 (1999).
Pietschmann et al., J. Virol. 75: 1252-64 (2001).
Prusoff, Cancer Res. 23: 1246-59 (1963).
Randall and Rice, Curr. Opin. Infect. Dis. 14: 743-47 (2001).
Rosenberg, J. Mol. Biol. 313: 451-64 (2001).
Schmit, Synlett 238-240 (1994).
Shi and Lai, Cell. Mol. Life Sci. 58: 1276-95 (2001).
Shim, J. et al., Canonical 3'-deoxyribonucleotides as a chain terminator for HCV NS5B RNA-dependent RNA polymerase, Antiviral Research, vol. 58, pp. 243-251 (2003).
Shimakami et al., Proc. Nat'l. Acad. Sci U.S.A. 109:941-6 (2012).
Singh, Rajendra P. and Shreeve, Jean'ne M., Recent Advances in Nucleophilic Fluorination Reactions of Organic Compounds Using Deoxofluor and DAST, Synthesis, No. 17, pp. 2561-2678 (2002).
Sofia, Michael J., et al., Nucleoside, Nucleotide, and Non-Nucleoside Inhibitors of Hepatitis C Virus NS5B RNA-Dependent RNA-Polymerase, J. Med. Chem., vol. 55, pp. 2481-2531 (2012).
Sofia et al., J. Med. Chem. 53: 7202-7218 (2010).
Sofia et al., Abstracts of Papers, 238th ACS National Meeting, Washington, DC, United States, Aug. 16-20, 2009, MEDI-101.
Song, Xueqin, et al , Amino Acid Ester Prodrugs of the Anticancer Agent Gemcitabine: Synthesis, Bioconversion, Metabolic Bioevasion, and hPEPT1-Mediated Transport, Molecular Pharmaceutics, vol. 2, No. 2, pp. 157-167 (2004).
Sowa et al., Bulletin of the Chemical Society of Japan 48(7): 2084-2090 (1975).
Stuyver, L.J., et al., Ribonucleoside Analogue That Blocks Replication of Bovine Viral Diarrhea and Hepatitis C Viruses in Culture, Antimicrobial Agents and Chemotherapy, vol. 47, No. 1, pp. 244-254 (2003).
Stuyver, L.J., et al , Inhibition of the Subgenomic Hepatitis C Virus Replicon in Huh-7 Cells by 2'-deoxy-2'-fluorocytidine, Antimicrobial Agents and Chemotherapy, vol. 48, No. 2, pp. 651-654 (2004).
Stuyver, L.J. et al , Inhibition of Hepatitis C Replicon RNA Synthesis by β-D-2'- Deoxy-2'-fluoro-2'-C-methylcytidine: A Specific Inhibitor of Hepatitis C Virus Replication, Antimicrobial Agents & Chemotherapy, vol. 17, pp. 79-87 (2006).
Taguchi et al., J. of the American Chemical Society 96: 3010-3011 (1974).
Taktakishvili and Nair, Tetrahedron Letters 41: 7173-7176 (2000).
The Journal of the American Chemical Society, Table of Contents, vol. 79, No. 3 (1957).
Tisdale et al., Antivir. Chem. Chemother., 4(5): 281-7 (1993).
Trost, Barry M. and Kallander, Lara S., A Versatile Enantioselective Strategy Toward L-C-Nucleosides: A Total Synthesis of L-Showdomycin, J. Org. Chem., vol. 64, No. 15, pp. 5427-5435 (1999).
Trost, Barry M., et al., Asymmetric Synthesis of Oxygen Heterocycles via Pd-Catalyzed Dynamic Kinetic Asymmetric Transformations: Application to Nucleosides, Chem Eur. J., vol. 9, pp. 4442-4451 (2003).
van Boom et al., Tetrahedron Letters 27: 1211-1214 (1986).
*Visser v. Hofvander*, Interference 103,579, Final Decision (BPAI).
Vithanomsat et al., Southeast Asian J. Trop. Med. Public Health 15: 27-31 (1984).
Vorbrüggen and Ruh-Pohlenz, Handbook of Nucleoside Synthesis (John Wiley & Sons., Inc., New York), pp. 140-141 and 403 (2001).
Wachtmeister et al., Tetrahedron 55: 10761-10770 (1999).
Wakita, T., et al., Production of infectious hepatitis C virus in tissue culture from a cloned viral genome, Nature Medicine, vol. 11, pp. 791-796 (2005).
Walton, E., et al., Branched-Chain Sugar Nucleosides. A New Type of Biologically Active Nucleoside, Journal of the American Chemical Society, vol. 88, No. 19, pp. 4524-4525 (1966).

(56) References Cited

OTHER PUBLICATIONS

Wang, Peiyuan, et al., An Efficient and Diastereoselective Synthesis of PSI-6130: A Clinically Efficacious Inhibitor of HCV NS5B Polymerase, J. Org. Chem., vol. 74, No. 17, pp. 6819-6824 (2009).
Watts and Damha, Can. J. Chem., 86: 641-656 (2008).
Wilds and Damha, Nucleic Acids Res. 28(18): 3625-3635 (2000).
Wohlrab et al., Biochim. Biophys. Acta, 824: 233-42 (1985).
Wolfe et al., "A Concise Synthesis of 2'-C-Methylribonucleosides," Tetrahedron Letters, 36(42):7611-7614 (1995).
Wu, Hepatology 33: 1550-51 (2001).
Yamashita et al., J. Biol. Chem. 273: 15479-86 (1998).
Yanagi et al., Proc. Natl. Acad. Sci. USA 94: 8738-43 (1997).
Yanagi et al., Virology 244: 161-72 (1998).
Yang, Shu Shu, et al., Synthesis of DL-1-deoxy-fluoro-6-O-methyl-chiro-inositol: confirmation of a structural-DAST fluorination correlation, Carbohydrate Research, vol. 249, pp. 259-263 (1993).
Yi et al., Proc. Nat'l Acad. Sci. U.S.A. 103:2310-5 (2006).
Yi, MinKyung, et al., Subgenomic Hepatitis C Virus Replicons Inducing Expression of a Secreted Enzymatic Reporter Protein, Virology, vol. 304, pp. 197-210 (2002).
Yoo et al., J. Virol. 69: 32-38 (1995).
Zuck, Paul, et al., A Cell-based β-lactamase Reporter Gene Assay for the Identification of Inhibitors of Hepatitis C Virus Replication, Analytical Biochemistry, vol. 344, pp. 344-355 (2004).

* cited by examiner

Figure 1: Chemical Structures of Illustrative Nucleosides

US 8,637,475 B1

MODIFIED 2' AND 3' NUCLEOSIDE PRODRUGS FOR TREATING FLAVIVIRIDAE INFECTIONS

CROSS-REFERENCE TO RELATED APPLICATIONS

This application is a continuation application of U.S. patent application Ser. No. 12/131,868, filed on Jun. 2, 2008, which is a divisional application of U.S. patent application Ser. No. 10/608,907, filed on Jun. 27, 2003, now U.S. Pat. No. 7,608,600, which claims the benefit of priority to U.S. Provisional Application No. 60/392,350, filed Jun. 28, 2002; U.S. Provisional Application No. 60/466,194, filed Apr. 28, 2003; and U.S. Provisional Application No. 60/470,949, filed May 14, 2003, the disclosures of each of which are incorporated herein by reference.

A compact disc containing the tables of pages 158-2620 of the parent application (Ser. No. 12/131,868) is hereby incorporated by reference. The compact disc contains a PDF file titled "Tables 11874-244-999," which was created Jun. 24, 2011 and has a size of 114 megabytes.

FIELD OF THE INVENTION

This invention is in the area of pharmaceutical chemistry, and is in particular, a 2' and/or 3' prodrug of 6-modified, 1', 2', 3' or 4'-branched pyrimidine nucleoside or 8-modified, 1', 2', 3' or 4'-branched purine nucleoside for the treatment of a Flaviviridae infection, such as a hepatitis C virus infection.

BACKGROUND OF THE INVENTION

Flaviviridae Viruses

The Flaviviridae family of viruses comprises at least three distinct genera: pestiviruses, which cause disease in cattle and pigs; flaviviruses, which are the primary cause of diseases such as dengue fever and yellow fever; and hepaciviruses, whose sole member is HCV. The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the dengue hemorrhagic fever viruses (DHF), yellow fever virus, shock syndrome and Japanese encephalitis virus (Halstead, S. B., *Rev. Infect. Dis.,* 1984, 6, 251-264; Halstead, S. B., *Science,* 239:476-481, 1988; Monath, T. P., *New Eng. J. Med.,* 1988, 319, 641-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H.-J., *Advances in Virus Research,* 1996, 47, 53-118; Moennig V., et al, *Adv. Vir. Res.* 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are approximately 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al. (1988) *Nature* 333:22; Bazan and Fletterick (1989) *Virology* 171: 637-639; Gorbalenya et al. (1989) *Nucleic Acid Res.* 17.3889-3897). Similarly, the NS5B proteins of pestiviruses and hepaciviruses have the motifs characteristic of RNA-directed RNA polymerases (Koonin, E. V. and Dolja. V. V. (1993) *Crit. Rev. Biochem. Malec. Biol.* 28:375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett (1991) *Virology* 184:341-350; Bartenschlager et al. (1993) *J. Virol.* 67:3835-3844; Eckart et al. (1993) *Biochem. Biophys. Res. Comm.* 192:399-406; Grakoui et al. (1993) *J. Virol.* 67:2832-2843; Grakoui et al. (1993) *Proc. Natl. Acad. Sci. USA* 90:10583-10587; Hijikata et al. (1993) *J. Virol.* 67:4665-4675; Tome et al. (1993) *J. Virol.* 67:4017-4026). The NS4A protein, in both cases, acts as a cofactor with the NS3 serine protease (Bartenschlager et al. (1994) *J. Virol.* 68:5045-5055; Failla et al. (1994) *J. Virol.* 68: 3753-3760; Lin et al. (1994) 68:8147-8157; Xu et al. (1997) *J. Virol.* 71:5312-5322). The NS3 protein of both viruses also functions as a helicase (Kim et al. (1995) *Biochem. Biophys. Res. Comm.* 215: 160-166; Jin and Peterson (1995) *Arch. Biochem. Biophys.,* 323:47-53; Warrener and Collett (1995) *J. Virol.* 69:1720-1726). Finally, the NS5B proteins of pestiviruses and hepaciviruses have the predicted RNA-directed RNA polymerases activity (Behrens et al. (1996) *EMBO J.* 15:12-22; Lchmann et al. (1997) *J. Virol.* 71:8416-8428; Yuan et al. (1997) *Biochem. Biophys. Res. Comm.* 232:231-235; Hagedorn, PCT WO 97/12033; Zhong et al. (1998) *J. Virol.* 72.9365-9369).

Hepatitis C Virus

The hepatitis C virus (HCV) is the leading cause of chronic liver disease worldwide. (Boyer, N. et al. *J. Hepatol.* 32:98-112, 2000). HCV causes a slow growing viral infection and is the major cause of cirrhosis and hepatocellular carcinoma (Di Besceglie, A. M. and Bacon, B. R., *Scientific American*, Oct.: 80-85, (1999); Boyer, N. et al. *J. Hepatol.* 32:98-112, 2000). An estimated 170 million persons are infected with HCV worldwide. (Boyer, N. et al. *J. Hepatol.* 32:98-112, 2000). Cirrhosis caused by chronic hepatitis C infection accounts for 8,000-12,000 deaths per year in the United States, and HCV infection is the leading indication for liver transplantation.

HCV is known to cause at least 80% of posttransfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as Hepatitis B Virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear. (The Merck Manual, ch. 69, p. 901, 16th ed., (1992)).

HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA dependent RNA polymerase. The function of the remaining nonstructural proteins, NS4A and NS4B, and that of NS5A (the amino-terminal half of nonstructural protein 5) remain unknown.

A significant focus of current antiviral research is directed to the development of improved methods of treatment of chronic HCV infections in humans (Di Besceglie, A. M. and Bacon, B. R., *Scientific American*, Oct.: 80-85, (1999)).

Treatment of HCV Infection with Interferon

Interferons (IFNs) have been commercially available for the treatment of chronic hepatitis for nearly a decade. IFNs are glycoproteins produced by immune cells in response to viral infection. IFNs inhibit replication of a number of viruses, including HCV, and when used as the sole treatment for hepatitis C infection, IFN can in certain cases suppress serum HCV-RNA to undetectable levels. Additionally, IFN can normalize serum amino transferase levels. Unfortunately, the effect of IFN is temporary and a sustained response occurs in only 8%-9% of patients chronically infected with HCV (Gary L. Davis. *Gastroenterology* 118:S104-S114, 2000). Most patients, however, have difficulty tolerating interferon treatment, which causes severe flu-like symptoms, weight loss, and lack of energy and stamina.

A number of patents disclose Flaviviridae, including HCV, treatments, using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696. A number of patents also disclose pegylated forms of interferon, such as, U.S. Pat. Nos. 5,747,646, 5,792,834 and 5,834,594 to Hoffmann-La Roche Inc; PCT Publication No. WO 99/32139 and WO 99/32140 to Enzon; WO 95/13090 and U.S. Pat. Nos. 5,738,846 and 5,711,944 to Schering; and U.S. Pat. No. 5,908,621 to Glue et al.

Interferon alpha-2a and interferon alpha-2b are currently approved as monotherapy for the treatment of HCV. ROFERON®-A (Roche) is the recombinant form of interferon alpha-2a. PEGASYS® (Roche) is the pegylated (i.e. polyethylene glycol modified) form of interferon alpha-2a. INTRON®A (Schering Corporation) is the recombinant form of Interferon alpha-2b, and PEG-INTRON® (Schering Corporation) is the pegylated form of interferon alpha-2b.

Other forms of interferon alpha, as well as interferon beta, gamma, tau and omega are currently in clinical development for the treatment of HCV. For example, INFERGEN (interferon alphacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and interferon gamma, interferon tau, and interferon gamma-1b by InterMune are in development.

Ribivarin

Ribavirin (1-β-D-ribofuranosyl-1-1,2,4-triazole-3-carboxamide) is a synthetic, non-interferon-inducing, broad spectrum antiviral nucleoside analog sold under the trade name, Virazole (The Merck Index, 11th edition, Editor: Budavari, S., Merck & Co., Inc., Rahway, N. J., p 1304, 1989). U.S. Pat. No. 3,798,209 and RE29,835 disclose and claim ribavirin. Ribavirin is structurally similar to guanosine, and has in vitro activity against several DNA and RNA viruses including Flaviviridae (Gary L. Davis. Gastroenterology 118:S104-S114, 2000).

Ribavirin reduces serum amino transferase levels to normal in 40% of patients, but it does not lower serum levels of HCV-RNA (Gary L. Davis. Gastroenterology 118:S104-S114, 2000). Thus, ribavirin alone is not effective in reducing viral RNA levels. Additionally, ribavirin has significant toxicity and is known to induce anemia.

Ribivirin is not approved fro monotherapy against HCV. It has been approved in combination with interferon alpha-2a or interferon alpha-2b for the treatment of HCV.

Combination of Interferon and Ribavirin

The current standard of care for chronic hepatitis C is combination therapy with an alpha interferon and ribavirin. The combination of interferon and ribavirin for the treatment of HCV infection has been reported to be effective in the treatment of interferon naïve patients (Battaglia, A. M. et al., *Ann. Pharmacother.* 34:487-494, 2000), as well as for treatment of patients when histological disease is present (Berenguer, M. et al. *Antivir. Ther.* 3(Suppl. 3):125-136, 1998). Studies have show that more patients with hepatitis C respond to pegylated interferon-alpha/ribavirin combination therapy than to combination therapy with unpegylated interferon alpha. However, as with monotherapy, significant side effects develop during combination therapy, including hemolysis, flu-like symptoms, anemia, and fatigue. (Gary L. Davis. *Gastroenterology* 118:S104-S114, 2000).

Combination therapy with PEG-INTRONS (peginterferon alpha-2b) and REBETOL® (Ribavirin, USP) Capsules is available from Schering Corporation. REBETOL® (Schering Corporation) has also been approved in combination with INTRON® A (Interferon alpha-2b, recombinant, Schering Corporation). Roche's PEGASYS® (pegylated interferon alpha-2a) and COPEGUS® (ribavirin) are also approved for the treatment of HCV.

PCT Publication Nos. WO 99/59621, WO 00/37110, WO 01/81359, WO 02/32414 and WO 03/024461 by Schering Corporation disclose the use of pegylated interferon alpha and ribavirin combination therapy for the treatment of HCV. PCT Publication Nos. WO 99/15194, WO 99/64016, and WO 00/24355 by Hoffmann-La Roche Inc also disclose the use of pegylated interferon alpha and ribavirin combination therapy for the treatment of HCV.

Additional Methods to Treat Flaviviridae Infections

The development of new antiviral agents for flaviviridae infections, especially hepatitis C, is currently underway. Specific inhibitors of HCV-derived enzymes such as protease, helicase, and polymerase inhibitors are being developed. Drugs that inhibit other steps in HCV replication are also in development, for example, drugs that block production of HCV antigens from the RNA (IRES inhibitors), drugs that prevent the normal processing of HCV proteins (inhibitors of glycosylation), drugs that block entry of HCV into cells (by blocking its receptor) and nonspecific cytoprotective agents that block cell injury caused by the virus infection. Further, molecular approaches are also being developed to treat hepatitis C, for example, ribozymes, which are enzymes that break down specific viral RNA molecules, and antisense oligonucleotides, which are small complementary segments of DNA that bind to viral RNA and inhibit viral replication, are under investigation. A number of HCV treatments are reviewed by Bymock et al. in *Antiviral Chemistry & Chemotherapy*, 11:2; 79-95 (2000) and De Francesco et al. in *Antiviral Research*, 58: 1-16 (2003).

Examples of classes of drugs that are being developed to treat Flaviviridae infections include:

(1) Protease Inhibitors

Substrate-based NS3 protease inhibitors (Attwood et al., Antiviral peptide derivatives, PCT WO 98/22496, 1998; Attwood et al., *Antiviral Chemistry and Chemotherapy* 1999, 10, 259-273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734) are being investigated.

Non-substrate-based NS3 protease inhibitors such as 2,4,6-trihydroxy-3-nitro-benzamide derivatives (Sudo K. et al., *Biochemical and Biophysical Research Communications*, 1997, 238, 643-647; Sudo K. et al. *Antiviral Chemistry and Chemotherapy*, 1998, 9, 186), including RD3-4082 and RD3-4078, the former substituted on the amide with a 14 carbon chain and the latter processing a para-phenoxyphenyl group are also being investigated.

Sch 68631, a phenanthrenequinone, is an HCV protease inhibitor (Chu M. et al., *Tetrahedron Letters* 37:7229-7232, 1996). In another example by the same authors, Sch 351633, isolated from the fungus *Penicillium griseofulvum*, was identified as a protease inhibitor (Chu M. et al., *Bioorganic and Medicinal Chemistry Letters* 9:1949-1952). Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al. Peptides as NS3 serine protease inhibitors of HCV are disclosed in WO 02/008251 to Corvas International, Inc, and WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 to Schering Corporation. Imidazoleidinones as NS3 serine protease inhibitors of HCV are disclosed in WO 02/08198 to Schering Corporation and WO 02/48157 to Bristol Myers Squibb. WO 98/17679 to Vertex Pharmaceuticals and WO 02/48116 to Bristol Myers Squibb also disclose HCV protease inhibitors.

(2) Thiazolidine derivatives which show relevant inhibition in a reverse-phase HPLC assay with an NS3/4A fusion protein and NS5A/5B substrate (Sudo K. et al, *Antiviral Research*, 1996, 32, 9-18), especially compound RD-1-6250, possessing a fused cinnamoyl moiety substituted with a long alkyl chain, RD4 6205 and RD4 6193;

(3) Thiazolidines and henzanilides identified in Kakiuchi N. et al. *J. EBS Letters* 421, 217-220; Takeshita N. et al. *Analytical Biochemistry*, 1997, 247, 242-246;

(4) A phenan-threnequinone possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), and Sch 351633, isolated from the fungus *Penicillium griseofulvum*, which demonstrates activity in a scintillation proximity assay (Chu M. et al., *Bioorganic and Medicinal Chemistry Letters* 9, 1949-1952);

(5) Helicase inhibitors (for example Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(6) Nucleotide polymerase inhibitors and gliotoxin (Ferrari R. et al. *Journal of Virology*, 1999, 73, 1649-1654), and the natural product cerulenin (Lohmann V. et al., *Virology*, 1998, 249, 108-118);

(7) Antisense phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);

(8) Inhibitors of IRES-dependent translation (Ikeda N et al., Agent for the prevention and treatment of hepatitis C, Japanese Patent Pub. JP-08268890; Kai Y. et al. Prevention and treatment of viral diseases, Japanese Patent Pub. JP-10101591);

(9) Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.; and

(10) Nucleoside analogs have also been developed for the treatment of Flaviviridae infections.

Idenix Pharmaceuticals discloses the use of branched nucleosides in the treatment of flaviviruses (including HCV) and pestiviruses in International Publication Nos. WO 01/90121 and WO 01/92282. Specifically, a method for the treatment of hepatitis C infection (and flaviviruses and pestiviruses) in humans and other host animals is disclosed in the Idenix publications that includes administering an effective amount of a biologically active 1', 2', 3' or 4'-branched β-D or β-L nucleosides or a pharmaceutically acceptable salt or derivative thereof, administered either alone or in combination with another antiviral agent, optionally in a pharmaceutically acceptable carrier.

Other patent applications disclosing the use of certain nucleoside analogs to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc., PCT/EP01/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48165 by Pharmasset, Ltd.

PCT Publication No. WO 99/43691 to Emory University, entitled "2'-Fluoronucleosides" discloses the use of certain 2'-fluoronucleosides to treat HCV.

Eldrup et al. (Oral Session V, Hepatitis C Virus, Flaviviridae; 16th International Conference on Antiviral Research (Apr. 27, 2003, Savannah, Ga.)) described the structure activity relationship of 2'-modified nucleosides for inhibition of HCV.

Bhat et al. (Oral Session V, Hepatitis C Virus, Flaviviridae, 2003 (Oral Session V, Hepatitis C Virus, Flaviviridae; 16th International Conference on Antiviral Research (Apr. 27, 2003, Savannah, Ga.); p A75) describe the synthesis and pharmacokinetic properties of nucleoside analogues as possible inhibitors of HCV RNA replication. The authors report that 2'-modified nucleosides demonstrate potent inhibitory activity in cell-based replicon assays.

Olsen et al. (Oral Session V, Hepatitis C Virus, Flaviviridae; 16th International Conference on Antiviral Research (Apr. 27, 2003, Savannah, Ga.) p A76) also described the effects of the 2'-modified nucleosides on HCV RNA replication.

(11) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperidenes (U.S. Pat. No. 5,830,905 to Diana et al.).

(12) Other compounds currently in preclinical or clinical development for treatment of hepatitis C virus include: Interleukin-10 by Schering-Plough, IP-501 by Interneuron, Merimebodib (VX-497) by Vertex, AMANTADINE® (Symmetrel) by Endo Labs Solvay, HEPTAZYME® by RPI, IDN-6556 by Idun Pharma., XTL-002 by XTL., HCV/MF59 by Chiron, CIVACIR® (Hepatitis C Immune Globulin) by NABI, LEVOVIRIN® by ICN/Ribapharm, VIRAMIDINE® by ICN/Ribapharm, ZADAXIN® (thymosin alpha-1) by Sci Clone, thymosin plus pegylated interferon by Sci Clone, CEPLENE® (histamine dihydrochloride) by Maxim, VX 950/LY 570310 by Vertex/Eli Lilly, ISIS14803 by Isis Pharmaceutical/Elan, IDN-6556 by Idun Pharmaceuticals, Inc., JTK 003 by AKROS Pharma, BILN-2061 by Boehringer Ingelheim, CellCept (mycophenolate mofetil) by Roche, T67, a β-tubulin inhibitor, by Tularik, a therapeutic vaccine directed to E2 by Innogenetics, FK788 by Fujisawa Healthcare, Inc., IdB 1016 (Siliphos, oral silybin-phosphatdylcholine phytosome), RNA replication inhibitors (VP50406) by ViroPharma/Wyeth, therapeutic vaccine by Intercell, therapeutic vaccine by Epimmune/Genencor, IRES inhibitor by Anadys, ANA 245 and ANA 246 by Anadys, immunotherapy (Therapore) by Avant, protease inhibitor by Corvas/SChering, helicase inhibitor by Vertex, fusion inhibitor by Trimeris, T cell therapy by CellExSys, polymerase inhibitor by Biocryst, targeted RNA chemistry by PTC Therapeutics, Dication by Immtech, Int., protease inhibitor by Agouron, protease inhibitor by Chiron/Medivir, antisense therapy by AVI BioPharma, antisense therapy by Hybridon, hemopurifier by Aethlon Medical, therapeutic vaccine by Merix, protease inhibitor by Bristol-Myers Squibb/Axys, Chron-VacC, a therapeutic vaccine, by Tripep, Utah 231B by United Therapeutics, protease, helicase and polymerase inhibitors by Genelabs Technologies, IRES inhibitors by Immusol, R803 by Rigel Pharmaceuticals, INFERGEN® (interferon alpha-con-1) by InterMune, OMNIFERON® (natural interferon) by Viragen, ALBUFERON® by Human Genome Sciences, REBIF® (interferon beta-1a) by Ares-Serono, Omega Interferon by BioMedicine, Oral Interferon Alpha by Amarillo Biosciences, interferon gamma, interferon tau, and Interferon gamma-1b by InterMune.

Nucleoside prodrugs have been previously described for the treatment of other forms of hepatitis. WO 00/09531 (filed Aug. 10, 1999) and WO 01/96353 (filed Jun. 15, 2001) to Idenix Pharmaceuticals discloses 2'-deoxy-β-L-nucleosides and their 3'-prodrugs for the treatment of HBV. U.S. Pat. No. 4,957,924 to Beauchamp discloses various therapeutic esters of acyclovir.

In light of the fact that HCV infection has reached epidemic levels worldwide, and has tragic effects on the infected patient, there remains a strong need to provide new effective pharmaceutical agents to treat hepatitis C that have low toxicity to the host.

Further, given the rising threat of other flaviviridae infections, there remains a strong need to provide new effective pharmaceutical agents that have low toxicity to the host.

Therefore, it is an object of the present invention to provide a compound, method and composition for the treatment of a host infected with hepatitis C virus.

It is another object of the present invention to provide a method and composition generally for the treatment of patients infected with pestiviruses, Flaviviruses, or hepaciviruses.

SUMMARY OF THE INVENTION

2' and 3'-prodrugs of 1', 2', 3' or 4'-branched β-D or β-L nucleosides, or their pharmaceutically acceptable salts or pharmaceutically acceptable formulations containing these compounds are useful in the prevention and treatment of Flaviviridae infections and other related conditions such as anti-Flaviviridae antibody positive and Flaviviridae-positive conditions, chronic liver inflammation caused by HCV, cirrhosis, acute hepatitis, fulminant hepatitis, chronic persistent hepatitis, and fatigue. These compounds or formulations can also be used prophylactically to prevent or retard the progression of clinical illness in individuals who are anti-Flaviviridae antibody or Flaviviridae-antigen positive or who have been exposed to a Flaviviridae.

A method for the treatment of a Flaviviridae viral infection in a host, including a human, is also disclosed that includes administering an effective amount of a 2' or 3'-prodrug of a biologically active 1', 2', 3' or 4'-branched β-D or β-L nucleoside or a pharmaceutically acceptable salt thereof, administered either alone or in combination or alternation with another anti-Flaviviridae agent, optionally in a pharmaceutically acceptable carrier. The term 2'-prodrug, as used herein, refers to a 1', 2', 3' or 4'-branched β-D or nucleoside that has a biologically cleavable moiety at the 2'-position, including, but not limited to acyl, and in one embodiment, a natural or synthetic D or L amino acid, preferably an L-amino acid. The term 3'-prodrug, as used herein, refers to a 1', 2', 3' or 4'-branched β-D or β-L nucleoside that has a biologically cleavable moiety at the 3'-position, including, but not limited to acyl, and in one embodiment, a natural or synthetic D or L amino acid, preferably an L-amino acid.

Pharmaceutically acceptable salts include tosylate, methanesulfonate, acetate, citrate, malonate, tartarate, succinate, benzoate, ascorbate, α-ketoglutarate, and α-glycerophosphate, formate, fumarate, propionate, glycolate, lactate, pyruvate, oxalate, maleate, salicyate, sulfate, sulfonate, nitrate, bicarbonate, hydrobromate, hydrobromide, hydroiodide, carbonate, and phosphoric acid salts. A particularly preferred embodiment is the mono or dihydrochloride salt.

In one embodiment, the 1', 2', 3' or 4'-branched β-D or β-L nucleoside includes biologically cleavable moieties at the 2' and/or 5' positions. Preferred moieties are natural or synthetic D or L amino acid esters, including D or L-valyl, though preferably L-amino acid esters, such as L-valyl, and alkyl esters including acetyl. Therefore, this invention specifically includes 2'-D or L-amino acid ester and 2',5'-D or L-diamino acid ester, preferably L-amino acid ester, of 1', 2', 3' or 4'-branched or β-L nucleosides with any desired purine or pyrimidine base, wherein the parent drug optionally has an $EC_{50}$ of less than 15 micromolar, and even more preferably less than 10 micromolar; 2'-(alkyl or aryl) ester or 2',5'-di(alkyl or aryl) ester of 1', 2', 3' or 4'-branched β-D or β-L nucleosides with any desired purine or pyrimidine base, wherein the parent drug optionally has an $EC_{50}$ of less than 10 or 15 micromolar; and prodrugs of 2',5'-diesters of 1', 2', 3' or 4'-branched β-D or β-L nucleosides wherein (i) the 2' ester is a natural or synthetic D or L-amino acid ester, though preferably an L-amino acid ester, and the 5'-ester is an alkyl or aryl ester; (ii) both esters are independently natural or synthetic D or L-amino acid ester, though preferably both are L-amino acid esters; (iii) both esters are independently alkyl or aryl esters; and (iv) the 2' ester is independently an alkyl or aryl ester and the 5'-ester is a natural or synthetic D or L-amino acid ester, though preferably an L-amino acid ester, wherein the parent drug optionally has an $EC_{50}$ of less than 10 or 15 micromolar. Examples of prodrugs falling within the invention are 2'-D or L-valine ester of β-D-2',6-dimethyl-cytidine; 2'-L-valine ester of β-D-2',6-dimethyl-thymidine; 2'-L-valine ester of β-D-2',8-dimethyl-adenosine; 2'-L-valine ester of β-D-2',8-dimethyl-guanosine; 2'-L-valine ester of β-D-2',6-dimethyl-5-fluorocytidine; 2'-L-valine ester of β-D-2',6-dimethyl-uridine; 2'-acetyl ester of β-D-2',6-dimethyl-cytidine; 2'-acetyl ester of β-D-2',6-dimethyl-thymidine; 2'-acetyl ester of β-D-2',8-dimethyl-adenosine; 2'-acetyl ester of β-D-2',8-dimethyl-guanosine; 2'-acetyl ester of β-D-2',6-dimethyl-5-fluoro-cytidine; and 2'-esters of β-D-2',6-dimethyl-(cytidine, 5-fluorocytidine, uridine or thymidine) or 2'-esters of β-D-2',8-dimethyl-(guanosine, adenosine or inosine) wherein (i) the 2' ester is an amino acid ester; or (ii) the 2' ester is an alkyl or aryl ester.

Additional examples of prodrugs falling within the invention are 2',5'-L-divaline ester of β-D-2',6-dimethyl-cytidine (dival-2',6-diMe-L-dC); 2',5'-L-divaline ester of β-D-2',6-dimethyl-thymidine; 2',5'-L-divaline ester of β-D-2',8-dimethyl-adenosine; 2',5'-L-divaline ester of β-D-2',8-dimethyl-guanosine; 2',5'-L-divaline ester of β-D-2',6-dimethyl-5-fluoro-cytidine; 2',5'-L-divaline ester of β-D-2',6-dimethyl-uridine; 2',5'-diacetyl ester of β-D-2',6-dimethyl-cytidine; 2',5'-diacetyl ester of β-D-2',6-dimethyl-thymidine; 2',5'-diacetyl ester of β-D-2',8-dimethyl-adenosine; 2',5'-diacetyl ester of β-D-2',8-dimethyl-guanosine; 2',5'-diacetyl ester of β-D-2',6-dimethyl-5-fluoro-cytidine; and 2',5'-diesters of β-D-2',6-dimethyl-(cytidine, 5-fluorocytidine, uridine or thymidine) or 2',5'-diesters of β-D-2',8-dimethyl-(guanosine, adenosine or inosine) wherein (i) the 2' ester is an amino acid ester and the 5'-ester is an alkyl or aryl ester; (ii) both esters are amino acid esters; (iii) both esters are independently alkyl or aryl esters; or (iv) the 2' ester is an alkyl or aryl ester and the 5'-ester is an amino acid ester.

In another embodiment, the 1', 2', 3' or 4'-branched β-D or β-L nucleoside 3'-prodrug includes biologically cleavable moieties at the 3' and/or 5' positions. Preferred moieties are natural or synthetic D or L amino acid esters, such as valyl, though preferably L-amino acids, such as L-valyl, and alkyl esters including acetyl. Therefore, this invention specifically includes 3'-L-amino acid ester and 3',5'-L-diamino acid ester of 1', 2', 3' or 4'-branched β-D or β-L nucleosides with any desired purine or pyrimidine base, wherein the parent drug optionally has an $EC_{50}$ of less than 15 micromolar, and even more preferably less than 10 micromolar; 3'-(alkyl or aryl) ester or 3',5'-L-di(alkyl or aryl) ester of 1', 2', 3' or 4'-branched β-D or β-L nucleosides with any desired purine or pyrimidine base, wherein the parent drug optionally has an $EC_{50}$ of less than 10 or 15 micromolar; and prodrugs of 3',5'-diesters of 1', 2', 3' or 4'-branched β-D or β-L nucleosides wherein (i) the 3' ester is a natural or synthetic D or L amino acid ester and the 5'-ester is an alkyl or aryl ester; (ii) both esters are natural or synthetic D or L-amino acid esters; (iii) both esters are independently alkyl or aryl esters; and (iv) the 3' ester is independently an alkyl or aryl ester and the 5'-ester is a natural or synthetic D or L-amino acid ester, wherein the parent drug optionally has an $EC_{50}$ of less than 10 or 15 micromolar.

Examples of prodrugs falling within the invention are 3'-L-valine ester of β-D-2',6-dimethyl-cytidine; 3'-L-valine ester of β-D-2',6-dimethyl-thymidine; 3'-L-valine ester of β-D-2',8-dimethyl-adenosine; 3'-L-valine ester of β-D-2',8-dimethyl-guanosine; 3'-L-valine ester of β-D-2',6-dimethyl-5-fluorocytidine; 3'-L-valine ester of β-D-2',6-dimethyl-uridine; 3'-acetyl ester of β-D-2',6-dimethyl-cytidine; 3'-acetyl ester of β-D-2',6-dimethyl-thymidine; 3'-acetyl ester of β-D-2',8-dimethyl-adenosine; 3'-acetyl ester of β-D-2',8-dimethyl-guanosine; 3'-acetyl ester of β-D-2',6-dimethyl-5-fluoro-cytidine; and 3'-esters of β-D-2',6-dimethyl- (cytidine, 5-fluorocytidine, uridine or thymidine) or 3'-esters of β-D-2',8-dimethyl-(guanosine, adenosine or inosine) wherein (i) the 3' ester is an amino acid ester; or (ii) the 3' ester is an alkyl or aryl ester.

Additional examples of prodrugs falling within the invention are 3',5'-L-divaline ester of β-D-2',6-dimethyl-cytidine (dival-2',6-diMe-L-dC); 3',5'-L-divaline ester of β-D-2',6-dimethyl-thymidine; 3',5'-L-divaline ester of β-D-2',8-dimethyl-adenosine; 3',5'-L-divaline ester of β-D-2',8-dimethyl-guanosine; 3',5'-L-divaline ester of β-D-2',6-dimethyl-5-fluoro-cytidine; 3',5'-L-divaline ester of β-D-2',6-dimethyl-uridine; 3',5'-diacetyl ester of β-D-2',6-dimethyl-cytidine; 3',5'-diacetyl ester of β-D-2',6-dimethyl-thymidine; 3',5'-diacetyl ester of β-D-2',8-dimethyl-adenosine; 3',5'-diacetyl ester of β-D-2',8-dimethyl-guanosine; 3',5'-diacetyl ester of β-D-2',6-dimethyl-5-fluoro-cytidine; and 3',5'-diesters of β-D-2',6-dimethyl-(cytidine, 5-fluorocytidine, uridine or thymidine) or 3',5'-diesters of β-D-2',8-dimethyl-(guanosine, adenosine or inosine) wherein (i) the 3' ester is an amino acid ester and the 5'-ester is an alkyl or aryl ester; (ii) both esters are amino acid esters; (iii) both esters are independently alkyl or aryl esters; or (iv) the 3' ester is an alkyl or aryl ester and the 5'-ester is an amino acid ester.

In another embodiment, the prodrug of 1', 2', 3' or 4'-branched β-D or β-L nucleoside includes biologically cleavable moieties at the 2', 3' and/or 5' positions. Preferred moieties are natural or synthetic D or L amino acid esters, including D or L-valyl, though preferably L-amino acid esters, such as L-valyl, and alkyl esters including acetyl. Therefore, this invention specifically includes 2',3'-L or D-diamino acid ester and 2',3',5'-L or D-triamino acid ester of 1', 2', 3' or 4'-branched β-D or β-L nucleosides, preferrably L-amino acid, with any desired purine or pyrimidine base, wherein the parent drug optionally has an $EC_{50}$ of less than 15 micromolar, and even more preferably less than 10 micromolar; 2',3'-di(alkyl or aryl) ester or 2',3',5'-L-tri(alkyl or aryl) ester of 1', 2', 3' or 4'-branched β-D or β-L, nucleosides with any desired purine or pyrimidine base, wherein the parent drug optionally has an $EC_{50}$ of less than 10 or 15 micromolar; and prodrugs of 2',3'-diesters of 1', 2', 3' or 4'-branched β-D or β-L nucleosides wherein (i) the 2' ester is an amino acid ester and the 3'-ester is an alkyl or aryl ester; (ii) both esters are amino acid esters; (iii) both esters are independently alkyl or aryl esters; and (iv) the 2' ester is independently an alkyl or aryl ester and the 3'-ester is an amino acid ester, wherein the parent drug optionally has an $EC_{50}$ of less than 10 or 15 micromolar. Further, 2',3',5'-triesters of 1', 2', 3' or 4'-branched β-D or β-L nucleosides wherein (i) all three esters are amino acid esters; (ii) all three esters are independently alkyl or aryl esters; (iii) the 2' ester is an amino acid ester, the 3' ester is an amino acid ester and the 5'-ester is an alkyl or aryl ester; (iv) the 2' ester is an amino acid ester, the 3' ester is an alkyl or aryl ester and the 5'-ester is an alkyl or aryl ester; (v) the 2' ester is an alkyl or aryl ester, the 3' ester is an alkyl or aryl ester and the 5'-ester is an amino acid ester; (vi) the 2' ester is an alkyl or aryl ester, the 3' ester is an amino acid ester and the 5'-ester is an amino acid ester; (vii) the 2' ester is an alkyl or aryl ester, the 3' ester is an amino acid ester and the 5'-ester is an alkyl or aryl ester; and (viii) the 2' ester is an amino acid ester, the 3' ester is an alkyl or aryl ester and the 5'-ester is an amino acid ester; wherein the parent drug optionally has an $EC_{50}$ of less than 10 or 15 micromolar.

Examples of prodrugs falling within the invention include 2',3'-L-divaline ester of β-D-2',6-dimethyl-cytidine (dival-2',6-diMe-L-dC); 2',3'-L-divaline ester of β-D-2',6-dimethyl-thymidine; 2',3'-L-divaline ester of β-D-2',8-dimethyl-adenosine; 2',3'-L-divaline ester of β-D-2',8-dimethyl-guanosine; 2',3'-L-divaline ester of β-D-2',6-dimethyl-5-fluorocytidine; 2',3'-L-divaline ester of β-D-2',6-dimethyl-uridine; 2',3'-diacetyl ester of β-D-2',6-dimethyl-cytidine; 2',3'-diacetyl ester of β-D-2',6-dimethyl-thymidine; 2',3'-diacetyl ester of β-D-2',8-dimethyl-adenosine; 2',3'-diacetyl ester of β-D-2',8-dimethyl-guanosine; 2',3'-diacetyl ester of β-D-2',6-dimethyl-5-fluoro-cytidine; and 2',3'-diesters of β-D-2',6-dimethyl-(cytidine, 5-fluorocytidine, uridine or thymidine) or 2',3'-diesters of β-D-2',8-dimethyl-(guanosine, adenosine or inosine) wherein (i) the 2' ester is an amino acid ester and the 3'-ester is an alkyl or aryl ester; (ii) both esters are amino acid esters; (iii) both esters are independently alkyl or aryl esters; or (iv) the 2' ester is an alkyl or aryl ester and the 3'-ester is an amino acid ester.

Additional examples of prodrugs falling within the invention include 2',3',5'-L-trivaline ester of β-D-2',6-dimethyl-cytidine (trival-2',6-diMe-L-dC); 2',3',5'-L-trivaline ester of β-D-2',6-dimethyl-thymidine; 2',3',5'-L-trivaline ester of β-D-2',8-dimethyl-adenosine; 2',3',5'-L-trivaline ester of β-D-2',8-dimethyl-guanosine; 2',3',5'-L-trivaline ester of β-D-2',6-dimethyl-5-fluoro-cytidine; 2',3',5'-L-trivaline ester of β-D-2',6-dimethyl-uridine; 2',3',5'-triacetyl ester of β-D-2',6-dimethyl-cytidine; 2',3',5'-triacetyl ester of β-D-2',6-dimethyl-thymidine; 2',3',5'-triacetyl ester of β-D-2',8-dimethyl-adenosine; 2',3',5'-triacetyl ester of β-D-2',8-dimethyl-guanosine; 2',3',5'-triacetyl ester of β-D-2'6-dimethyl-5-fluoro-cytidine; and 2',3',5'-triesters of β-D-2',6-dimethyl-(cytidine, 5-fluorocytidine, uridine or thymidine) and 2',3',5'-triesters of β-D-2',8-dimethyl-(guanosine, adenosine or inosine) wherein (i) all three esters are amino acid esters; (ii) all three esters are independently alkyl or aryl esters; (iii) the 2' ester is an amino acid ester, the 3' ester is an amino acid ester and the 5'-ester is an alkyl or aryl ester; (iv) the 2' ester is an amino acid ester, the 3' ester is an alkyl or aryl ester and the 5'-ester is an alkyl or aryl ester; (v) the 2' ester is an alkyl or aryl ester, the 3' ester is an alkyl or aryl ester and the 5'-ester is an amino acid ester; (vi) the 2' ester is an alkyl or aryl ester, the 3' ester is an amino acid ester and the 5'-ester is an amino acid ester; (vii) the 2' ester is an alkyl or aryl ester, the 3' ester is an amino acid ester and the 5'-ester is an alkyl or aryl ester; and (viii) the 2' ester is an amino acid ester, the 3' ester is an alkyl or aryl ester and the 5'-ester is an amino acid ester.

In a first principal embodiment, a compound of Formula (I) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (I):

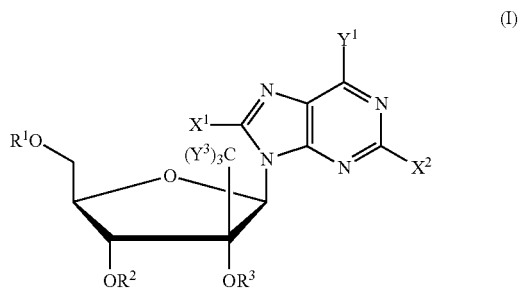

(I)

or a pharmaceutically acceptable salt or prodrug, or a stereoisomeric, tautomeric or polymorphic form thereof, wherein:
$R^1$, $R^2$ and $R^3$ are independently H, phosphate (including mono-, di- or triphosphate and a stabilized phosphate);

straight chained, branched or cyclic alkyl (including lower alkyl); acyl (including lower acyl); CO-alkyl, CO-aryl, CO-alkoxyalkyl, CO-aryloxyalkyl, CO-substituted aryl, sulfonate ester including alkyl or arylalkyl sulfonyl including methanesulfonyl and benzyl, wherein the phenyl group is optionally substituted with one or more substituents as described in the definition of aryl given herein; alkylsulfonyl, arylsulfonyl, aralkylsulfonyl, a lipid, including a phospholipid; an amino acid; and amino acid residue, a carbohydrate; a peptide; cholesterol; or other pharmaceutically acceptable leaving group which is capable of providing a compound wherein $R^1$, $R^2$ and/or $R^3$ is independently H or phosphate (including mono-, di- or triphosphate), for example when administered in vivo; wherein in one embodiment $R^2$ and/or $R^3$ is not phosphate (including mono-, di- or triphosphate or a stabilized phosphate prodrug);

wherein at least one of $R^2$ and $R^3$ is not hydrogen; and wherein:

$Y^1$ is hydrogen, bromo, chloro, fluoro, iodo, CN, OH, $OR^4$, $NH_2$, $NHR^4$, $NR^4R^5$, SH or $SR^4$;

$X^1$ is a straight chained, branched or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted alkenyl, optionally substituted alkynyl, COOH, $COOR^4$, COO-alkyl, COO-aryl, CO—Oalkoxyalkyl, $CONH_2$, $CONHR^4$, $CON(R^4)_2$, chloro, bromo, fluoro, iodo, CN, $N_3$, OH, $OR^4$, $NH_2$, $NHR^4$, $NR^4R^5$, SH or $SR^5$; and $X^2$ is straight chained, branched or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted alkenyl, optionally substituted alkynyl, COOH, $COOR^4$, COO-alkyl, COO-aryl, CO—Oalkoxyalkyl, $CONH_2$, $CONHR^4$, $CON(R^4)_2$, chloro, bromo, fluoro, iodo, CN, $N_3$, OH, $OR^4$, $NH_2$, $NHR^4$, $NR^4R^5$, SH or $SR^5$; and wherein each $Y^3$ is independently H, F, Cl, Br or I;

each $R^4$ and $R^5$ is independently hydrogen, acyl (including lower acyl), alkyl (including but not limited to methyl, ethyl, propyl and cyclopropyl), lower alkyl, alkenyl, alkynyl or cycloalkyl.

In the embodiments described herein, $R^1$, $R^2$ and/or $R^3$ may be a pharmaceutically acceptable leaving group which is capable of providing a compound wherein $R^1$, $R^2$ and/or $R^3$ is independently H or phosphate (including mono-, di- or triphosphate), for example when administered in vivo.

In a second principal embodiment, a compound of Formula (II) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (II):

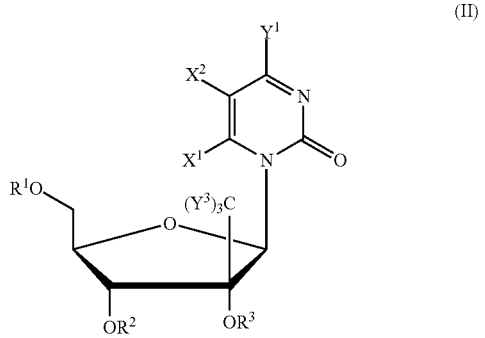

(II)

or a pharmaceutically acceptable salt or prodrug, or a stereoisomeric, tautomeric or polymorphic form thereof, wherein: $R^1$, $R^2$, $R^3$, $R^4$, $R^5$, $Y^1$, $Y^3$, $X^1$ and $X^2$ are as defined above.

In a third principal embodiment, a compound of Formula (III), (IV) or (V), or a pharmaceutically acceptable salt or prodrug, or a stereoisomeric, tautomeric, or polymorphic form thereof, is provided, as well as a method for the treatment of a host infected with a Flaviviridae comprising administering an effective treatment amount of compound of Formula (III), (IV) or (V):

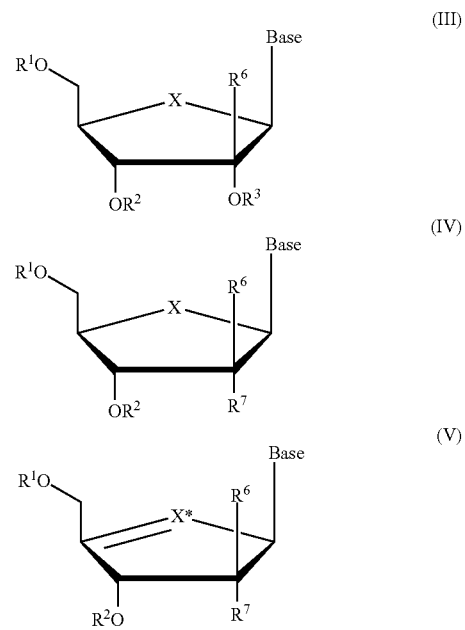

or a pharmaceutically acceptable salt or prodrug, or a stereoisomeric, tautomeric or polymorphic form thereof, wherein: Base is selected from the group consisting of

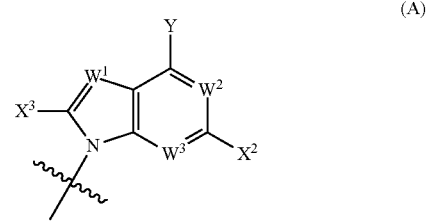

(A)

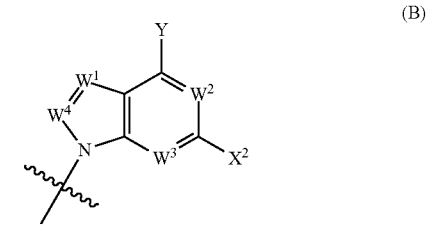

(B)

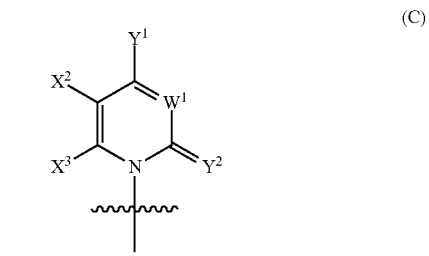

(C)

-continued
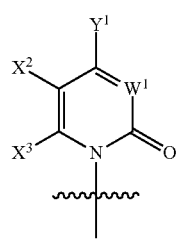 (D)
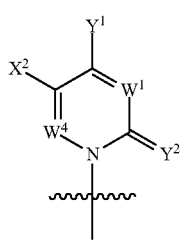 (E)
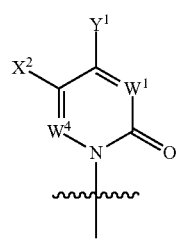 (F)
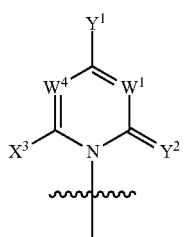 (G)
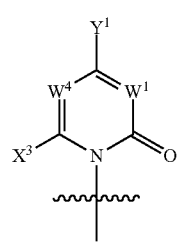 (H)
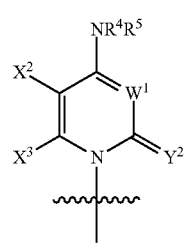 (I)
-continued
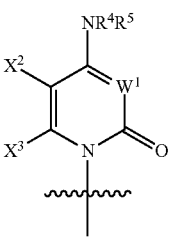 (J)
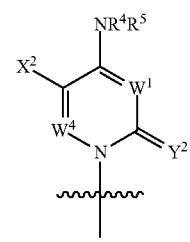 (K)
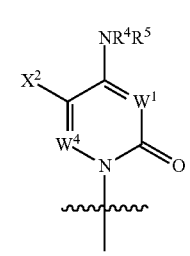 (L)
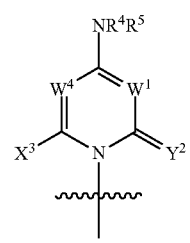 (M)
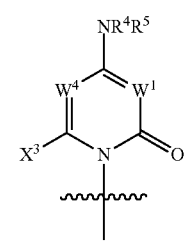 (N)
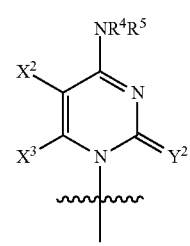 (O)

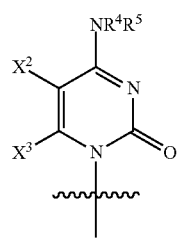 (P)
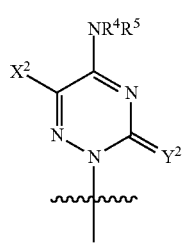 (Q)
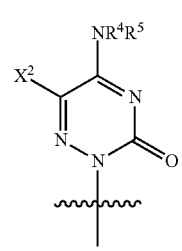 (R)
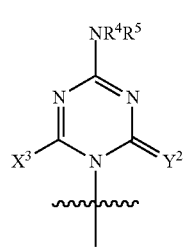 (S)
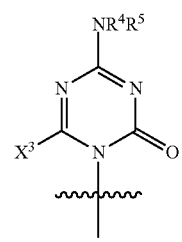 (T)
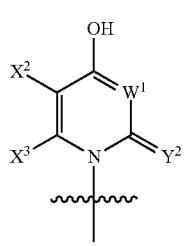 (U)
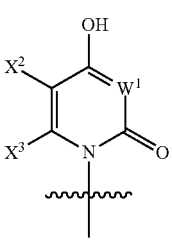 (V)
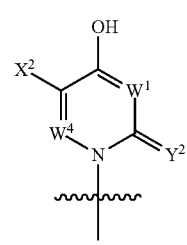 (W)
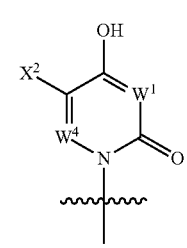 (X)
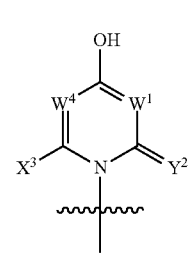 (Y)
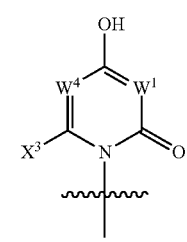 (Z)
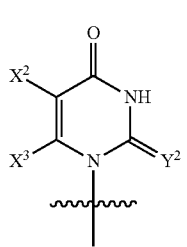 (AA)

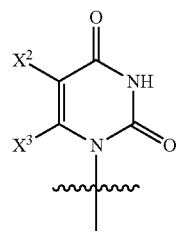 (AB)
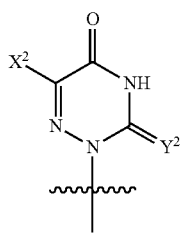 (AC)
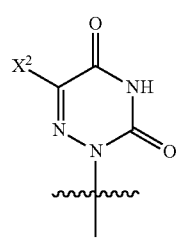 (AD)
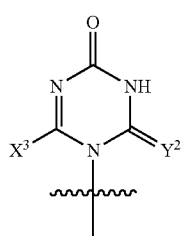 (AE)
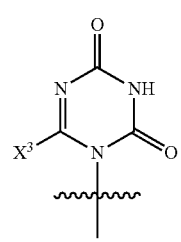 (AF)
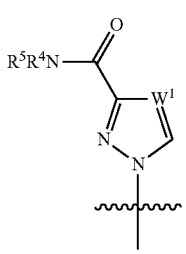 (AG)
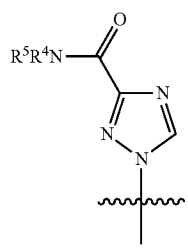 (AH)
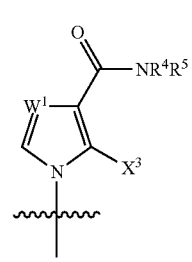 (AI)
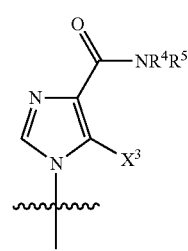 (AJ)
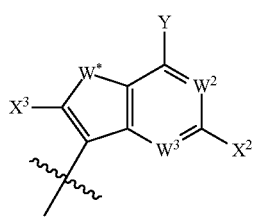 (BA)
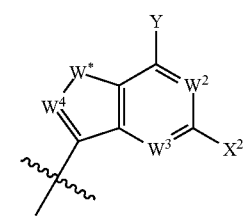 (BB)
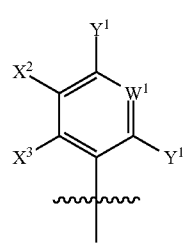 (BC)

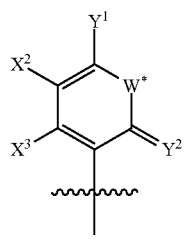 (BD)
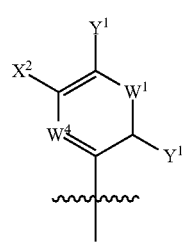 (BE)
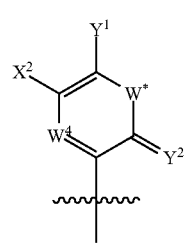 (BF)
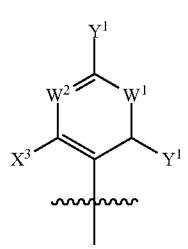 (BG)
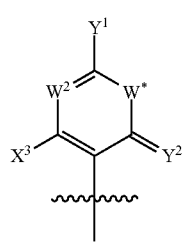 (BH)
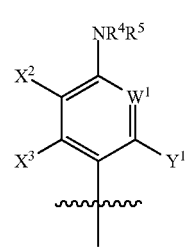 (BI)
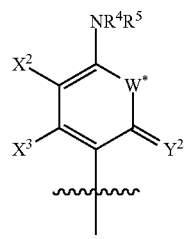 (BJ)
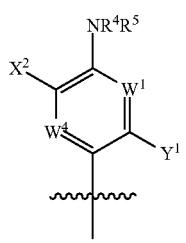 (BK)
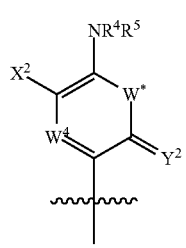 (BL)
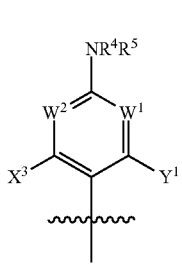 (BM)
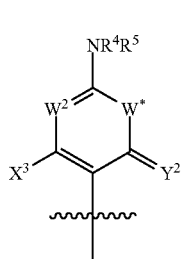 (BN)
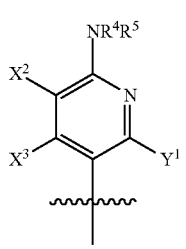 (BO)

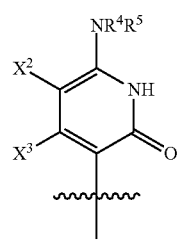  (BP)
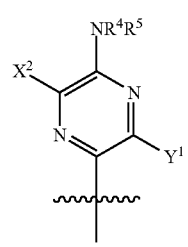  (BQ)
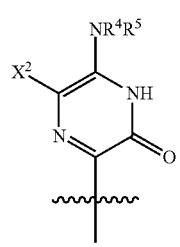  (BR)
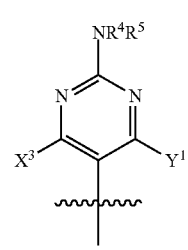  (BS)
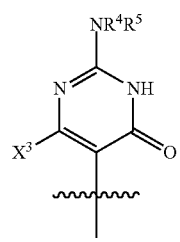  (BT)
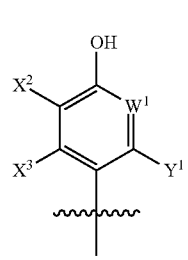  (BU)
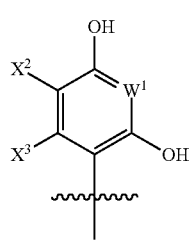  (BV)
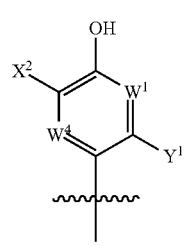  (BW)
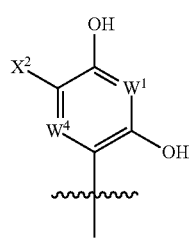  (BX)
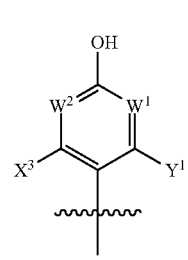  (BY)
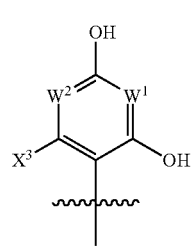  (BZ)
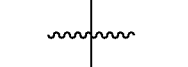  (BAA)

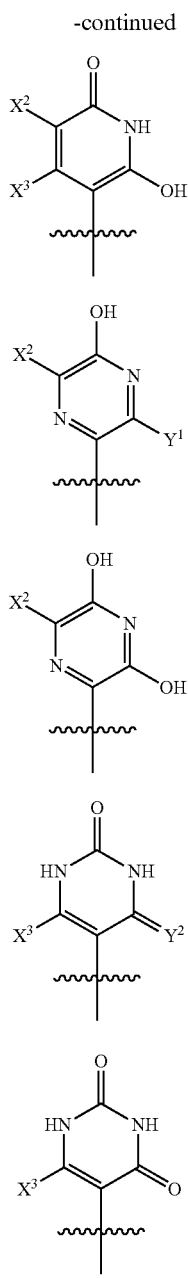

$R^1$, $R^2$, $R^3$, $R^4$, and $R^5$, are as defined above;

each $W^1$, $W^2$, $W^3$ and $W^4$ is independently N, CH, CF, Cl, CBr, CCl, CCN, CCH$_3$, CCF$_3$, CCH$_2$CH$_3$, CC(O)NH$_2$, CC(O)NHR$^4$, CC(O)N(R$^4$)$_2$, CC(O)OH, CC(O)OR$^4$ or CX$^3$;

each W* is independently O, S, NH or NR$^4$;

X is O, S, SO$_2$, CH$_2$, CH$_2$OH, CHF, CF$_2$, C(Y$^3$)$_2$, CHCN, C(CN)$_2$, CHR$^4$ or C(R$^4$)$_2$;

X* is CH, CF, CY$^3$ or CR$^4$;

$X^2$ is H, straight chained, branched or cyclic optionally substituted alkyl, CH$_3$, CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, CH$_2$OH, optionally substituted alkenyl, optionally substituted alkynyl, COOH, COOR$^4$, COO-alkyl, COO-aryl, CO—Oalkoxyalkyl, CONH$_2$, CONHR$^4$, CON(R$^4$)$_2$, chloro, bromo, fluoro, iodo, CN, N$_3$, OH, OR$^4$, NH$_2$, NHR$^4$, NR$^4$R$^5$, SH or SR$^5$;

each $X^3$ is independently a straight chained, branched or cyclic optionally substituted alkyl (including lower alkyl), CH$_3$, CH$_2$CN, CH$_2$N$_3$, CH$_2$NH$_2$, CH$_2$NHCH$_3$, CH$_2$N(CH$_3$)$_2$, CH$_2$OH, halogenated alkyl (including halogenated lower alkyl), CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, N$_3$, CN, —C(O)OH, —C(O)OR$^4$, —C(O)O (lower alkyl), —C(O)NH$_2$, —C(O)NHR$^4$, —C(O)NH(lower alkyl), —C(O)N(R$^4$)$_2$, —C(O)N(lower alkyl)$_2$, OH, OR$^4$, —O(acyl), —O(lower acyl), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), chloro, bromo, fluoro, iodo, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), —N(acyl)$_2$;

each Y is independently selected from the group consisting of H, optionally substituted lower alkyl, cycloalkyl, alkenyl, alkynyl, CH$_2$OH, CH$_2$NH$_2$, CH$_2$NHCH$_3$, CH$_2$N(CH$_3$)$_2$, CH$_2$F, CH$_2$Cl, CH$_2$N$_3$, CH$_2$CN, CH$_2$CF$_3$, CF$_3$, CF$_2$CF$_3$, CH$_2$CO$_2$R, (CH$_2$)$_m$COOH, (CH$_2$)$_m$COOR, (CH$_2$)$_m$CONH$_2$, (CH$_2$)$_m$CONR$_2$, and (CH$_2$)$_m$CONHR;

wherein R is H, alkyl or acyl;

$Y^1$ is hydrogen, bromo, chloro, fluoro, iodo, CN, OH, OR$^4$, NH$_2$, NHR$^4$, NR$^4$R$^5$, SH or SR$^4$;

each $Y^2$ is independently O, S, NH or NR$^4$;

each $Y^3$ is independently H, F, Cl, Br or I;

wherein for Base (B), $W^4$ cannot be CH if $W^1$, $W^2$ and $W^3$ are N;

wherein for Base (E), (F), (K), (L), (W) and (X), $W^4$ cannot be CH if $W^1$ is N;

each $R^6$ is independently an optionally substituted alkyl (including lower alkyl), CH$_3$, CH$_2$CN, CH$_2$N$_3$, CH$_2$NH$_2$, CH$_2$NHCH$_3$, CH$_2$N(CH$_3$)$_2$, CH$_2$OH, halogenated alkyl (including halogenated lower alkyl), CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, —CH$_2$C(O)OH, —CH$_2$C(O)OR$^4$, —CH$_2$C(O)O(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)NH$_2$, —C(O)NHR$^4$, —C(O)NH(lower alkyl), —C(O)N(R$^4$)$_2$, —C(O)N(lower alkyl)$_2$ or cyano;

each $R^7$ is independently OH, OR$^2$, optionally substituted alkyl (including lower alkyl), CH$_3$, CH$_2$CN, CH$_2$N$_3$, CH$_2$NH$_2$, CH$_2$NHCH$_3$, CH$_2$N(CH$_3$)$_2$, CH$_2$OH, halogenated alkyl (including halogenated lower alkyl), CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, optionally substituted carbocycle (preferably a 3-7 membered carbocyclic ring), optionally substituted heterocycle (preferably a 3-7 membered heterocyclic ring having one or more O, S and/or N), optionally substituted heteroaryl (preferably a 3-7 membered heteroaromatic ring having one or more O, S and/or N), —CH$_2$C(O)OH, —CH$_2$C(O)OR$^4$, —CH$_2$C(O)O(lower alkyl), —CH$_2$C(O)SH, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O (lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), —N(acyl)$_2$, azido, cyano, SCN, OCN, NCO or halo (fluoro, chloro, bromo, iodo);

alternatively, R$^6$ and R$^7$ can come together to form a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N); and each m is independently 0, 1 or 2.

In a fourth principal embodiment, a compound of Formula (VI) or (VII), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (VI) or (VII):

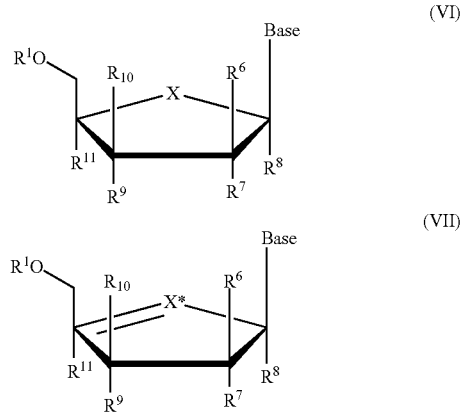

or a pharmaceutically acceptable salt or prodrug, or a stereoisomeric, tautomeric or polymorphic form thereof, wherein: Base, R, R$^1$, R$^2$, R$^3$, R$^4$, R$^5$, R$^6$, R$^7$, Y, Y$^1$, Y$^2$, Y$^3$, W$^1$, W$^2$, W$^3$, W$^4$, W*, X, X*, X$^1$, X$^2$, and X$^3$ are as defined above;

wherein, in one embodiment, R$^8$ in Formula (VI) is —OH or —NH$_2$ only when X is carbon; and wherein;

each R$^8$ and R$^{11}$ is independently hydrogen, an optionally substituted alkyl (including lower alkyl), CH$_3$, CH$_2$CN, CH$_2$N$_3$, CH$_2$NH$_2$, CH$_2$NHCH$_3$, CH$_2$N(CH$_3$)$_2$, CH$_2$OH, halogenated alkyl (including halogenated lower alkyl), CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, —CH$_2$C(O)OH, —CH$_2$C(O)OR$^4$, —CH$_2$C(O)O(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)NH$_2$, —(CH$_2$)$_m$C(O)NHR$^4$, —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)NH$_2$, —C(O)NHR$^4$, —C(O)NHR$^4$,
—C(O)NH(lower alkyl), —C(O)N(R$^4$)$_2$, —C(O)N(lower alkyl)$_2$, cyano, NH-acyl or N(acyl)$_2$;

each R$^9$ and R$^{10}$ are independently hydrogen, OH, OR$^2$, optionally substituted alkyl (including lower alkyl), CH$_3$, CH$_2$CN, CH$_2$N$_3$, CH$_2$NH$_2$, CH$_2$NHCH$_3$, CH$_2$N(CH$_3$)$_2$, CH$_2$OH, halogenated alkyl (including halogenated lower alkyl), CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, optionally substituted carbocycle (preferably a 3-7 membered carbocyclic ring), optionally substituted heterocycle (preferably a 3-7 membered heterocyclic ring having one or more O, S and/or N), optionally substituted heteroaryl (preferably a 3-7 membered heteroaromatic ring having one or more O, S and/or N), —CH$_2$C(O)OH, —CH$_2$C(O)OR$^4$, —CH$_2$C(O)O(lower alkyl), —CH$_2$C(O)SH, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), —N(acyl)$_2$, azido, cyano, SCN, OCN, NCO or halo (fluoro, chloro, bromo, iodo);

each m is independently 0, 1 or 2; and alternatively, R$^6$ and R$^{10}$, R$^7$ and R$^9$, R$^8$ and R$^7$ or R$^9$ and R$^{11}$ can come together to form a bridged compound selected from the group consisting of optionally substituted carbocycle (preferably a 3-7 membered carbocyclic ring) or optionally substituted heterocycle (preferably a 3-7 membered heterocyclic ring having one or more O, S and/or N); or alternatively, R$^6$ and R$^7$ or R$^9$ and R$^{10}$ can come together to form a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N).

In a fifth principal embodiment, a compound of Formula (VIII), (IX) or (X), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (VIII), (IX) or (X):

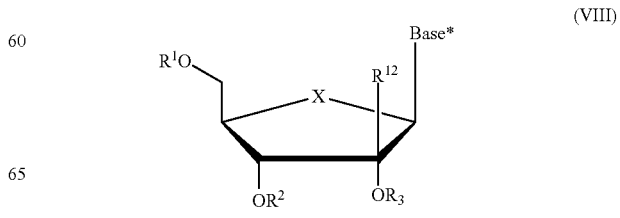

-continued

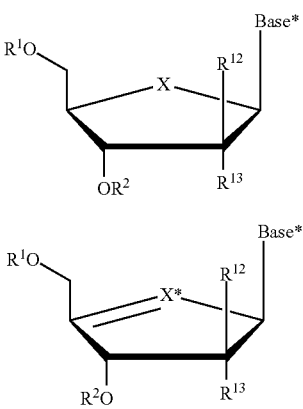

(IX)

(X)

or a pharmaceutically acceptable salt or prodrug, or a stereoisomeric, tautomeric or polymorphic form thereof, wherein:
$R^1$, $R^2$, $R^3$, $R^4$, $R^5$, X, $Y^3$, and X* are as defined above;
Base* is a purine or pyrimidine base as defined herein;
each $R^{12}$ is independently a substituted alkyl (including lower alkyl), $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, substituted alkenyl, haloalkenyl (but not Br-vinyl), substituted alkynyl, haloalkynyl, —$CH_2C(O)OH$, —$CH_2C(O)OR^4$, —$CH_2C(O)O$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —$C(O)OH$, —$C(O)OR^4$, —$C(O)NH_2$, —$C(O)NHR^4$, —$C(O)NH$(lower alkyl), —$C(O)N(R^4)_2$, —$C(O)N$(lower alkyl)$_2$;
each $R^{13}$ is independently substituted alkyl (including lower alkyl), $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, substituted alkenyl, haloalkenyl (but not Br-vinyl), substituted alkynyl, haloalkynyl, optionally substituted carbocycle (preferably a 3-7 membered carbocyclic ring), optionally substituted heterocycle (preferably a 3-7 membered heterocyclic ring having one or more O, S and/or N), optionally substituted heteroaryl (preferably a 3-7 membered heteroaromatic ring having one or more O, S and/or N), —$CH_2C(O)OH$, —$CH_2C(O)OR^4$, —$CH_2C(O)O$(lower alkyl), —$CH_2C(O)SH$, —$CH_2C(O)SR^4$, —$CH_2C(O)S$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)SH$, —$(CH_2)_mC(O)SR^4$, —$(CH_2)_mC(O)S$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —$C(O)OH$, —$C(O)OR^4$, —$C(O)SH$, —$C(O)SR^4$, —$C(O)S$(lower alkyl), —$C(O)NH_2$, —$C(O)NHR^4$, —$C(O)NH$(lower alkyl), —$C(O)N(R^4)_2$, —$C(O)N$(lower alkyl)$_2$, —$O(R^4)$, —$O$(alkynyl), —$O$(aralkyl), —$O$(cycloalkyl), —$S$(acyl), —$S$(lower acyl), —$S(R^4)$, —$S$(lower alkyl), —$S$(alkenyl), —$S$(alkynyl), —$S$(aralkyl), —$S$(cycloalkyl), —$NHR^4$, —$NR^4R^5$, —$NH$(alkenyl), —$NH$(alkynyl), —$NH$(aralkyl), —$NH$(cycloalkyl), SCN, OCN, NCO or fluoro;

alternatively, $R^{12}$ and $R^{13}$ can come together to form a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N); and
each m is independently 0, 1 or 2.
In a sixth principal embodiment, a compound of Formula (XI) or (XII), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (XI) or (XII):

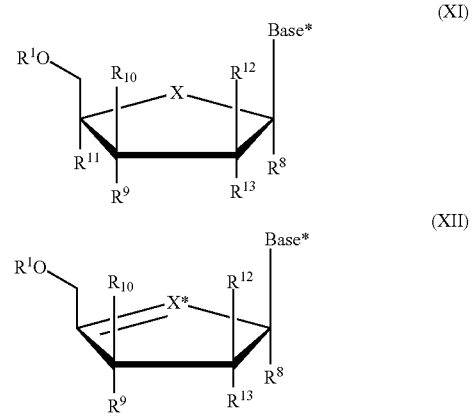

(XI)

(XII)

or a pharmaceutically acceptable salt or prodrug, or a stereoisomeric, tautomeric or polymorphic form thereof, wherein:
alternatively, Base*, is replaced with Base in Formulas (XI) and (XII); and
Base, Base*, R, $R^1$, $R^2$, $R^3$, $R^4$, $R^5$, $R^{12}$, $R^{13}$, Y, $Y^1$, $Y^2$, $Y^3$, W*, $W^1$, $W^2$, $W^3$, X, X*, $X^1$, $X^2$, and $X^3$ are as defined above;
wherein, in one embodiment, $R^8$ in Formula (XI) is —OH or —$NH_2$ only when X is carbon; and
wherein;
each $R^8$ and $R^{11}$ is independently hydrogen, an optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, —$CH_2C(O)OH$, —$CH_2C(O)OR^4$, —$CH_2C(O)O$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —$C(O)OH$, —$C(O)OR^4$, —$C(O)O$(lower alkyl), —$C(O)NH_2$, —$C(O)NHR^4$, —$C(O)NH$(lower alkyl), —$C(O)N(R^4)_2$, —$C(O)N$(lower alkyl)$_2$, cyano, NH-acyl or N(acyl)$_2$;
each $R^9$ and $R^{10}$ are independently hydrogen, OH, $OR^2$, optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, optionally substituted carbocycle (preferably a 3-7 membered carbocyclic ring), optionally substituted heterocycle (preferably a 3-7 membered heterocyclic ring having one or more O, S and/or N), optionally substituted heteroaryl (preferably a 3-7 membered heteroaromatic ring having one or more O, S and/or N), —CH$_2$C(O)OH, —CH$_2$C(O)OR$^4$, —CH$_2$C(O)O(lower alkyl), —CH$_2$C(O)SJI, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), —N(acyl)$_2$, azido, cyano, SCN, OCN, NCO or halo (fluoro, chloro, bromo, iodo);

each m is independently 0, 1 or 2; and alternatively, R$^8$ and R$^{13}$, R$^9$ and R$^{13}$, R$^9$ and R$^{11}$ or R$^{10}$ and R$^{12}$ can come together to form a bridged compound selected from the group consisting of optionally substituted carbocycle (preferably a 3-7 membered carbocyclic ring) or optionally substituted heterocycle (preferably a 3-7 membered heterocyclic ring having one or more O, S and/or N); or alternatively, R$^{12}$ and R$^{13}$ or R$^9$ and R$^{10}$ can come together to form a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N).

In a particular aspect of the invention, a compound of Formula (XI) or (XII), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (XI) or (XII):

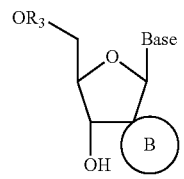

(XIII)

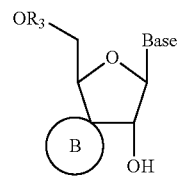

(XIV)

or a pharmaceutically acceptable salt or prodrug, or a stereoisomeric, tautomeric or polymorphic form thereof, wherein:
R$^3$ is selected from the group consisting of H; mono-, di-, and tri-phosphate or a stabilized phosphate prodrug; acyl; a sulfonate ester; optionally substituted alkyl sulfonyl; optionally substituted arylsulfonyl; a lipid; an amino acid; a carbohydrate; a peptide; cholesterol; and a pharmaceutically acceptable leaving group which when administered in vivo is capable of providing a compound wherein R$_3$ is independently H, or mono-, di- or triphosphate;

X$^{11}$ is selected from the group consisting of one or more O, S, SO, SO$_2$, N, NH, NR and CH$_2$ wherein any of the aforementioned may be optionally substituted and may be variably positioned so as to form a 3-7 membered ring;

R is H, alkyl or acyl; and

B indicates a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N);

Base is selected from the group consisting of

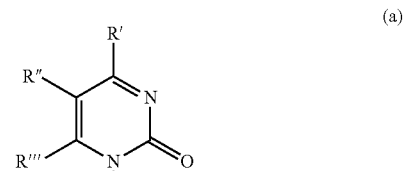

(a)

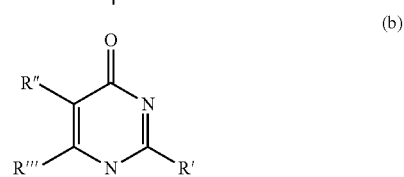

(b)

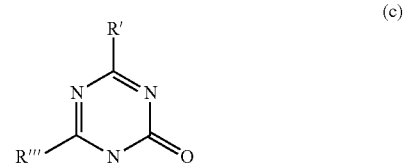

(c)

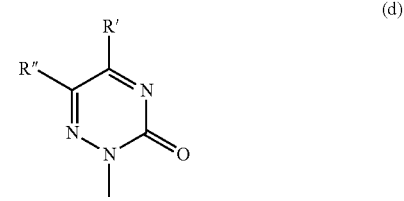

(d)

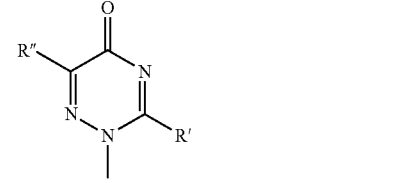

(e)

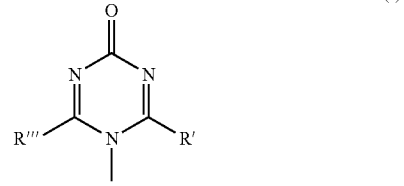

(f)

-continued

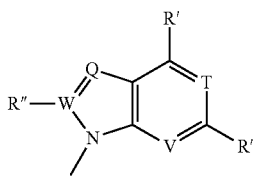
(g)

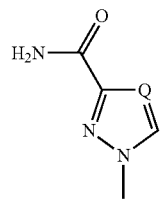
(h)

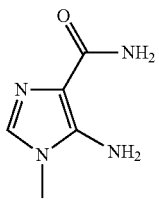
(i)

and

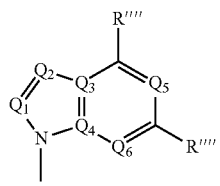
(j)

wherein:
each R', R", R'" and R"" are independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$ and $(CH_2)_mCONH_2$;

m is 0 or 1;

W is C—R" or N;

T and V independently are CH or N;

Q is CH, —CCl, —CBr, —CF, —CI, —CCN, —C—COOH, —C—$CONH_2$, or N;

$Q_1$ and $Q_2$ independently are N or C—R;

$Q_3$, $Q_4$, $Q_5$ and $Q_6$ independently are N or CH; and tautomeric forms thereof.

In a second particular aspect of the invention, a compound of Formula (XV), (XVI) or (XVII), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (XV), (XVI) or (XVII):

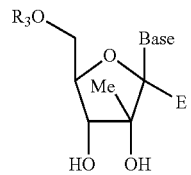
(XV)

(XVI)

or (XVII)

or its pharmaceutically acceptable salt or prodrug, or a stereoisomeric, tautomeric or polymorphic form thereof, wherein:
G and E independently are selected from the group consisting of $CH_3$, $CH_2OH$, $CH_2F$, $CH_2N_3$, $CH_2CN$, $(CH_2)_mCOOH$, $(CH_2)_mCOOR$, $(CH_2)_mCONH_2$, $(CH_2)_mCONR_2$, $(CH_2)_mCONHR$ and N-acyl;

m is 0 or 1;

R is H, alkyl or acyl; and

R', R", R'", R"", and $R^3$ and Base are as defined for Formula (XIII).

Alternatively, for compound of Formula (XVII), at most one of G and E can further be hydrogen.

In a third particular aspect of the invention, a compound of Formula (XVIII) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (XVIII):

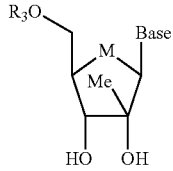
(XVIII)

or its pharmaceutically acceptable salt or prodrug, or a stereoisomeric, tautomeric or polymorphic form thereof, wherein M is selected from the group consisting of S, SO, and $SO_2$; and R', R", R'", R"", and $R_3$ and Base are as defined for Formula (XIII).

In a fourth particular aspect of the invention, a compound of Formula (XIX), (XX), (XXI) (XXII) or (XXIII) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (XIX), (XX), (XXI) (XXII) or (XXIII):

(XIX)

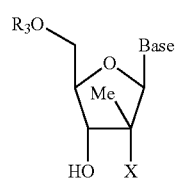

(XX)

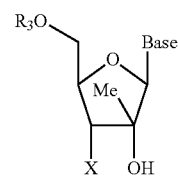

(XXI)

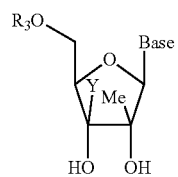

(XXII)

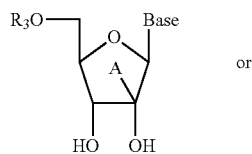

or (XXIII)

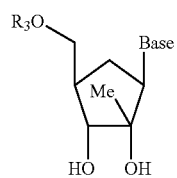

or its pharmaceutically acceptable salt or prodrug, or a stereoisomeric, tautomeric or polymorphic form thereof wherein:

A is selected from the group consisting of optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mCOOH$, $(CH_2)_mCOOR$, $(CH_2)_mCO-NH_2$, $(CH_2)_mCONR_2$, and $(CH_2)_mCONHR$;

Y is selected from the group consisting of H, optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mCOOH$, $(CH_2)_mCOOR$, $(CH_2)_mCONH_2$, $(CH_2)_mCONR_2$, and $(CH_2)_mCONHR$;

X is selected from the group consisting of —OH, optionally substituted alkyl, cycloalkyl, alkenyl, alkynyl, —O-alkyl, —O-alkenyl, —O-alkynyl, —O-aryl, —O-aralkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aryl, NH-aralkyl, NH-cycloalkyl, SH, S-alkyl, S-alkenyl, S-alkynyl, S-aryl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mCOOH$, $(CH_2)_mCOOR$, $(CH_2)_mCONH_2$, $(CH_2)_mCONR_2$, $(CH_2)_mCONHR$, an optionally substituted 3-7 membered carbocyclic, and an optionally substituted 3-7 membered heterocyclic ring having O, S and/or N independently as a heteroatom taken alone or in combination;

m is 0 or 1;

R is H, alkyl or acyl;

$R_3$ is selected from the group consisting of H; mono-, di-, and tri-phosphate or a stabilized phosphate prodrug; substituted or unsubstituted alkyl; acyl; a sulfonate ester, optionally substituted alkyl sulfonyl; optionally substituted arylsulfonyl; a lipid; an amino acid; a carbohydrate; a peptide; cholesterol; and a pharmaceutically acceptable leaving group which when administered in vivo is capable of providing a compound wherein $R_3$ is independently H, or mono-, di- or triphosphate; and Base is a non-natural base selected from the group of:

(a)

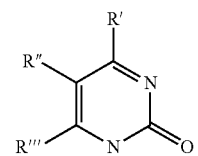

(b)

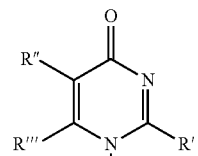

(c)

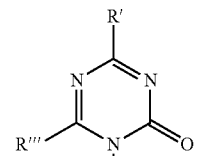

(d)

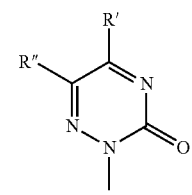

(e)

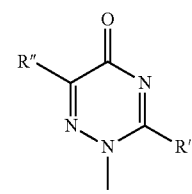

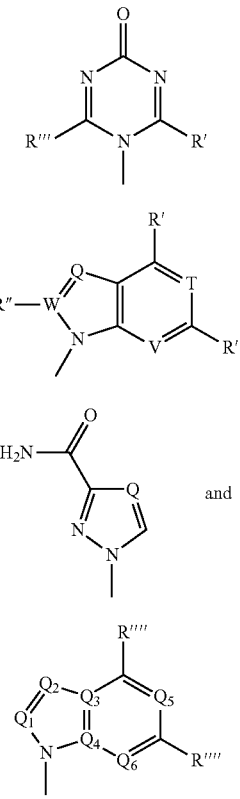

or (i) herein below
  wherein:
    each R', R", R'" and R"" is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$ and $(CH_2)_mCONH_2$;
    m is 0 or 1;
    W is C—R" or N;
    T and V independently are CH or N;
    Q is CH, —CCl, —CBr, —CF, —CI, —CCN, —C—COOH, —C—$CONH_2$, or N;
    $Q_1$ and $Q_2$ independently are N or C—R""; and
    $Q_3$, $Q_4$, $Q_5$ and $Q_6$ independently are N or CH;
    with the proviso that in bases (g) and (i), R', R"" are not H, OH, or $NH_2$; and Q, T, V, $Q_2$, $Q_5$ and $Q_6$ are not N.

In one embodiment, the amino acid residue is of the formula $C(O)C(R^{11})(R^{12})(NR^{13}R^{14})$, wherein:
$R^{11}$ is the side chain of an amino acid and wherein, as in proline, $R^{11}$ can optionally be attached to $R^{13}$ to form a ring structure; or alternatively, $R^{11}$ is an alkyl, aryl, heteroaryl or heterocyclic moiety;
$R^{12}$ is hydrogen, alkyl (including lower alkyl) or aryl; and
$R^{13}$ and $R^{14}$ are independently hydrogen, acyl (including an acyl derivative attached to $R^{11}$) or alkyl (including but not limited to methyl, ethyl, propyl, and cyclopropyl).

In another preferred embodiment, at least one of $R^2$ and $R^3$ is an amino acid residue, and is preferably L-valinyl.

The β-D- and β-L-nucleosides of this invention may inhibit Flaviviridae polymerase activity. Nucleosides can be screened for their ability to inhibit Flaviviridae polymerase activity in vitro according to screening methods set forth more particularly herein. One can readily determine the spectrum of activity by evaluating the compound in the assays described herein or with another confirmatory assay.

In one embodiment the efficacy of the anti-Flaviviridae compound is measured according to the concentration of compound necessary to reduce the plaque number of the virus in vitro, according to methods set forth more particularly herein, by 50% (i.e. the compound's $EC_{50}$). In preferred embodiments the parent of the prodrug compound exhibits an $EC_{50}$ of less than 25, 15, 10, 5, or 1 micromolar. In preferred embodiments the compound exhibits an $EC_{50}$ of less than 15 or 10 micromolar, when measured according to the polymerase assay described in Ferrari et al., *Jnl. of Vir.*, 73:1649-1654, 1999; Ishii et al, *Hepatology*, 29:1227-1235, 1999; Lohmann et al., *Jnl. of Bio. Chem.*, 274:10807-10815, 1999; or Yamashita et al, *Jnl. of Bio. Chem.*, 273:15479-15486, 1998.

In another embodiment, combination and/or alternation therapy are provided. In combination therapy, an effective dosage of two or more agents are administered together, whereas during alternation therapy an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The invention provides combinations of at least two of the herein described prodrugs. The invention further provides at least one of the described 2' and 3'-prodrugs in combination or alternation with a second nucleoside that exhibits activity against a Flaviviridae, including but not limited to a parent drug of any of the prodrugs defined herein, i.e. β-D-2',6-dimethyl-cytidine, β-D-2',6-dimethyl-thymidine, β-D-2',8-dimethyl-adenosine, β-D-2',8-dimethyl-guanosine, β-D-2',6-dimethyl-5-fluorocytidine and/or β-D-2',6-dimethyl-uridine. Alternatively, the 2' or 3'-prodrugs can be administered in combination or alternation with other anti-Flaviviridae agent exhibits an $EC_{50}$ of less than 10 or 15 micromolar, or their prodrugs or pharmaceutically acceptable salts.

Nonlimiting examples of antiviral agents that can be used in combination with the compounds disclosed herein include: 1) an interferon and/or ribavirin; (2) Substrate-based NS3 protease inhibitors; (3) Non-substrate-based inhibitors; (4) Thiazolidine derivatives; (5) Thiazolidines and benzanilides; (6) A phenan-threnequinone; (7) NS3 inhibitors; (8) HCV helicase inhibitors; (9) polymerase inhibitors, including RNA-dependent RNA-polymerase inhibitors; (10) Antisense oligodeoxynucleotides; (11) Inhibitors of IRES-dependent translation; (12) Nuclease-resistant ribozymes; and (13) other compounds that exhibit activity against a flaviviridae. The invention further includes administering the prodrug in combination or alternation with an immune modulator or other pharmaceutically active modifier of viral replication, including a biological material such as a protein, peptide, oligonucleotide, or gamma globulin, including but not limited to interfereon, interleukin, or an antisense oligonucleotides to genes which express or regulate Flaviviridae replication.

The invention further includes administering the prodrug in combination or alternation with an immune modulator or other pharmaceutically active modifer of viral replication, including a biological material such as a protein, peptide, oligonucleotide, or gamma globulin, including but not limited to interfereon, interleukin, or an antisense oligonucleotides to genes which express or regulate Flaviviridae replication.

In particular, the present invention provides the following:
(a) a compound of Formula (XIII)-(XXIII), or its pharmaceutically acceptable salt or prodrug thereof;
(b) pharmaceutical compositions comprising a compound of Formula (XIII)-(XXIII), or its pharmaceutically acceptable salt or prodrug thereof, together with a pharmaceutically acceptable carrier or dileuent;
(c) pharmaceutical compositions comprising a compound of Formula (XIII)-(XXIII), or its pharmaceutically acceptable salt or prodrug thereof, with one or more other effective antiviral agent, optionally with a pharmaceutically acceptable carrier or dileuent;
(d) pharmaceutical compositions for the treatment of a Flaviviridae infection in a host comprising a compound of Formula (I)-(XXIII), or its pharmaceutically acceptable salt or prodrug thereof, together with a pharmaceutically acceptable carrier or dileuent;
(e) pharmaceutical compositions for the treatment of a Flaviviridae infection in a host comprising a compound of Formula (I)-(XXIII), or its pharmaceutically acceptable salt or prodrug thereof, with one or more other effective antiviral agent, optionally with a pharmaceutically acceptable carrier or dileuent;
(f) methods for the treatment of a Flaviviridae infection in a host comprising a compound of Formula (I)-(XXIII), or its pharmaceutically acceptable salt or prodrug thereof, optionally with a pharmaceutically acceptable carrier or dileuent;
(g) methods for the treatment of a Flaviviridae infection in a host comprising a compound of Formula (I)-(XXIII), or its pharmaceutically acceptable salt or prodrug thereof, with one or more other effective antiviral agent, optionally with a pharmaceutically acceptable carrier or dileuent;
(h) uses for a compound of Formula (I)-(XXIII), or its pharmaceutically acceptable salt or prodrug thereof, optionally with a pharmaceutically acceptable carrier or dileuent, for the treatment of a Flaviviridae infection in a host;
(i) uses for a compound of Formula (I)-(XXIII), or its pharmaceutically acceptable salt or prodrug thereof, with one or more other effective antiviral agent, optionally with a pharmaceutically acceptable carrier or dileuent, for the treatment of a Flaviviridae infection in a host;
(j) uses for a compound of Formula (I)-(XXIII), or its pharmaceutically acceptable salt or prodrug thereof, optionally with a pharmaceutically acceptable carrier or dileuent, in the manufacture of a medicament for the treatment of a Flaviviridae infection in a host; and
(k) uses for a compound of Formula (I)-(XXIII), or its pharmaceutically acceptable salt or prodrug thereof, with one or more other effective antiviral agent, optionally with a pharmaceutically acceptable carrier or dileuent, in the manufacture of a medicament for the treatment of a Flaviviridae infection in a host.

In an alternative embodiment, the parent nucleoside compound of any of the 2'- or 3'-prodrugs (i.e., the nucleosides without the 2'- or 3'-cleavable moieties) are provided for the treatment of a Flaviviridae infection and in particular a hepatitis C infection.

DETAILED DESCRIPTION OF THE INVENTION

Figure 1:
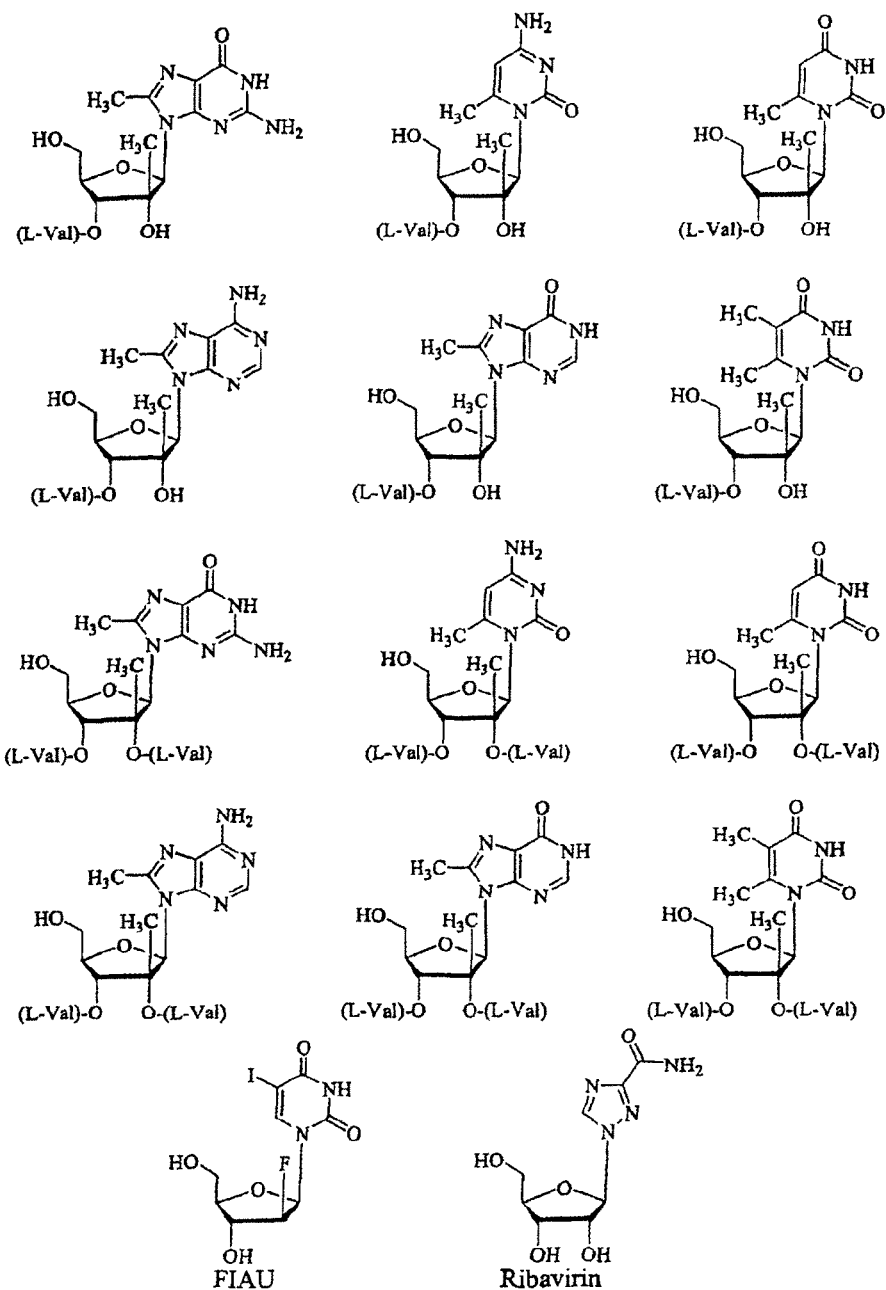
FIG. 1 provides the structure of various non-limiting examples of nucleosides of the present invention, as well as other known nucleosides, in particular FIAU and ribavirin.

The invention as disclosed herein is a compound, a method and composition for the treatment of a Flaviviridae infection in humans and other host animals. The method includes the administration of an effective anti-Flaviviridae treatment amount of a 2' and/or 3'-prodrug of a 1', 2', 3' or 4'-branched β-D or β-L nucleoside as described herein or a pharmaceutically acceptable salt, derivative or prodrug thereof, optionally in a pharmaceutically acceptable carrier. The compounds of this invention either possesses antiviral (i.e., anti-HCV) activity, or are metabolized to a compound that exhibits such activity. HCV is a member of the Flaviviridae family. HCV has been placed in a new monotypic genus, hepacivirus. Therefore, in one embodiment, the Flaviviridae is HCV. In an alternate embodiment, the Flaviviridae is a flavivirus or pestivirus.

The 2' and/or 3'-prodrugs of a 1', 2', 3' or 4'-branched β-D or β-L nucleoside are acyl derivates of a secondary or tertiary alcohol alpha to a secondary or tertiary carbon. Due to the steric hindrance of these prodrugs over the 5'-prodrugs, an acyl derivative of a primary alcohol, these prodrugs differentially modulate the biological properties of the molecule in vivo. It has been discovered that the 2' and/or 3'-prodrugs of a 1', 2', 3' or 4'-branched β-D or β-L nucleoside can provide a drug with increased half-life and improved pharmacokinetic profile.

The 2' or 3'-prodrug in a preferred embodiment is a cleavable acyl group, and most particularly, an amino acid moiety, prepared from any naturally occurring and synthetic α, β γ or δ amino acid, including but is not limited to, glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, (3-leucinyl, β-isoleuccinyl, β-prolinyl, β-phenylalaninyl, β-tryptophanyl, β-methioninyl, 13-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. In one particular, embodiment, the moiety is a valine ester. On particularly preferred compound is the 3'-valine ester of 2',6-dimethyl-ribo-cytidine.

The oral bio-availability of 1', 2', 3' or 4'-branched β-D or β-L nucleoside as the neutral base and the HCl salt is low in rodents and non-human primates. It has been discovered that there is significant competition of 1', 2', 3' or 4'-branched β-D or β-L nucleoside with other nucleosides or nucleoside analogs for absorption, or transport, from the gastrointestinal tract and competition of other nucleosides or nucleoside analogs for the absorption with 1', 2', 3' or 4'-branched β-D or β-L nucleoside. In order to improve oral bioavailability and reduce the potential for drug-drug interaction, 2' and 3'-prodrugs of 1', 2', 3' or 4'-branched β-D or β-L nucleoside were obtained with higher oral bioavailability than the parent molecule and a reduced effect on the bioavailability of other nucleosides or nucleoside analogs used in combination.

The 2', 3', and/or 5'-mono, di or trivaline ester of a 1', 2', 3' or 4'-branched β-D or β-L nucleoside have higher oral bioavailability than the parent 1', 2', 3' or 4'-branched β-D or β-L nucleoside and reduced interaction with other nucleosides or nucleoside analogs when used in combination as compared to 1', 2', 3' or 4'-branched β-D or β-L nucleoside.

The 2', 3', and/or 5'-mono, di or trivaline ester of a 1', 2', 3' or 4'-branched β-D or β-L nucleoside can be converted to the parent 1', 2', 3' or 4'-branched β-D or β-L nucleoside through de-esterification in the gastrointestinal mucosa, blood or liver. The 2', 3', and/or 5'-mono, di or trivaline ester of a 1', 2', 3' or 4'-branched β-D or β-L nucleoside can be actively transported from the gastrointestinal lumen after oral delivery into the bloodstream by an amino acid transporter function in the mucosa of the gastrointestinal tract. This accounts for the increase in oral bioavailability compared to the parent 1', 2', 3' or 4'-branched β-D or β-L nucleoside that is transported primarily by a nucleoside transporter function. There is also reduced competition for uptake of the 2', 3', and/or 5'-mono, di or trivaline ester of 1', 2', 3' or 4'-branched β-D or β-L nucleoside with other nucleosides or nucleoside analogs that are transported by the nucleoside transporter function and not the amino acid transporter function. As partial de-esterification of the di or trivaline ester of 1', 2', 3' or 4'-branched β-D or β-L nucleoside occurs prior to complete absorption, the mono or divaline ester continues to be absorbed using the amino acid transporter function. Therefore, the desired outcome of better absorption, or bioavailability, and reduced competition with other nucleosides or nucleoside analogs for uptake into the bloodstream can be maintained.

In summary, the present invention includes the following features:

(a) a 2' and/or 3'-prodrug of a 1', 2', 3' or 4'-branched β-D or β-L nucleoside, as described herein, and pharmaceutically acceptable salts and compositions thereof;

(b) a 2' and/or 3'-prodrug of a 1', 2', 3' or 4'-branched β-D or β-L nucleoside as described herein, and pharmaceutically acceptable salts and compositions thereof for use in the treatment and/or prophylaxis of a Flaviviridae infection, especially in individuals diagnosed as having a Flaviviridae infection or being at risk of becoming infected by hepatitis C;

(c) a 2' and/or 3'-prodrug of a 1', 2', 3' or 4'-branched β-D or β-L nucleoside, or their pharmaceutically acceptable salts and compositions as described herein substantially in the absence of the opposite enantiomers of the described nucleoside, or substantially isolated from other chemical entities;

(d) processes for the preparation of a 2' and/or 3'-prodrug of a 1', 2', 3' or 4'-branched β-D or β-L nucleoside, as described in more detail below;

(e) pharmaceutical formulations comprising a 2' and/or 3'-prodrug of a 1', 2', 3' or 4'-branched β-D or β-L nucleoside or a pharmaceutically acceptable salt thereof together with a pharmaceutically acceptable carrier or diluent;

(f) pharmaceutical formulations comprising a 2' and/or 3'-prodrug of a 1', 2',3' or 4'-branched β-D or β-L nucleoside or a pharmaceutically acceptable salt thereof together with one or more other effective anti-HCV agents, optionally in a pharmaceutically acceptable carrier or diluent;

(g) pharmaceutical formulations comprising a 2' and/or 3'-prodrug of a 1', 2', 3' or 4'-branched β-D or β-L nucleoside or a pharmaceutically acceptable salt thereof together with the parent of a different a 1', 2', 3' or 4'-branched β-D or β-L nucleoside, optionally in a pharmaceutically acceptable carrier or diluent;

(h) a method for the treatment and/or prophylaxis of a host infected with Flaviviridae that includes the administration of an effective amount of a 2' and/or 3'-prodrug of a 1', 2', 3' or 4'-branched β-D or β-L nucleoside, its pharmaceutically acceptable salt or composition;

(i) a method for the treatment and/or prophylaxis of a host infected with Flaviviridae that includes the administration of an effective amount of a 2' and/or 3'-prodrug of a 1', 2', 3' or 4'-branched β-D or β-L nucleoside, its pharmaceutically acceptable salt or composition in combination and/or alternation with one or more effective anti-HCV agent;

(j) a method for the treatment and/or prophylaxis of a host infected with Flaviviridae that includes the administration of an effective amount of a 2' and/or 3'-prodrug of a 1', 2', 3' or 4'-branched β-D or β-L nucleoside, or its pharmaceutically acceptable salt or composition with the parent of a different a 1', 2', 3' or 4'-branched β-D or β-L nucleoside;

(k) a method for the treatment and/or prophylaxis of a host infected with Flaviviridae that includes the administration of an effective amount of a 2' and/or 3'''-prodrug of a β-D-2'-methyl-cytidine, or its pharmaceutically acceptable salt or composition thereof;

(l) a method for the treatment and/or prophylaxis of a host infected with Flaviviridae that includes the administration of an effective amount of the 2'-valyl or acetyl ester of β-D-2'-methyl-cytidine, or its pharmaceutically acceptable salt or composition thereof;

(m) use of a 2' and/or 3'-prodrug of a 1', 2', 3' or 4'-branched β-D or β-L nucleoside, and pharmaceutically acceptable salts and compositions thereof for the treatment and/or prophylaxis of a Flaviviridae infection in a host;

(n) use of a 2' and/or 3'-prodrug of a 1', 2', 3' or 4'-branched β-D or β-L nucleoside, its pharmaceutically acceptable salt or composition in combination and/or alternation with one or more effective anti-HCV agent for the treatment and/or prophylaxis of a Flaviviridae infection in a host;

(o) use of a 2' and/or 3'-prodrug of a 1', 2', 3' or 4'-branched β-D or β-L nucleoside, or its pharmaceutically acceptable salt or composition with the parent of a different a 1', 2', 3' or 4'-branched β-D or β-L nucleoside for the treatment and/or prophylaxis of a Flaviviridae infection in a host;

(p) use of a 2' and/or 3'-prodrug of a β-D-2'-methyl-cytidine, or its pharmaceutically acceptable salt or composition thereof for the treatment and/or prophylaxis of a Flaviviridae infection in a host;

(q) use of the 3'-valyl or acetyl ester of β-D-2'-methyl-cytidine, or its pharmaceutically acceptable salt or composition thereof for the treatment and/or prophylaxis of a Flaviviridae infection in a host;

(r) use of a 2' and/or 3'-prodrug of a 1', 2', 3' or 4'-branched β-D or β-L nucleoside, and pharmaceutically acceptable salts and compositions thereof in the manufacture of a medicament for treatment and/or prophylaxis of a Flaviviridae infection;

(s) use of a 2' and/or 3'-prodrug of a 1', 2', 3' or 4'-branched β-D or β-L nucleoside, its pharmaceutically acceptable salt or composition in combination and/or alternation with one or more effective anti-HCV agent in the manufacture of a medicament for the treatment and/or prophylaxis of a Flaviviridae infection in a host;

(t) use of a 2' and/or 3'-prodrug of a 1', 2', 3' or 4'-branched β-D or β-L nucleoside, or its pharmaceutically acceptable salt or composition with the parent of a different a 1', 2', 3' or 4'-branched β-D or β-L nucleoside in the manufacture of a medicament for the treatment and/or prophylaxis of a Flaviviridae infection in a host;

(u) use of a 2' and/or 3'-prodrug of a β-D-2'-methyl-cytidine, or its pharmaceutically acceptable salt or composition thereof in the manufacture of a medicament for the treatment and/or prophylaxis of a Flaviviridae infection in a host; and (v) use of the 2'-valyl or acetyl ester of β-D-2'-methyl-cytidine, or its pharmaceutically acceptable salt or composition thereof in the manufacture of a medicament for the treatment and/or prophylaxis of a Flaviviridae infection in a host.

Flaviviridae included within the scope of this invention are discussed generally in *Fields Virology*, Editors: Fields, B. N., Knipe, D. M., and Howley, P. M., Lippincott-Raven Publishers, Philadelphia, Pa., Chapter 31, 1996. In a particular embodiment of the invention, the Flaviviridae is HCV. In an alternate embodiment of the invention, the Flaviviridae is a flavivirus or pestivirus. Specific flaviviruses include, without limitation: Absettarov, Alfuy, Apoi, Aroa, Bagaza, Banzi, Bouboui, Bussuquara, Cacipacore, Carey Island, Dakar bat, Dengue 1, Dengue 2, Dengue 3, Dengue 4, Edge Hill, Entebbe bat, Gadgets Gully, Hanzalova, Hypr, llheus, Israel turkey meningoencephalitis, Japanese encephalitis, Jugra, Jutiapa, Kadam, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Naranjal, Negishi, Ntaya, Omsk hemorrhagic fever, Phnom-Penh bat, Powassan, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tyuleniy, Uganda S, Usutu, Wesselsbron, West Nile, Yaounde, Yellow fever, and Zika.

Pestiviruses included within the scope of this invention are discussed generally in *Fields Virology*, Editors: Fields, B. N., Knipe, D. M., and Howley, P. M., Lippincott-Raven Publishers, Philadelphia, Pa., Chapter 33, 1996. Specific pestiviruses include, without limitation: bovine viral diarrhea virus ("BVDV"), classical swine fever virus ("CSFV," also called hog cholera virus), and border disease virus ("BDV").

I. Active Compounds

In a first principal embodiment, a compound of Formula (I), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (I):

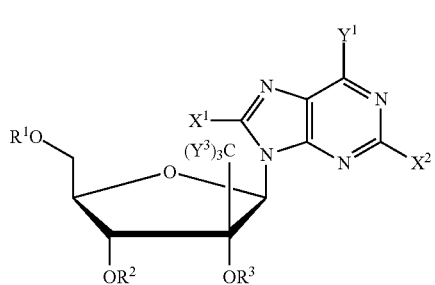

(I)

or a pharmaceutically acceptable salt or prodrug, or a stereoisomeric, tautomeric or polymorphic form thereof, wherein:

$R^1$, $R^2$ and $R^3$ are independently H, phosphate (including mono-, di- or triphosphate and a stabilized phosphate); straight chained, branched or cyclic alkyl (including lower alkyl); acyl (including lower acyl); CO-alkyl, CO-aryl, CO-alkoxyalkyl, CO-aryloxyalkyl, CO-substituted aryl, sulfonate ester including alkyl or arylalkyl sulfonyl including methanesulfonyl and benzyl, wherein the phenyl group is optionally substituted with one or more substituents as described in the definition of aryl given herein; alkylsulfonyl, arylsulfonyl, aralkylsulfonyl, a lipid, including a phospholipid; an amino acid; and amino acid residue, a carbohydrate; a peptide; cholesterol; or other pharmaceutically acceptable leaving group which when administered in vivo is capable of providing a compound wherein $R^1$, $R^2$ and/or $R^3$ is independently H or phosphate (including mono-, di- or triphosphate); wherein in one embodiment $R^2$ and/or $R^3$ is not phosphate (including mono-, di- or triphosphate or a stabilized phosphate prodrug);

wherein at least one of $R^2$ and $R^3$ is not hydrogen;

$Y^1$ is hydrogen, bromo, chloro, fluoro, iodo, CN, OH, $OR^4$, $NH_2$, $NHR^4$, $NR^4R^5$, SH or $SR^4$;

$X^1$ is a straight chained, branched or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted alkenyl, optionally substituted alkynyl, COOH, $COOR^4$, COO-alkyl, COO-aryl, CO—Oalkoxyalkyl, $CONH_2$, $CONIIR^4$, $CON(R^4)_2$, chloro, bromo, fluoro, iodo, CN, $N_3$, OH, $OR^4$, $NH_2$, $NHR^4$, $NR^4R^5$, SH or $SR^5$;

$X^2$ is H, straight chained, branched or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted alkenyl, optionally substituted alkynyl, COOH, $COOR^4$, COO-alkyl, COO-aryl, CO—Oalkoxyalkyl, $CONH_2$, $CONHR^4$, $CON(R^4)_2$, chloro, bromo, fluoro, iodo, CN, $N_3$, OH, $OR^4$, $NH_2$, $NHR^4$, $NR^4R^5$, SH or $SR^5$; and wherein each $Y^3$ is independently H, F, Cl, Br or I;

each $R^4$ and $R^5$ is independently hydrogen, acyl (including lower acyl), alkyl (including but not limited to methyl, ethyl, propyl and cyclopropyl), lower alkyl, alkenyl, alkynyl or cycloalkyl.

In a preferred subembodiment, a compound of Formula (I) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (I) or a pharmaceutically acceptable salt or prodrug, or a stereoisomeric, tautomeric or polymorphic form thereof, wherein:

$R^1$ is H or phosphate (preferably H);

$R^2$ and $R^3$ are independently H, phosphate, acyl or an amino acid residue, wherein at least one of $R^2$ and $R^3$ is acyl or an amino acid residue;

$X^1$ is $CH_3$, $CF_3$ or $CH_2CH_3$;

$X^2$ is H or $NH_2$; and

Y is hydrogen, bromo, chloro, fluoro, iodo, $NH_2$ or OH.

In a second principal embodiment, a compound of Formula (II) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (II):

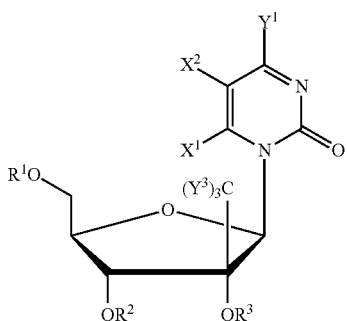

(II)

or a pharmaceutically acceptable salt or prodrug, or a stereoisomeric, tautomeric or polymorphic form thereof, wherein:
$R^1$, $R^2$, $R^3$, $R^4$, $R^5$, $Y^1$, $Y^3$, $X^1$ and $X^2$ are as defined above.

In a preferred subembodiment, a compound of Formula (II), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (II) or a pharmaceutically acceptable salt or prodrug, or a stereoisomeric, tautomeric or polymorphic form thereof, wherein:

$R^1$ is H or phosphate (preferably H);
$R^2$ and $R^3$ are independently H, phosphate, acyl or an amino acid residue, wherein at least one of $R^2$ and $R^3$ is acyl or an amino acid residue;
$X^1$ is $CH_3$, $CF_3$ or $CH_2CH_3$;
$X^2$ is H, F, Cl, Br, I or $CH_3$; and
Y is hydrogen, bromo, chloro, fluoro, iodo, $NH_2$ or OH.

In a third principal embodiment, a compound of Formula (III), (IV) or (V) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (III), (IV), or (V):

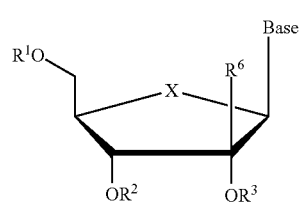

(III)

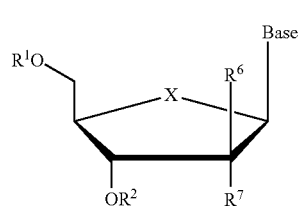

(IV)

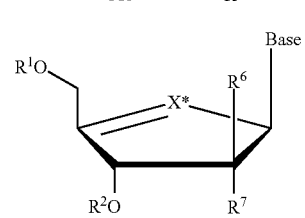

(V)

or a pharmaceutically acceptable salt or prodrug, or a stereoisomeric, tautomeric or polymorphic form thereof, wherein:
$R^1$, $R^2$, $R^3$, $R^4$, $R^5$, Y, $Y^1$ and $X^2$ are as defined above;
Base is selected from the group consisting of:

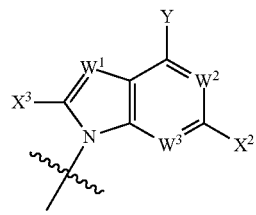

(A)

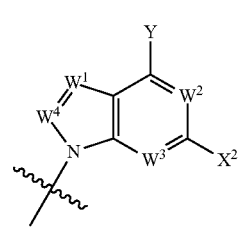

(B)

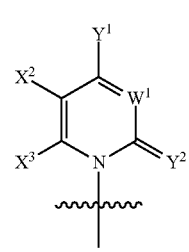

(C)

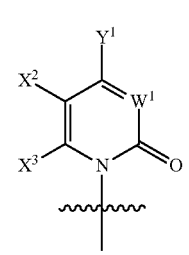

(D)

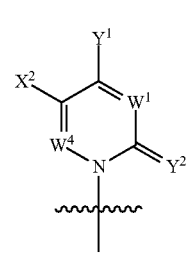

(E)

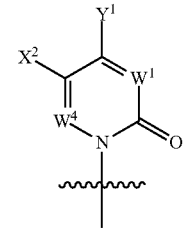

(F)

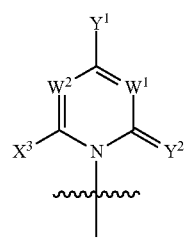 (G)
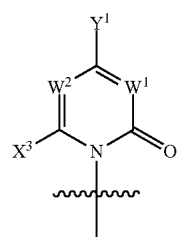 (H)
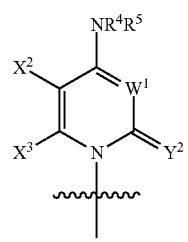 (I)
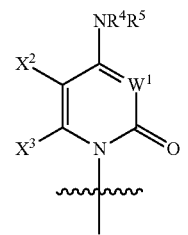 (J)
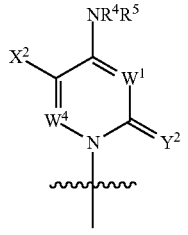 (K)
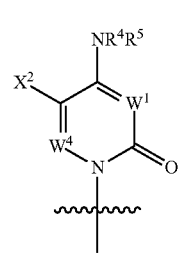 (L)
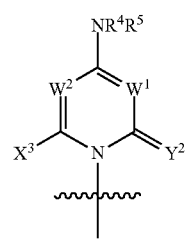 (M)
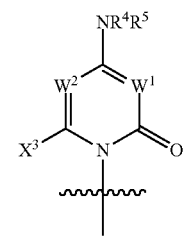 (N)
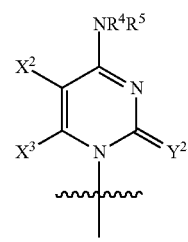 (O)
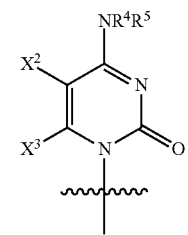 (P)
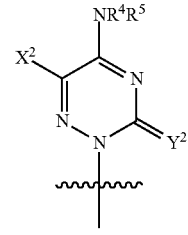 (Q)
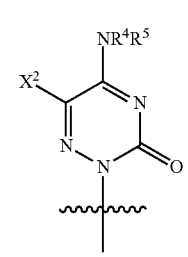 (R)

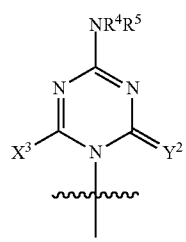 (S)
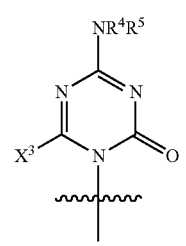 (T)
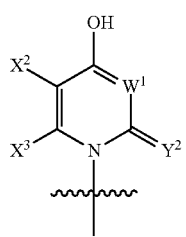 (U)
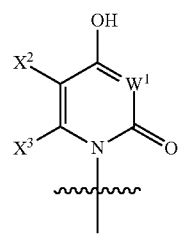 (V)
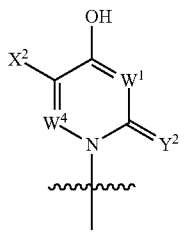 (W)
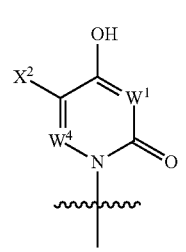 (X)
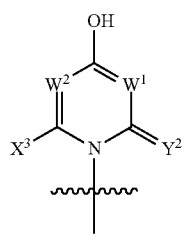 (Y)
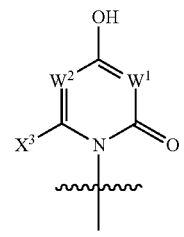 (Z)
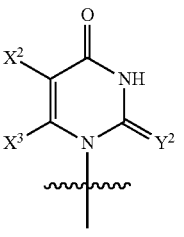 (AA)
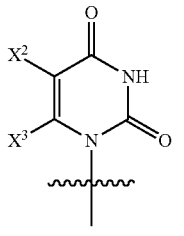 (AB)
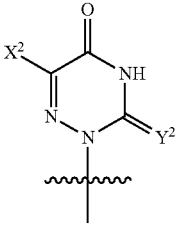 (AC)
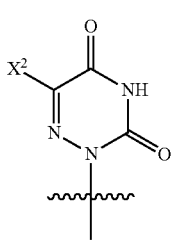 (AD)

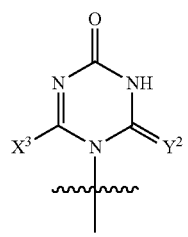 (AE)
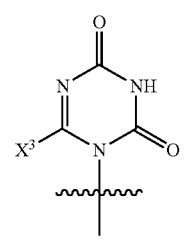 (AF)
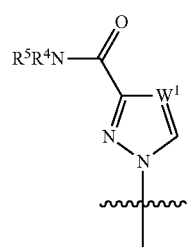 (AG)
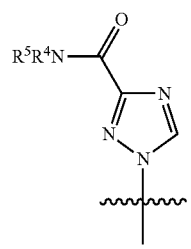 (AH)
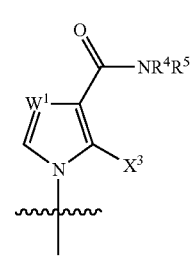 (AI)
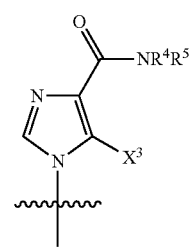 (AJ)
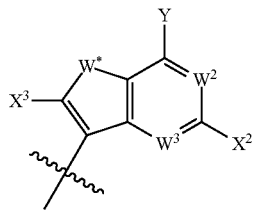 (BA)
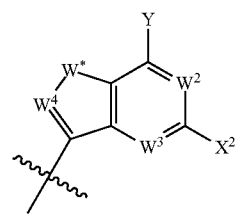 (BB)
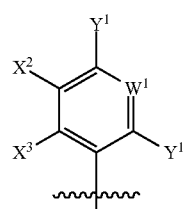 (BC)
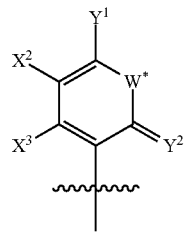 (BD)
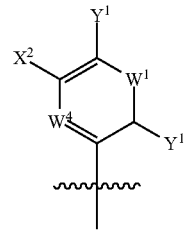 (BE)
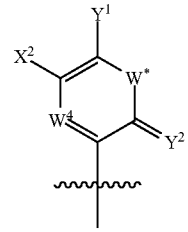 (BF)
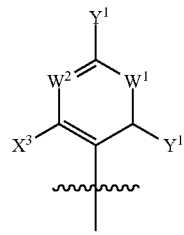 (BG)

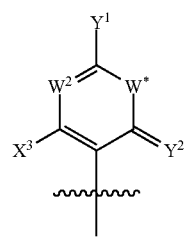
(BH)
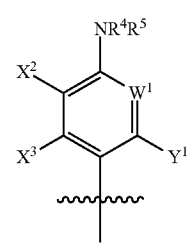
(BI)
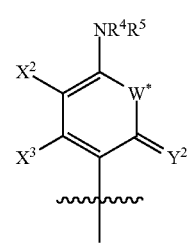
(BJ)
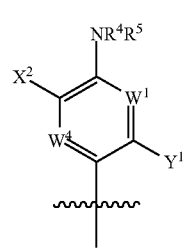
(BK)
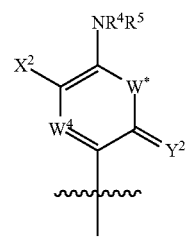
(BL)
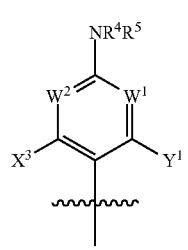
(BM)
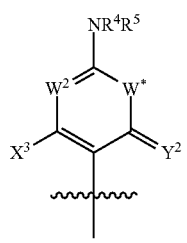
(BN)
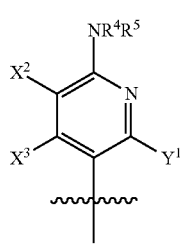
(BO)
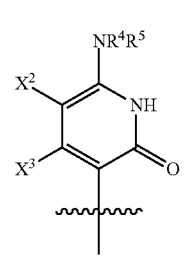
(BP)
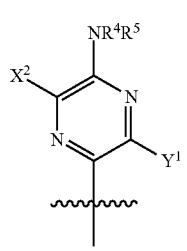
(BQ)
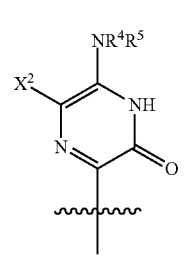
(BR)
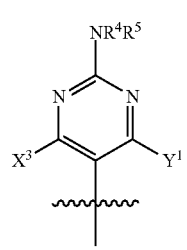
(BS)

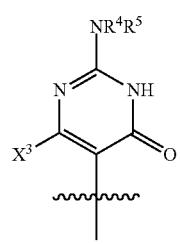
(BT)
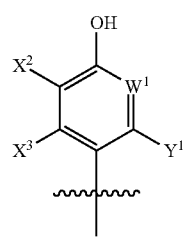
(BU)
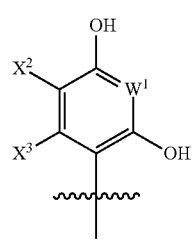
(BV)
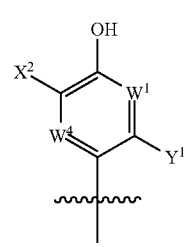
(BW)
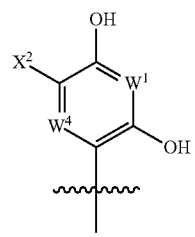
(BX)
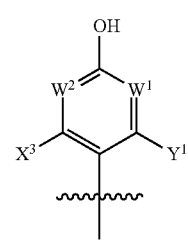
(BY)
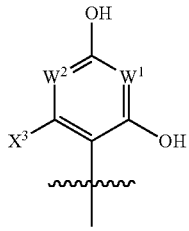
(BZ)
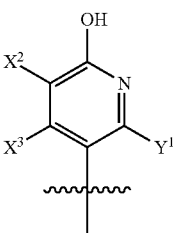
(BAA)
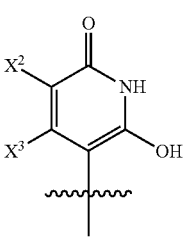
(BAB)
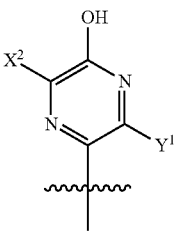
(BAC)
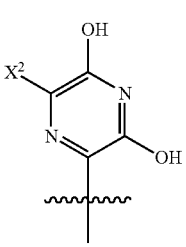
(BAD)
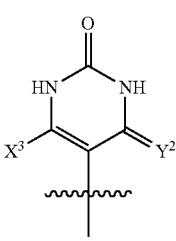
(BAE)

-continued

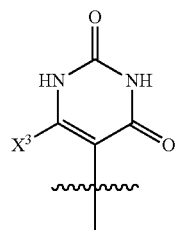

(BAF)

each $W^1$, $W^2$, $W^3$ and $W^4$ is independently N, CH, CF, CI, CBr, CCl, CCN, $CCH_3$, $CCF_3$, $CCH_2CH_3$, $CC(O)NH_2$, $CC(O)NHR^4$, $CC(O)N(R^4)_2$, $CC(O)OH$, $CC(O)OR^4$ or $CX^3$;
each W* is independently O, S, NH or $NR^4$;
wherein for Base (B), $W^4$ cannot be CH if $W^1$, $W^2$ and $W^3$ are N;
wherein for Base (E), (F), (K), (L), (W) and (X), $W^4$ cannot be CH if W' is N;
X is O, S, $SO_2$, $CH_2$, $CH_2OH$, CHF, $CF_2$, $C(Y^3)_2$, CHCN, $C(CN)_2$, $CHR^4$ or $C(R^4)_2$; X* is CH, CF, $CY^3$ or $CR^4$;
each $X^3$ is independently a straight chained, branched or cyclic optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, $N_3$, CN, —C(O)OH, —C(O)$OR^4$, —C(O)O (lower alkyl), —C(O)$NH_2$, —C(O)$NHR^4$, —C(O)NH(lower alkyl), —C(O)$N(R^4)_2$, —C(O)N(lower alkyl)$_2$, OH, $OR^4$, —O(acyl), —O(lower acyl), —O(alkyl), —O(lower alkyl), —O(alkenyl), —O(alkynyl), —O(aralkyl), —O(cycloalkyl), —S(acyl), —S(lower acyl), —S($R^4$), —S(lower alkyl), —S(alkenyl), —S(alkynyl), —S(aralkyl), —S(cycloalkyl), chloro, bromo, fluoro, iodo, $NH_2$, —NH(lower alkyl), —$NHR^4$, —$NR^4R^5$, —NH(acyl), —N(lower alkyl)$_2$, —NH(alkenyl), —NH(alkynyl), —NH(aralkyl), —NH(cycloalkyl), —N(acyl)$_2$;
each $Y^2$ is independently O, S, NH or $NR^4$;
each $Y^3$ is independently H, F, Cl, Br or I;
each $R^6$ is independently an optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, —$CH_2C(O)OH$, —$CH_2C(O)OR^4$, —$CH_2C(O)O$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —C(O)OH, —C(O)$OR^4$, —C(O)O(lower alkyl), —C(O)$NH_2$, —C(O)$NHR^4$, —C(O)NH(lower alkyl), —C(O)N$(R^4)_2$, —C(O)N(lower alkyl)$_2$ or cyano;
each $R^7$ is independently OH, $OR^2$, optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, optionally substituted carbocycle (preferably a 3-7 membered carbocyclic ring), optionally substituted heterocycle (preferably a 3-7 membered heterocyclic ring having one or more O, S and/or N), optionally substituted heteroaryl (preferably a 3-7 membered heteroaromatic ring having one or more O, S and/or N), —$CH_2C(O)OH$, —$CH_2C(O)OR^4$, —$CH_2C(O)O$(lower alkyl), —$CH_2C(O)SH$, —$CH_2C(O)SR^4$, —$CH_2C(O)S$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)SH$, —$(CH_2)_mC(O)SR^4$, —$(CH_2)_mC(O)S$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —C(O)OH, —C(O)$OR^4$, —C(O)O(lower alkyl), —C(O)SH, —C(O)$SR^4$, —C(O)S(lower alkyl), —C(O)$NH_2$, —C(O)$NHR^4$, —C(O)NH(lower alkyl), —C(O)$N(R^4)_2$, —C(O)N(lower alkyl)$_2$, —O(acyl), —O(lower acyl), —O($R^4$), —O(alkyl), —O(lower alkyl), —O(alkenyl), —O(alkynyl), —O(aralkyl), —O(cycloalkyl), —S(acyl), —S(lower acyl), —S($R^4$), —S(lower alkyl), —S(alkenyl), —S(alkynyl), —S(aralkyl), —S(cycloalkyl), $NO_2$, $NH_2$, —NH(lower alkyl), —$NHR^4$, —$NR^4R^5$, —NH(acyl), —N(lower alkyl)$_2$, —NH(alkenyl), —NH(alkynyl), —NH(aralkyl), —NH(cycloalkyl), —N(acyl)$_{21}$ azido, cyano, SCN, OCN, NCO or halo (fluoro, chloro, bromo, iodo);
alternatively, $R^6$ and $R^7$ can come together to form a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N); and
each m is independently 0, 1 or 2.

In a first subembodiment, the compound of Formula (III), (IV) or (V), or a pharmaceutically acceptable salt or prodrug, or a stereoisomeric, tautomeric or polymorphic form thereof, or the method for the treatment of a host infected with a Flaviviridae comprising administering an effective treatment amount of compound of Formula (III), (IV), or (V) or a pharmaceutically acceptable salt or prodrug, or a stereoisomeric, tautomeric or polymorphic form thereof, is provided, wherein:
$R^1$ is H or phosphate (preferably H);
$R^2$ and $R^3$ are independently H, phosphate, acyl or an amino acid residue, wherein at least one of $R^2$ and $R^3$ is acyl or an amino acid residue;
$W^4$ is $CX^3$;
$X^3$ is $CH_3$, $CF_3$ or $CH_2CH_3$;
$R^6$ is alkyl; and
X is O, S, $SO_2$ or $CH_2$.

In a second subembodiment, the compound of Formula (III), (IV) or (V), or a pharmaceutically acceptable salt or prodrug, or a stereoisomeric, tautomeric or polymorphic form thereof, or the method for the treatment of a host infected with a Flaviviridae comprising administering an effective treatment amount of compound of Formula (III), (IV) or (V), or a pharmaceutically acceptable salt or prodrug, or a stereoisomeric, tautomeric or polymorphic form thereof, is provided, wherein:
$R^1$ is H or phosphate (preferably H);
$R^2$ and $R^3$ are independently H, phosphate, acyl or an amino acid residue, wherein at least one of $R^2$ and $R^3$ is an amino acid residue;
$W^4$ is $CX^3$;
$X^3$ is $CH_3$, $CF_3$ or $CH_2CH_3$;
$R^6$ is alkyl; and
X is O, S, $SO_2$ or $CH_2$.

In a third subembodiment, the compound of Formula (III), (IV) or (V), or a pharmaceutically acceptable salt or prodrug, or a stereoisomeric, tautomeric or polymorphic form thereof, or the method for the treatment of a host infected with a Flaviviridae comprising administering an effective treatment amount of compound of Formula (III), (IV) or (V), or a pharmaceutically acceptable salt or prodrug, or a stereoisomeric, tautomeric or polymorphic form thereof, is provided, wherein:

$R^1$ is H or phosphate (preferably II);
$R^2$ and $R^3$ are independently H, phosphate, acyl or an amino acid residue, wherein at least one of $R^2$ and $R^3$ is acyl or an amino acid residue;
$W^4$ is $CX^3$;
$X^3$ is $CH_3$, $CF_3$ or $CH_2CH_3$;
$R^6$ is alkyl; and
X is O.

In even more preferred subembodiment, the compound of Formula (IV(a)), or a pharmaceutically acceptable salt or prodrug, or a stereoisomeric, tautomeric or polymorphic form thereof, is provided, as well as the method for the treatment of a host infected with a Flaviviridae comprising administering an effective treatment amount of compound of Formula (IV (a)):

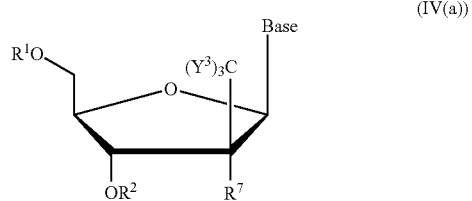

(IV(a))

or a pharmaceutically acceptable salt or prodrug, or a stereoisomeric, tautomeric or polymorphic form thereof, wherein: Base is as defined herein; optionally substituted with an amine or cyclopropyl (e.g., 2-amino, 2,6-diamino or cyclopropyl guanosine);
$R^7$ is halo (F, Cl, Br or I), though preferably F;
$R^1$ is H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ or $R^2$ is independently H or phosphate. In one embodiment $R^2$ is not phosphate (including monophosphate, diphosphate, triphosphate, or a stabilized phosphate prodrug); and
$R^2$ is phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ or $R^2$ is independently H or phosphate. In one embodiment $R^2$ is not phosphate (including monophosphate, diphosphate, triphosphate, or a stabilized phosphate prodrug).

In a fourth principal embodiment, a compound of Formula (VI) or (VII) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (VI) or (VII):

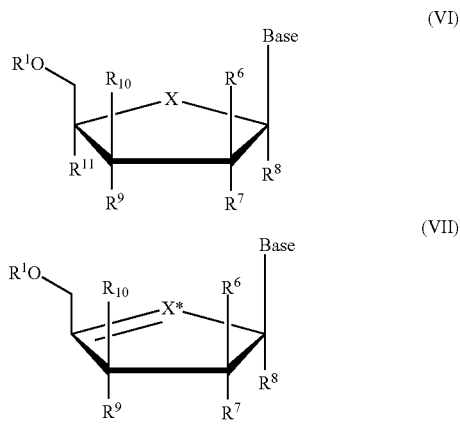

or a pharmaceutically acceptable salt or prodrug, or a stereoisomeric, tautomeric or polymorphic form thereof, is provided, wherein:
Base, R, $R^1$, $R^4$, $R^5$, $R^6$, $R^7$, Y, $Y^1$, $Y^2$, $Y^3$, W*, $W^1$, $W^2$, $W^3$, $W^4$, X, X*, $X^1$, $X^2$, and $X^3$ are as defined above;
wherein, in one embodiment, $R^8$ in Formula (VI) is —OH or —$NH_2$ only when X is carbon; and
wherein;
each $R^8$ and $R^{11}$ is independently hydrogen, an optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, —$CH_2C(O)OH$, —$CH_2C(O)OR^4$, —$CH_2C(O)O$(lower alkyl), —$CH_2C(O)NH_2$, —$CH_2C(O)NHR^4$, —$CH_2C(O)NH$ (lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —$C(O)OH$, —$C(O)OR^4$, —$C(O)O$(lower alkyl), —$C(O)NH_2$, —$C(O)NHR^4$, —$C(O)NH$(lower alkyl), —$C(O)N(R^4)_2$, —$C(O)N$(lower alkyl)$_2$, cyano, NH-acyl or N(acyl)$_2$;
each $R^9$ and $R^{10}$ are independently hydrogen, OH, $OR^2$, optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, optionally substituted carbocycle (preferably a 3-7 membered carbocyclic ring), optionally substituted heterocycle (preferably a 3-7 membered heterocyclic ring having one or more O, S and/or N), optionally substituted heteroaryl (preferably a 3-7 membered heteroaromatic ring having one or more O, S and/or N), —CH$_2$C(O)OH, —CH$_2$C(O)OR$^4$, —CH$_2$C(O)O(lower alkyl), —CH$_2$C(O)SH, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), —N(acyl)$_2$, azido, cyano, SCN, OCN, NCO or halo (fluoro, chloro, bromo, iodo);

each m is independently 0, 1 or 2; and alternatively, R$^6$ and R$^{10}$, R$^7$ and R$^9$, R$^8$ and R$^7$ or R$^9$ and R$^{11}$ can come together to form a bridged compound selected from the group consisting of optionally substituted carbocycle (preferably a 3-7 membered carbocyclic ring) or optionally substituted heterocycle (preferably a 3-7 membered heterocyclic ring having one or more O, S and/or N); or alternatively, R$^6$ and R$^7$ or R$^9$ and R$^{10}$ can come together to form a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N).

In a particularly preferred embodiment, a compound of Formula (VI), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, in which:

X is O, S, SO or SO$_2$; and/or each R$^6$ is independently an optionally substituted lower alkyl, optionally substituted alkenyl, optionally substituted alkynyl, optionally substituted cycloalkyl, CH$_2$OH, CH$_2$NH$_2$, CH$_2$NHCH$_3$, CH$_2$N(CH$_3$)$_2$, CH$_2$F, CH$_2$Cl, CH$_2$N$_3$, CH$_2$CN, CH$_2$CF$_3$, CF$_3$, CF$_2$CF$_3$, CH$_2$CO$_2$R$^4$, (CH$_2$)$_m$COOH, (CH$_2$)$_m$COOR$^4$, (CH$_2$)$_m$CONH$_2$, (CH$_2$)$_m$C(ON(R$^4$)$_2$, or (CH$_2$)$_m$CONHR$^4$; and/or each R$^7$ is independently —OH, optionally substituted lower alkyl, optionally substituted alkenyl, optionally substituted alkynyl, optionally substituted cycloalkyl, —O-alkyl, —O-alkenyl, —O-alkynyl, —O-aralkyl, —O-cycloalkyl-, O-acyl, F, Cl, Br, I, CN, NC, SCN, OCN, NCO, NO$_2$, NH$_2$, N$_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, CO$_2$-alkyl, CONH-alkyl, CON-dialkyl, CONH-alkenyl, CONH-alkynyl, CONH-aralkyl, CONH-cycloalkyl, CH$_2$OH, CH$_2$NH$_2$, CH$_2$NHCH$_3$, CH$_2$N(CH$_3$)$_2$, CH$_2$F, CH$_2$Cl, CH$_2$N$_3$, CH$_2$CN, CH$_2$CF$_3$, CF$_3$, CF$_2$CF$_3$, CH$_2$CO$_2$R$^4$, (CH$_2$)$_m$COOH, (CH$_2$)$_m$COOR$^4$, (CH$_2$)$_m$CONH$_2$, (CH$_2$)$_m$CON(R$^4$)$_2$, (CH$_2$)$_m$CONHR$^4$, an optionally substituted 3-7 membered carbocyclic, and an optionally substituted 3-7 membered heterocyclic ring having O, S and/or N independently as a heteroatom taken alone or in combination; and/or each R$^9$ is independently hydrogen, optionally substituted lower alkyl, optionally substituted alkenyl, optionally substituted alkynyl, optionally substituted cycloalkyl, —OH, —O-alkyl, —O-alkenyl, —O-alkynyl, —O-aralkyl, —O-cycloalkyl-, O-acyl, F, Cl, Br, I, CN, NC, SCN, OCN, NCO, NO$_2$, NH$_2$, N$_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, CO$_2$-alkyl, CONH-alkyl, CON-dialkyl, CONH-alkenyl, CONH-alkynyl, CONH-aralkyl, CONH-cycloalkyl, CH$_2$OH, CH$_2$NH$_2$, CH$_2$NHCH$_3$, CH$_2$N(CH$_3$)$_2$, CH$_2$F, CH$_2$Cl, CH$_2$N$_3$, CH$_2$CN, CH$_2$CF$_3$, CF$_3$, CF$_2$CF$_3$, CH$_2$CO$_2$R$^4$, (CH$_2$)$_m$COOH, (CH$_2$)$_m$COOR$^4$, (CH$_2$)$_m$CONH$_2$, (CH$_2$)$_m$CON(R$^4$)$_2$, (CH$_2$)$_m$CONHR$^4$, an optionally substituted 3-7 membered carbocyclic, and an optionally substituted 3-7 membered heterocyclic ring having O, S and/or N independently as a heteroatom taken alone or in combination; and/or each R$^{10}$ is independently hydrogen, an optionally substituted lower alkyl, optionally substituted alkenyl, optionally substituted alkynyl, optionally substituted cycloalkyl, CH$_2$OH, CH$_2$NH$_2$, CH$_2$NHCH$_3$, CH$_2$N(CH$_3$)$_2$, CH$_2$F, CH$_2$Cl, CH$_2$N$_3$, CH$_2$CN, CH$_2$CF$_3$, CF$_3$, CF$_2$CF$_3$, CH$_2$CO$_2$R$^4$, (CH$_2$)$_m$C(OOH, (CH$_2$)$_m$COOR$^4$, (CH$_2$)$_m$CONH$_2$, (CH$_2$)$_m$CON(R$^4$)$_2$, or (CH$_2$)$_m$CONHR$^4$; and/or each R$^8$ and R$^{11}$ is independently H, CH$_3$, CH$_2$OH, CH$_2$F, CH$_2$N$_3$, (CH$_2$)$_m$COOH, (CH$_2$)$_m$COOR$^4$, (CH$_2$)$_m$CONH$_2$, (CH$_2$)$_m$CON(R$^4$)$_2$, (CH$_2$)$_m$CONHR$^4$ and N-acyl; and/or each m is independently 0 or 1; and/or Base is selected from one of the following:

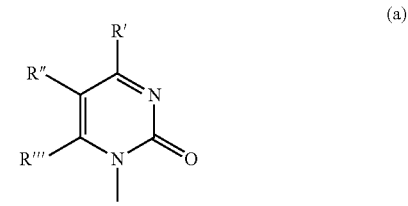

(a)

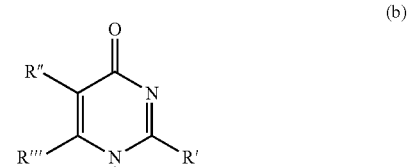

(b)

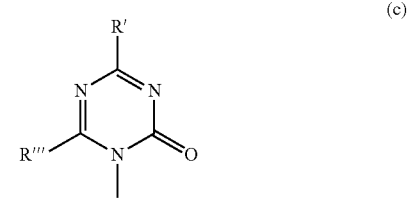

(c)

-continued

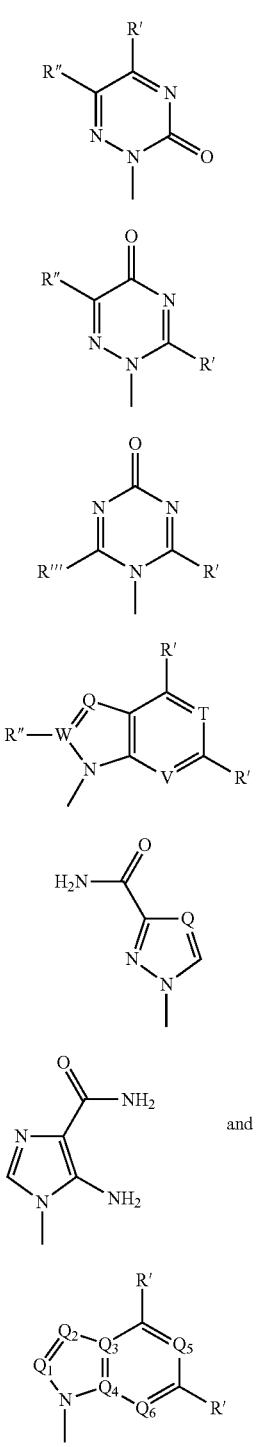

(d)

(e)

(f)

(g)

(h)

(i)

and (j)

wherein:
each R', R", R''' and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mC(OOH$, $(CH_2)_mCN$, $(CH_2)_mNO_2$ and $(CH_2)_mCONH_2$;
W is C—R" or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R;
wherein R is H, alkyl or acyl;
$Q_3$, $Q_4$, $Q_5$ and $Q_6$ independently are N or CH; and
tautomeric forms thereof.

In a particularly preferred alternative embodiment, a compound of Formula (VI), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, in which:

X is O, S, SO or $SO_2$; and/or
$R^6$ and $R^7$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or
each $R^9$ is independently hydrogen, optionally substituted lower alkyl, optionally substituted alkenyl, optionally substituted alkynyl, optionally substituted cycloalkyl, —OH, —O-alkyl, —O-alkenyl, —O-alkynyl, —O-aralkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, $(CH_2)_mCONHR^4$, an optionally substituted 3-7 membered carbocyclic, and an optionally substituted 3-7 membered heterocyclic ring having O, S and/or N independently as a heteroatom taken alone or in combination; and/or
each $R^{10}$ is independently hydrogen, an optionally substituted lower alkyl, optionally substituted alkenyl, optionally substituted alkynyl, optionally substituted cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, or $(CH_2)_mCONHR^4$; and/or
each $R^8$ and $R^{11}$ is independently H, $CH_3$, $CH_2OH$, $CH_2F$, $CH_2N_3$, $(CH_2)_mCOOH$, $(CH_2)_mCOOR^4$, $(CH_2)_mCONH_2$, $(CH_2)_mCON(R^4)_2$, $(CH_2)_mCONHR^4$ and N-acyl; and/or
each m is independently 0 or 1; and/or
Base is selected from one of the following:

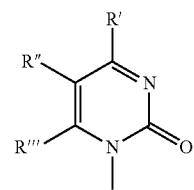

(a)

-continued (b) 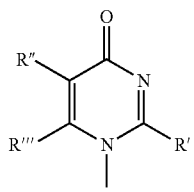

(c) 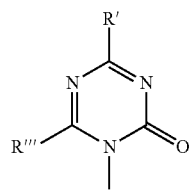

(d) 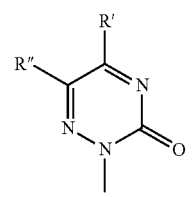

(f) 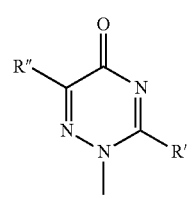

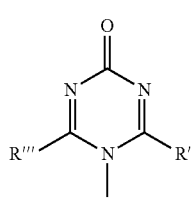

(g) 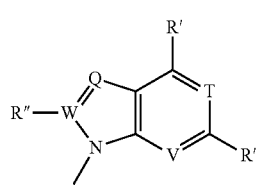

(h) 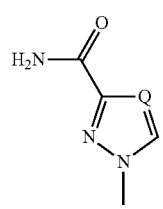

(i) 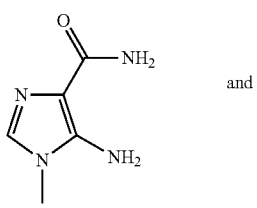

and

-continued (j) 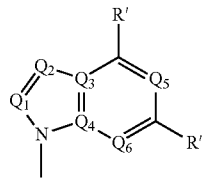

wherein:
each R', R'', R''' and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mC(OOH$, $(CH_2)_mCN$, $(CH_2)_mNO_2$ and $(CH_2)_mCONH_2$;

W is C—R'' or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R;
wherein R is H, alkyl or acyl;
$Q_3$, $Q_4$, $Q_5$ and $Q_6$ independently are N or CH; and
tautomeric forms thereof.

In another particularly preferred embodiment, a compound of Formula (VI), or its pharmaceutically acceptable salt or prodrug thereof, as well as a method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which:

X is O, S, SO or $SO_2$; and/or
each $R^6$ is independently an optionally substituted lower alkyl, optionally substituted alkenyl, optionally substituted alkynyl, optionally substituted cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, or $(CH_2)_mCONHR^4$; and/or each $R^7$ is independently —OH, optionally substituted lower alkyl, optionally substituted alkenyl, optionally substituted alkynyl, optionally substituted cycloalkyl, —O-alkyl, —O-alkenyl, —O-alkynyl, —O-aralkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, $(CH_2)_mCONHR^4$, an optionally substituted 3-7 membered carbocyclic, and an optionally substituted 3-7 membered heterocyclic ring having O, S and/or N independently as a heteroatom taken alone or in combination; and/or $R^9$ and $R^{10}$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or each $R^8$ and $R^{11}$ is independently H, $CH_3$, $CH_2OH$, $CH_2F$, $CH_2N_3$, $(CH_2)_mCOOH$, $(CH_2)_mCOOR^4$, $(CH_2)_mCONH_2$, $(CH_2)_mC(ON(R^4)_2$, $(CH_2)_mCONHR^4$ and N-acyl; and/or each m is independently 0 or 1; and/or Base is selected from one of the following:

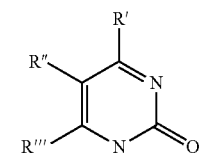
(a)

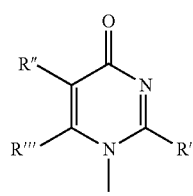
(b)

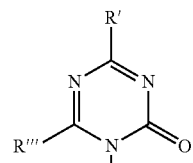
(c)

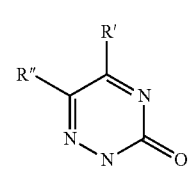
(d)

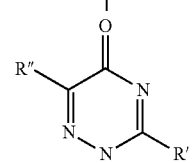
(e)

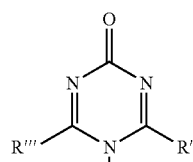
(f)

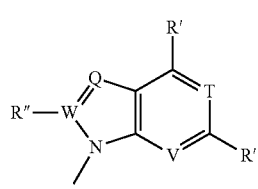
(g)

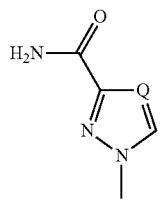
(h)

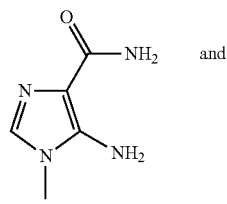
(i) and (j)

wherein:
each R', R", R''' and R"" is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$ and $(CH_2)_mCONH_2$;

W is C—R" or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R;
wherein R is H, alkyl or acyl;
$Q_3$, $Q_4$, $Q_5$ and $Q_6$ independently are N or CH; and
tautomeric forms thereof.

In another particularly preferred embodiment, a compound of Formula (VI), or a pharmaceutically acceptable salt or prodrug, or a stereoisomeric, tautomeric or polymorphic form thereof, as well as a method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which:

X is O, S, SO or $SO_2$; and/or $R^6$ and $R^7$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or $R^9$ and $R^{10}$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or each $R^8$ and $R^{11}$ is independently H, $CH_3$, $CH_2OH$, $CH_2F$, $CH_2N_3$, $(CH_2)_mCOOH$, $(CH_2)_mCOOR^4$, $(CH_2)_mCONH_2$, $(CH_2)_mCON(R^4)_2$, $(CH_2)_mCONHR^4$ and N-acyl; and/or each m is independently 0 or 1; and/or Base is selected from one of the following:

(a)
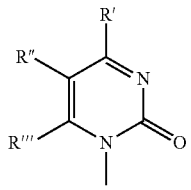

(b)
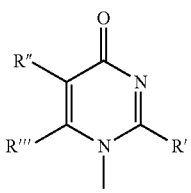

(c)
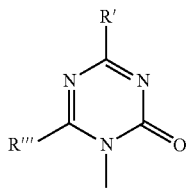

(d)
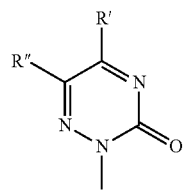

(e)
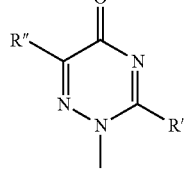

(f)
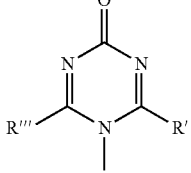

(g)
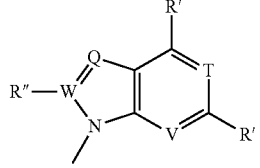

(h)
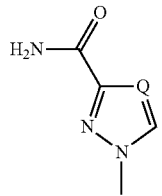

(i)
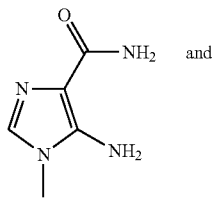

and (j)
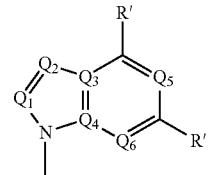

wherein:
each R', R", R''' and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mC(OOH$, $(CH_2)_mCN$, $(CH_2)_mNO_2$ and $(CH_2)_mCONH_2$;

W is C—R" or N;

T and V independently are CH or N;

Q is CH, —CCl, —CBr, —CF, —CI, —CCN, —C—COOH, —C—$CONH_2$, or N;

$Q_1$ and $Q_2$ independently are N or C—R;

wherein R is H, alkyl or acyl;

$Q_3$, $Q_4$, $Q_5$ and $Q_6$ independently are N or CH; and tautomeric forms thereof.

In a particularly preferred embodiment, a compound of Formula (VI), or its pharmaceutically acceptable salt or prodrug thereof, or a stereoisomeric, tautomeric or polymorphic form thereof, as well as a method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which:

X is $CH_2$, $CH_2OH$, CHF, $CF_2$, $C(Y^3)_2$, CHCN, $C(CN)_2$, $CHR^4$ or $C(R^4)_2$; and/or each $R^6$ is independently an optionally substituted lower alkyl, optionally substituted alkenyl, optionally substituted alkynyl, optionally substituted cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, or $(CH_2)_mCONHR^4$; and/or each R⁷ is independently —OH, optionally substituted lower alkyl, optionally substituted alkenyl, optionally substituted alkynyl, optionally substituted cycloalkyl, —O-alkyl, —O-alkenyl, —O-alkynyl, —O-aralkyl, —O-cycloalkyl-, O-acyl, F, Cl, Br, I, CN, NC, SCN, OCN, NCO, NO₂, NH₂, N₃, NH-acyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, CO₂-alkyl, CONH-alkyl, CON-dialkyl, CONH-alkenyl, CONH-alkynyl, CONH-aralkyl, CONH-cycloalkyl, CH₂OH, CH₂NH₂, CH₂NHCH₃, CH₂N(CH₃)₂, CH₂F, CH₂Cl, CH₂N₃, CH₂CN, CH₂CF₃, CF₃, CF₂CF₃, CH₂CO₂R⁴, (CH₂)ₘCOOH, (CH₂)ₘCOOR⁴, (CH₂)ₘCONH₂, (CH₂)ₘCON(R⁴)₂, (CH₂)ₘCONHR⁴, an optionally substituted 3-7 membered carbocyclic, and an optionally substituted 3-7 membered heterocyclic ring having O, S and/or N independently as a heteroatom taken alone or in combination; and/or each R⁹ is independently hydrogen, optionally substituted lower alkyl, optionally substituted alkenyl, optionally substituted alkynyl, optionally substituted cycloalkyl, —OH, —O-alkyl, —O-alkenyl, —O-alkynyl, —O-aralkyl, —O-cycloalkyl-, O-acyl, F, Cl, Br, I, CN, NC, SCN, OCN, NCO, NO₂, NH₂, N₃, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, CO₂-alkyl, CONH-alkyl, CON-dialkyl, CONH-alkenyl, CONH-alkynyl, CONH-aralkyl, CONH-cycloalkyl, CH₂OH, CH₂NH₂, CH₂NHCH₃, CH₂N(CH₃)₂, CH₂F, CH₂Cl, CH₂N₃, CH₂CN, CH₂CF₃, CF₃, CF₂CF₃, CH₂CO₂R⁴, (CH₂)ₘC(OOH), (CH₂)ₘCOOR⁴, (CH₂)ₘCONH₂, (CH₂)ₘCON(R⁴)₂, (CH₂)ₘCONHR⁴, an optionally substituted 3-7 membered carbocyclic, and an optionally substituted 3-7 membered heterocyclic ring having O, S and/or N independently as a heteroatom taken alone or in combination; and/or each R¹⁰ is independently hydrogen, an optionally substituted lower alkyl, optionally substituted alkenyl, optionally substituted alkynyl, optionally substituted cycloalkyl, CH₂OH, CH₂NH₂, CH₂NHCH₃, CH₂N(CH₃)₂, CH₂F, CH₂Cl, CH₂N₃, CH₂CN, CH₂CF₃, CF₃, CF₂CF₃, CH₂CO₂R⁴, (CH₂)ₘCOOH, (CH₂)ₘCOOR⁴, (CH₂)ₘCONH₂, (CH₂)ₘCON(R⁴)₂, or (CH₂)ₘCONHR⁴; and/or each R⁸ and R¹¹ is independently H, CH₃, CH₂OH, CH₂F, CH₂N₃, (CH₂)ₘCOOH, (CH₂)ₘCOOR⁴, (CH₂)ₘCONH₂, (CH₂)ₘCON(R⁴)₂, (CH₂)ₘCONHR⁴ and N-acyl; and/or each m is independently 0 or 1; and/or Base is selected from one of the following:

(a)
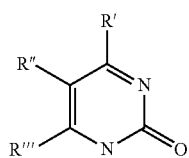

(b)
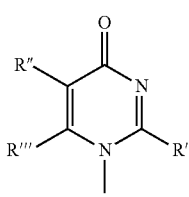

(c)
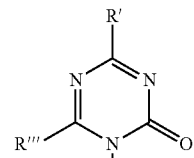

(d)
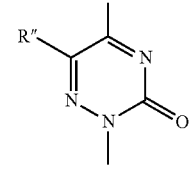

(f)
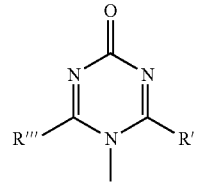

(g)
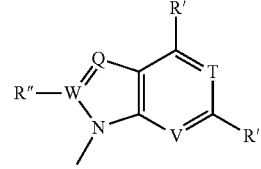

(h)
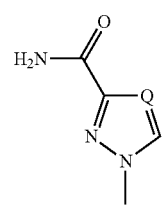

(i)
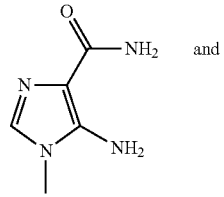 and (j)
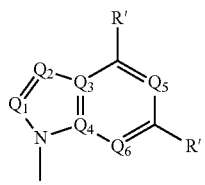

wherein:
each R', R'', R''' and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl. O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$ and $(CH_2)_mCONH_2$;

W is C—R" or N;

T and V independently are CH or N;

Q is CH, —CCl, —CBr, —CF, —CI, —CCN, —C—COOH, —C—$CONH_2$, or N;

$Q_1$ and $Q_2$ independently are N or C—R;

$Q_3$, $Q_4$, $Q_5$ and $Q_6$ independently are N or CH; and tautomeric forms thereof.

In a particularly preferred alternative embodiment, a compound of Formula (VI), or a pharmaceutically acceptable salt or prodrug, or a stereoisomeric, tautomeric or polymorphic form thereof, as well as a method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which:

X is $CH_2$, $CH_2OH$, CHF, $CF_2$, $C(Y^3)_2$, CHCN, $C(CN)_2$, $CHR^4$ or $C(R^4)_2$; and/or $R^6$ and $R^7$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or each $R^9$ is independently hydrogen, optionally substituted lower alkyl, optionally substituted alkenyl, optionally substituted alkynyl, optionally substituted cycloalkyl, —OH, —O-alkyl, —O-alkenyl, —O-alkynyl, —O-aralkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, $(CH_2)_mCONHR^4$, an optionally substituted 3-7 membered carbocyclic, and an optionally substituted 3-7 membered heterocyclic ring having O, S and/or N independently as a heteroatom taken alone or in combination; and/or each $R^{10}$ is independently hydrogen, an optionally substituted lower alkyl, optionally substituted alkenyl, optionally substituted alkynyl, optionally substituted cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, or $(CH_2)_mCONHR^4$; and/or each $R^8$ and $R^{11}$ is independently H, $CH_3$, $CH_2OH$, $CH_2F$, $CH_2N_3$, $(CH_2)_mCOOH$, $(CH_2)_mCOOR^4$, $(CH_2)_mCONH_2$, $(CH_2)_mC(ON(R^4)_2$, $(CH_2)_mCONHR^4$ and N-acyl; and/or each m is independently 0 or 1; and/or Base is selected from one of the following:

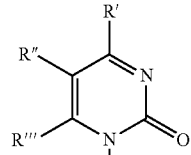
(a)

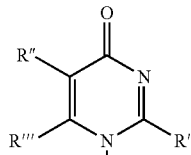
(b)

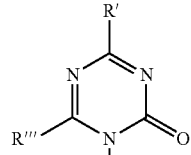
(c)

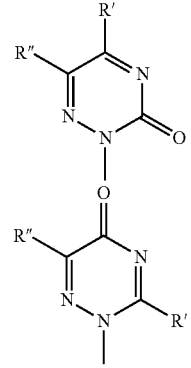
(d)

(e)

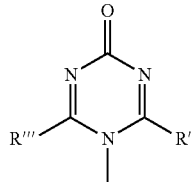
(f)

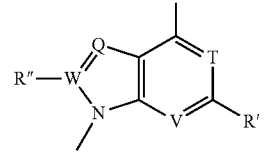
(g)

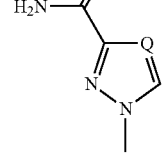
(h)

-continued

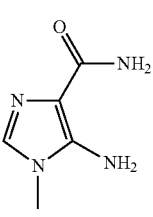
(i)

and

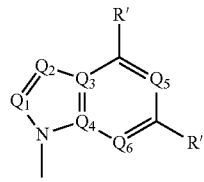
(j)

wherein:
each R', R", R''' and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mC(OOH$, $(CH_2)_m$ CN, $(CH_2)_mNO_2$ and $(CH_2)_mCONH_2$;
W is C—R" or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R;
wherein R is H, alkyl or acyl;
$Q_3$, $Q_4$, $Q_5$ and $Q_6$ independently are N or CH; and
tautomeric forms thereof.

In another particularly preferred embodiment, a compound of Formula (VI), or a pharmaceutically acceptable salt or prodrug, or a stereoisomeric, tautomeric or polymorphic form thereof, as well as a method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which:

X is $CH_2$, $CH_2OH$, CHF, $CF_2$, $C(Y^3)_2$, CHCN, $C(CN)_2$, $CHR^4$ or $C(R^4)_2$; and/or each $R^6$ is independently an optionally substituted lower alkyl, optionally substituted alkenyl, optionally substituted alkynyl, optionally substituted cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, or $(CH_2)_mCONHR^4$; and/or each $R^7$ is independently —OH, optionally substituted lower alkyl, optionally substituted alkenyl, optionally substituted alkynyl, optionally substituted cycloalkyl, —O-alkyl, —O-alkenyl, —O-alkynyl, —O-aralkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, $(CH_2)_mCONHR^4$, an optionally substituted 3-7 membered carbocyclic, and an optionally substituted 3-7 membered heterocyclic ring having O, S and/or N independently as a heteroatom taken alone or in combination; and/or $R^9$ and $R^{10}$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or each $R^8$ and $R^{11}$ is independently H, $CH_3$, $CH_2OH$, $CH_2F$, $CH_2N_3$, $(CH_2)_mCOOH$, $(CH_2)_mCOOR^4$, $(CH_2)_mCONH_2$, $(CH_2)_mCON(R^4)_2$, $(CH_2)_mCONHR^4$ and N-acyl; and/or each m is independently 0 or 1; and/or Base is selected from one of the following:

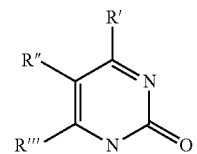
(a)

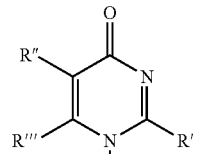
(b)

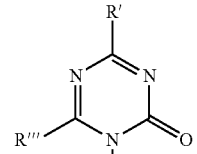
(c)

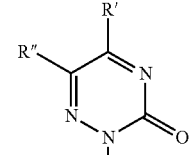
(d)

(e)

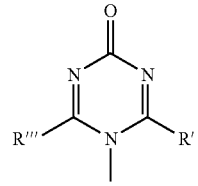
(f)

-continued

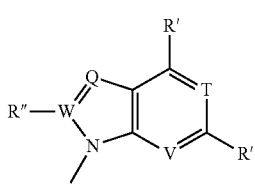 (g)

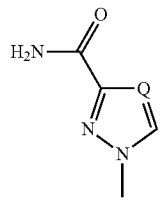 (h)

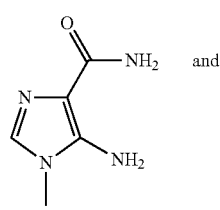 (i)

and

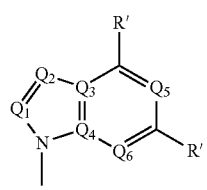 (j)

wherein:
each R', R", R'" and R"" is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mC$ (N, $(CH_2)_mNO_2$ and $(CH_2)_mCONH_2$;
W is C—R" or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R;
wherein R is H, alkyl or acyl;
$Q_3$, $Q_4$, $Q_5$ and $Q_6$ independently are N or CH; and
tautomeric forms thereof.

In another particularly preferred embodiment, a compound of Formula (VI), or a pharmaceutically acceptable salt or prodrug, or a stereoisomeric, tautomeric or polymorphic form thereof, as well as a method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which:
X is $CH_2$, $CH_2OH$, CHF, $CF_2$, $C(Y^3)_2$, CHCN, $C(CN)_2$, $CHR^4$ or $C(R^4)_2$; and/or
$R^6$ and $R^7$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or
$R^9$ and $R^{10}$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or
each $R^8$ and $R^{11}$ is independently H, $CH_3$, $CH_2OH$, $CH_2F$, $CH_2N_3$, $(CH_2)_mCOOH$, $(CH_2)_mCOOR^4$, $(CH_2)_mCONH_2$, $(CH_2)_mCON(R^4)_2$, $(CH_2)_mCONHR^4$ and N-acyl; and/or
each m is independently 0 or 1; and/or
Base is selected from one of the following:

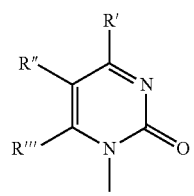 (a)

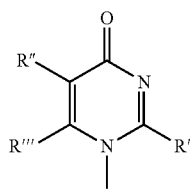 (b)

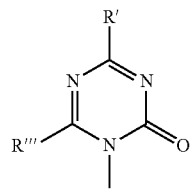 (c)

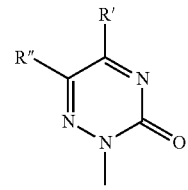 (d)

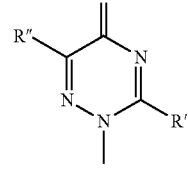 (e)

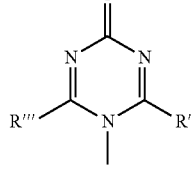 (f)

-continued

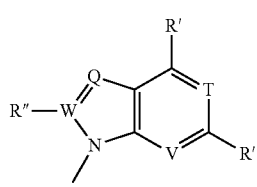
(g)

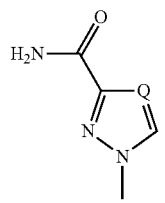
(h)

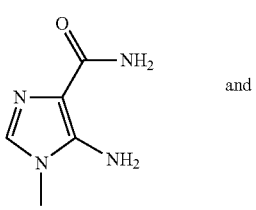
(i)

and

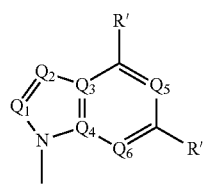
(j)

wherein:
each R', R", R'" and R'" is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$ and $(CH_2)_mCONH_2$;
W is C—R" or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R;
wherein R is H, alkyl or acyl;
$Q_3$, $Q_4$, $Q_5$ and $Q_6$ independently are N or CH; and tautomeric forms thereof.

In a particularly preferred embodiment, a compound of Formula (VII), or its pharmaceutically acceptable salt or prodrug thereof, or a stereoisomeric, tautomeric or polymorphic form thereof, as well as a method for the treatment of a host infected with a Flaviviridae comprising administering an effective treatment amount of compound of Formula (VII) or a pharmaceutically acceptable salt or prodrug, or a stereoisomeric, tautomeric or polymorphic form thereof, is provided, in which:
X* is CH, CF, $CY^3$ or $CR^4$; and/or
each $R^6$ is independently an optionally substituted lower alkyl, optionally substituted alkenyl, optionally substituted alkynyl, optionally substituted cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, or $(CH_2)_mCONHR^4$; and/or each $R^7$ is independently —OH, optionally substituted lower alkyl, optionally substituted alkenyl, optionally substituted alkynyl, optionally substituted cycloalkyl, —O-alkyl, —O-alkenyl, —O-alkynyl, —O-aralkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, $(CH_2)_mCONHR^4$, an optionally substituted 3-7 membered carbocyclic, and an optionally substituted 3-7 membered heterocyclic ring having O, S and/or N independently as a heteroatom taken alone or in combination; and/or each $R^9$ is independently hydrogen, optionally substituted lower alkyl, optionally substituted alkenyl, optionally substituted alkynyl, optionally substituted cycloalkyl, —OH, —O-alkyl, —O-alkenyl, —O-alkynyl, —O-aralkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, $(CH_2)_mCONHR^4$, an optionally substituted 3-7 membered carbocyclic, and an optionally substituted 3-7 membered heterocyclic ring having O, S and/or N independently as a heteroatom taken alone or in combination; and/or each $R^{10}$ is independently hydrogen, an optionally substituted lower alkyl, optionally substituted alkenyl, optionally substituted alkynyl, optionally substituted cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mC(ON(R^4)_2$, or $(CH_2)_mCONHR^4$; and/or each $R^8$ and $R^{11}$ is independently H, $CH_3$, $CH_2OH$, $CH_2F$, $CH_2N_3$, $(CH_2)_mCOOH$, $(CH_2)_mCOOR^4$, $(CH_2)_mCONH_2$, $(CH_2)_mCON(R^4)_2$, $(CH_2)_mCONHR^4$ and N-acyl; and/or each m is independently 0 or 1; and/or Base is selected from one of the following:

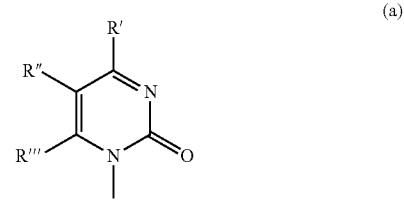
(a)

(b) 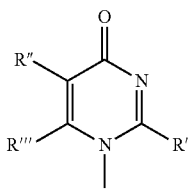

(c) 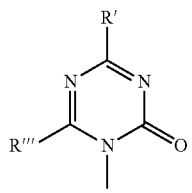

(d) 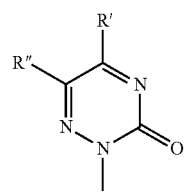

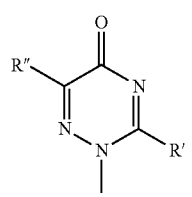

(f) 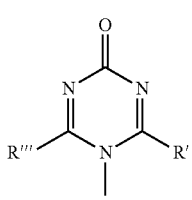

(g) 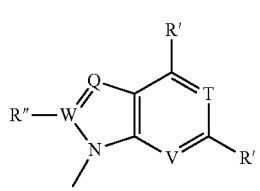

(h) 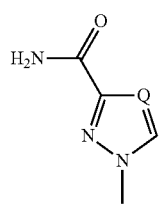

(i) 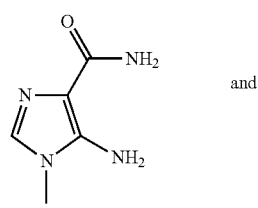

and (j) 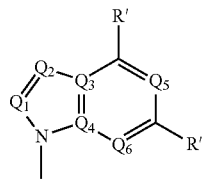

wherein:
each R', R", R''' and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$ and $(CH_2)_mCONH_2$;
W is C—R" or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R;
wherein R is H, alkyl or acyl;
$Q_3$, $Q_4$, $Q_5$ and $Q_6$ independently are N or CH; and
tautomeric forms thereof.

In a particularly preferred alternative embodiment, a compound of Formula (VII), or a pharmaceutically acceptable salt or prodrug, or a stereoisomeric, tautomeric or polymorphic form thereof, as well as a method for the treatment of a host infected with a Flaviviridae comprising administering an effective treatment amount of compound of Formula (VII) or a pharmaceutically acceptable salt or prodrug, or a stereoisomeric, tautomeric or polymorphic form thereof, is provided, in which:
X* is CH, CF, $CY^3$ or $CR^4$; and/or
$R^6$ and $R^7$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or
each $R^9$ is independently hydrogen, optionally substituted lower alkyl, optionally substituted alkenyl, optionally substituted alkynyl, optionally substituted cycloalkyl, —OH, —O-alkyl, —O-alkenyl, —O-alkynyl, —O-aralkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, $(CH_2)_mCONHR^4$, art optionally substituted 3-7 membered carbocyclic, and an optionally substituted 3-7 membered heterocyclic ring having O, S and/or N independently as a heteroatom taken alone or in combination; and/or

83 each $R^{10}$ is independently hydrogen, an optionally substituted lower alkyl, optionally substituted alkenyl, optionally substituted alkynyl, optionally substituted cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R^4$, $(CH_2)_mCOOH$, $(CH_2)_mCOOR^4$, $(CH_2)_mCONH_2$, $(CH_2)_mCON(R^4)_2$, or $(CH_2)_mCONHR^4$; and/or each $R^8$ and $R^{11}$ is independently H, $CH_3$, $CH_2OH$, $CH_2F$, $CH_2N_3$, $(CH_2)_mCOOH$, $(CH_2)_mCOOR^4$, $(CH_2)_mCONH_2$, $(CH_2)_mCON(R^4)_2$, $(CH_2)_mCONHR^4$ and N-acyl; and/or each m is independently 0 or 1; and/or Base is selected from one of the following:

(a)
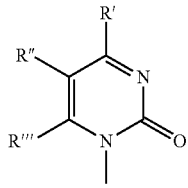

(b)
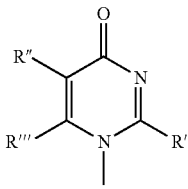

(c)
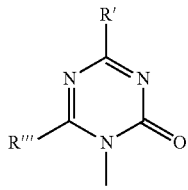

(d)
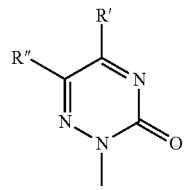

(e)
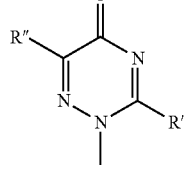

(f)
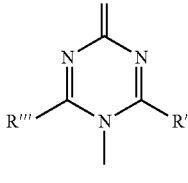

84

-continued (g)
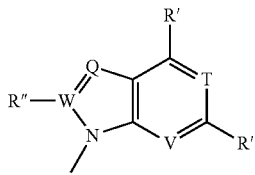

(h)
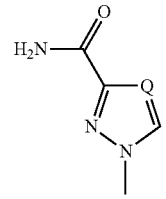

(i)
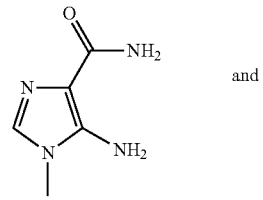

and (j)
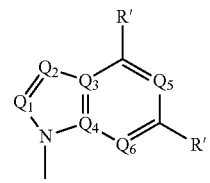

wherein:
each R', R'', R''' and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mC(N, (CH_2)_mNO_2$ and $(CH_2)_mCONH_2$;
W is C—R'' or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R;
R is H, alkyl or acyl;
$Q_3$, $Q_4$, $Q_5$ and $Q_6$ independently are N or CH; and
tautomeric forms thereof.

In another particularly preferred embodiment, a compound of Formula (VII), or a pharmaceutically acceptable salt or prodrug, or a stereoisomeric, tautomeric or polymorphic form thereof, as well as a method for the treatment of a host infected with a Flaviviridae comprising administering an effective treatment amount of compound of Formula or a pharmaceutically acceptable salt or prodrug, or a stereoisomeric, tautomeric or polymorphic form thereof, is provided, in which:
X* is CH, CF, $CY^3$ or $CR^4$; and/or
each $R^6$ is independently an optionally substituted lower alkyl, optionally substituted alkenyl, optionally substituted alkynyl, optionally substituted cycloalkyl, CH$_2$OH, CH$_2$NH$_2$, CH$_2$NHCH$_3$, CH$_2$N(CH$_3$)$_2$, CH$_2$F, CH$_2$Cl, CH$_2$N$_3$, CH$_2$CN, CH$_2$CF$_3$, CF$_3$, CF$_2$CF$_3$, CH$_2$CO$_2$R$^4$, (CH$_2$)$_m$COOH, (CH$_2$)$_m$COOR$^4$, (CH$_2$)$_m$CONH$_2$, (CH$_2$)$_m$CON(R$^4$)$_2$, or (CH$_2$)$_m$CONHR$^4$; and/ or each R$^7$ is independently —OH, optionally substituted lower alkyl, optionally substituted alkenyl, optionally substituted alkynyl, optionally substituted cycloalkyl, —O-alkyl, —O-alkenyl, —O-alkynyl, —O-aralkyl, —O-cycloalkyl-, O-acyl, F, Cl, Br, I, CN, NC, SCN, OCN, NCO, NO$_2$, NH$_2$, N$_3$, NH-acyl, NH-alkyl, N-dialkyl, NH-alkenyl, NH-alkynyl, NH-aralkyl, NH-cycloalkyl, SH, S-alkyl, S-alkenyl, S-alkynyl, S-aralkyl, S-acyl, S-cycloalkyl, CO$_2$-alkyl, CONH-alkyl, CON-dialkyl, CONH-alkenyl, CONH-alkynyl, CONH-aralkyl, CONH-cycloalkyl, CH$_2$OH, CH$_2$NH$_2$, CH$_2$NHCH$_3$, CH$_2$N(CH$_3$)$_2$, CH$_2$F, CH$_2$Cl, CH$_2$N$_3$, CH$_2$CN, CH$_2$CF$_3$, CF$_3$, CF$_2$CF$_3$, CH$_2$CO$_2$R$^4$, (CH$_2$)$_m$COOH, (CH$_2$)$_m$COOR$^4$, (CH$_2$)$_m$CONH$_2$, (CH$_2$)$_m$C(ON(R$^4$)$_2$, (CH$_2$)$_m$CONHR$^4$, an optionally substituted 3-7 membered carbocyclic, and an optionally substituted 3-7 membered heterocyclic ring having O, S and/or N independently as a heteroatom taken alone or in combination; and/or R$^9$ and R$^{10}$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or each R$^8$ and R$^{11}$ is independently H, CH$_3$, CH$_2$OH, CH$_2$F, CH$_2$N$_3$, (CH$_2$)$_m$COOH, (CH$_2$)$_m$COOR$^4$, (CH$_2$)$_m$CONH$_2$, (CH$_2$)$_m$CON(R$^4$)$_2$, (CH$_2$)$_m$CONHR$^4$ and N-acyl; and/or each m is independently 0 or 1; and/or Base is selected from one of the following;

(a)
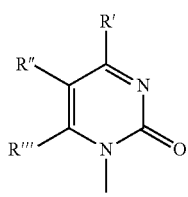

(b)
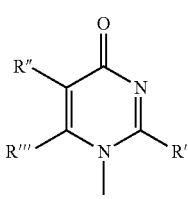

(c)
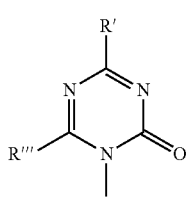

-continued (d)
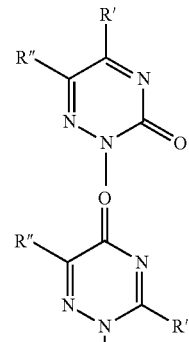

(f)
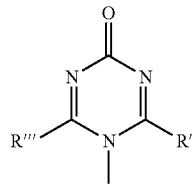

(g)
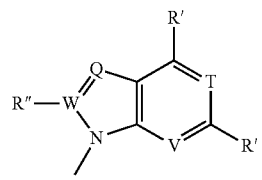

(h)
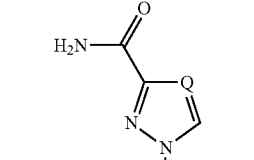

(i)
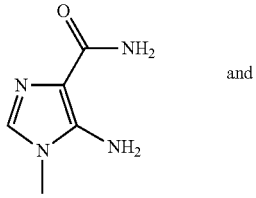

and (j)
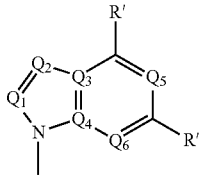

wherein:
each R', R'', R''' and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, NH$_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, CONH$_2$, CO$_2$-alkyl, CONH-alkyl, CON-dialkyl, OH, CF$_3$, CH$_2$OH, $(CH_2)_mOH$, $(CH_2)_mNH_2$, $(CH_2)_mCOOH$, $(CH_2)_mCN$, $(CH_2)_mNO_2$ and $(CH_2)_mCONH_2$;

W is C—R" or N;

T and V independently are CH or N;

Q is CH, —CCl, —CBr, —CF, —CI, —CCN, —C—COOH, —C—CONH$_2$, or N;

$Q_1$ and $Q_2$ independently are N or C—R;

R is H, alkyl or acyl;

$Q_3$, $Q_4$, $Q_5$ and $Q_6$ independently are N or CH; and tautomeric forms thereof.

In another particularly preferred embodiment, a compound of Formula (VII), or a pharmaceutically acceptable salt or prodrug, or a stereoisomeric, tautomeric or polymorphic form thereof, as well as a method for the treatment of a host infected with a Flaviviridae comprising administering an effective treatment amount of compound of Formula (VII) or a pharmaceutically acceptable salt or prodrug, or a stereoisomeric, tautomeric or polymorphic form thereof, is provided, in which:

X* is CH, CF, CY$^3$ or CR$^4$; and/or

R$^6$ and R$^7$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or R$^9$ and R$^{10}$ come together to form a spiro compound selected from the group consisting of optionally substituted 3-7 membered spiro carbocyclic or heterocyclic compound having one or more N, O and/or S atoms, said heteroatoms independently taken alone or in combination with one another; and/or each R$^8$ and R$^{11}$ is independently H, CH$_3$, CH$_2$OH, CH$_2$F, CH$_2$N$_3$, $(CH_2)_mCOOH$, $(CH_2)_mCOOR^4$, $(CH_2)_mCONH_2$, $(CH_2)_mC(ON(R^4)_2$, $(CH_2)_mCONHR^4$ and N-acyl; and/or each m is independently 0 or 1; and/or Base is selected from one of the following:

(a)

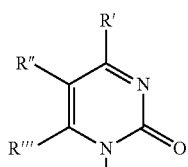

(b)

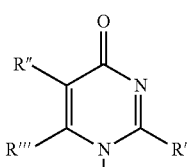

(c)

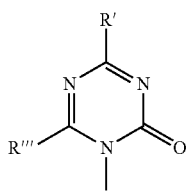

(d)

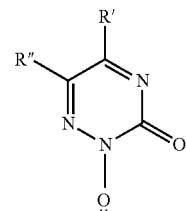

(e)

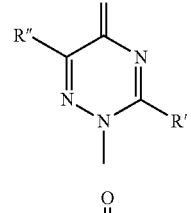

(f)

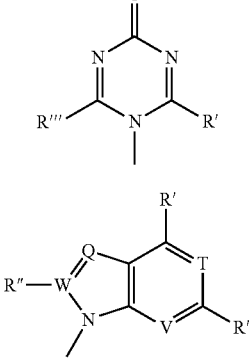

(g)

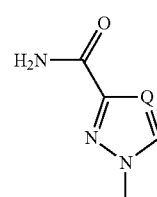

(h)

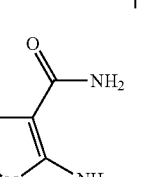

(i)

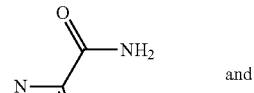

and (j)

wherein:

each R', R", R'" and R"" is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, NH$_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, CONH$_2$, CO$_2$-alkyl, CONH-alkyl, CON-dialkyl, OH, CF$_3$, CH$_2$OH, $(CH_2)_mOH$, $(CH_2)_mNH_2$, $(CH_2)_mC(OOH$, $(CH_2)_mC(N, (CH_2)_mNO_2$ and $(CH_2)_mCONH_2$;

W is C—R″ or N;

T and V independently are CH or N;

Q is CH, —CCl, —CBr, —CF, —CI, —CCN, —C—COOH, —C—CONH$_2$, or N;

$Q_1$ and $Q_2$ independently are N or C—R;

R is H, alkyl or acyl;

$Q_3$, $Q_4$, $Q_5$ and $Q_6$ independently are N or CH; and tautomeric forms thereof.

In a first subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate; (2) $R^6$ is alkyl; (3) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (4) $R^8$ and $R^{10}$ are independently H, alkyl (including lower alkyl), chlorine, bromine, or iodine; (5) X is O, S, $SO_2$ or $CH_2$; (6) $W^4$ is $CX^3$; and (7) $X^3$ is $CH_3$, $CF_3$ or $CH_2CH_3$.

In a second subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate; (2) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (3) $R^7$ and $R^9$ are independently $OR^2$; (4) $R^8$ and $R^{10}$ are independently H, alkyl (including lower alkyl), chlorine, bromine, or iodine; (5) X is O, S, $SO_2$ or $CH_2$; (6) $W^4$ is $CX^3$; and (7) $X^3$ is $CH_3$, $CF_3$ or $CH_2CH_3$.

In a third subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate; (2) $R^6$ is alkyl, alkenyl, alkynyl, Br-vinyl, hydroxy, O-alkyl, O-alkenyl, chloro, bromo, fluoro, iodo, $NO_2$, amino, loweralkylamino or di(loweralkyl)amino; (3) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (4) $R^8$ and $R^{10}$ are H; (5) X is O, S, $SO_2$ or $CH_2$; (6) $W^4$ is $CX^3$; and (7) $X^3$ is $CH_3$, $CF_3$ or $CH_2CH_3$.

In a fourth subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate; (2) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (3) $R^7$ and $R^9$ are independently $OR^2$, alkyl, alkenyl, alkynyl, Br-vinyl, O-alkenyl, chlorine, bromine, iodine, $NO_2$, amino, loweralkylamino, or di(loweralkyl)amino; (4) $R^8$ and $R^{10}$ are independently H, alkyl (including lower alkyl), chlorine, bromine, or iodine; (5) X is O; (6) $W^4$ is $CX^3$; and (7) $X^3$ is $CH_3$, $CF_3$ or $CH_2CH_3$.

In a fifth subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate;

(2) $R^6$ is alkyl; (3) $R^7$ and $R^9$ are independently $OR^1$; (4) $R^8$ and $R^{10}$ are independently H, alkyl (including lower alkyl), chlorine, bromine or iodine; (5) X is O, S, $SO_2$ or $CH_2$; (6) $W^4$ is $CX^3$; and (7) $X^3$ is $CH_3$, $CF_3$ or $CH_2CH_3$.

In a sixth subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate; (2) $R^6$ is alkyl; (3) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl)-amino; (4) $R^8$ and $R^{10}$ are H; (5) X is O, S, $SO_2$, or $CH_2$; (6) $W^4$ is $CX^3$; and (7) $X^3$ is $CH_3$, $CF_3$ or $CH_2CH_3$.

In a seventh subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate; (2) $R^6$ is alkyl; (3) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino or di(loweralkyl)-amino; (4) $R^8$ and $R^{10}$ are independently H, alkyl (including lower alkyl), chlorine, bromine or iodine; (5) X is O; (6) $W^4$ is $CX^3$; and (7) $X^3$ is $CH_3$, $CF_3$ or $CH_2CH_3$.

In a eighth subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate; (2) $R^6$ is alkyl (including lower alkyl), alkenyl, alkynyl. Br-vinyl, hydroxy, O-alkyl, O-alkenyl, chloro, bromo, fluoro, iodo, $NO_2$, amino, loweralkylamino or di(loweralkyl)amino; (3) $R^7$ and $R^9$ are independently $OR^2$; (4) $R^8$ and $R^{10}$ are hydrogen; (6) X is O, S, $SO_2$ or $CH_2$; (6) $W^4$ is $CX^3$; and (7) $X^3$ is $CH_3$, $CF_3$ or $CH_2CH_3$.

In a ninth subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate; (2) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (3) $R^7$ and $R^9$ are independently $OR^2$; (4) $R^8$ and $R^{10}$ are independently H, alkyl (including lower alkyl), chlorine, bromine or iodine; (5) X is O; (6) $W^4$ is $CX^3$; and (7) $X^3$ is $CH_3$, $CF_3$ or $CH_2CH_3$.

In a tenth subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; cholesterol; or other pharmaceutically acceptable leaving group which when administered in vivo is capable of providing a compound wherein $R^1$ is independently H or phosphate; (2) $R^6$ is alkyl (including lower alkyl), alkenyl, alkynyl, Br-vinyl, hydroxy, O-alkyl, O-alkenyl, chloro, bromo, iodo, $NO_2$, amino, loweralkylamino or di(loweralkyl)amino; (3) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (4) $R^8$ and $R^{10}$ are hydrogen; (5) X is O; (6) $W^4$ is $CX^3$; and (7) $X^3$ is $CH_3$, $CF_3$ or $CH_2CH_3$.

In an eleventh subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate; (2) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (3) $R^7$ and $R^9$ are independently $OR^2$; (4) $R^8$ and $R^{10}$ are hydrogen; (5) X is O, S, $SO_2$ or $CH_2$; (6) $W^4$ is $CX^3$; and (7) $X^3$ is $CH_3$, $CF_3$ or $CH_2CH_3$.

In a twelfth subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate; (2) $R^6$ is alkyl; (3) $R^7$ and $R^9$ are independently $OR^2$; (4) $R^8$ and $R^{10}$ are hydrogen; (5) X is O, S, $SO_2$, or $CH_2$; (6) $W^4$ is $CX^3$; and (7) $X^3$ is $CH_3$, $CF_3$ or $CH_2CH_3$.

In a thirteenth subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate; (2) $R^6$ is alkyl; (3) $R^7$ and $R^9$ are independently $OR^2$; (4) $R^8$ and $R^{10}$ are independently H, alkyl (including lower alkyl), chlorine, bromine, or iodine; (5) X is O; (6) $W^4$ is $CX^3$; and (7) $X^3$ is $CH_3$, $CF_3$ or $CH_2CH_3$.

In a fourteenth subembodiment, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which: (1) $R^1$ is independently H or phosphate; (2) $R^6$ is alkyl; (3) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (4) $R^8$ and $R^{10}$ are hydrogen; (5) X is O; (6) $W^4$ is $CX^3$; and (7) $X^3$ is $CH_3$, $CF_3$ or $CH_2CH_3$.

In even more preferred subembodiments, the compound of Formula (VI), or a pharmaceutically acceptable salt or prodrug, or a stereoisomeric, tautomeric or polymorphic form thereof, and the method for the treatment of a host infected with a Flaviviridae comprising administering an effective treatment amount of compound of Formula (VI) or a pharmaceutically acceptable salt or prodrug, or a stereoisomeric, tautomeric or polymorphic form thereof, is provided, in which:

(1) Base is 8-methyladenine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is 8-methylguanine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is 6-methylcytosine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is 6-methylthymidine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is 6-methyluracil; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is 8-methyladenine; (2) $R^1$ is phosphate; (3) $R^6$ is methyl; (4) $R^7$ and $R^9$ are hydroxyl; (5) $R^8$ and $R^{10}$ are hydrogen; and (6) X is O;

(1) Base is 8-methyladenine; (2) $R^1$ is hydrogen; (3) $R^6$ is ethyl; (4) $R^7$ and $R^9$ are hydroxyl; (5) $R^8$ and $R^{10}$ are hydrogen; and (6) X is O;

(1) Base is 8-methyladenine; (2) $R^1$ is hydrogen; (3) $R^6$ is propyl; (4) $R^7$ and $R^9$ are hydroxyl; (5) $R^8$ and $R^{10}$ are hydrogen; and (6) X is O;

(1) Base is 8-methyladenine; (2) $R^1$ is hydrogen; (3) $R^6$ is butyl; (4) $R^7$ and $R^9$ are hydroxyl; (5) $R^8$ and $R^{10}$ are hydrogen; and (6) X is O;

(1) Base is 8-methyladenine; (2) $R^1$ is hydrogen; (3) $R^6$ is methyl; (4) $R^7$ is hydrogen and $R^9$ is hydroxyl; (5) $R^8$ and $R^{10}$ are hydrogen; and (6) X is O;

(1) Base is 8-methyladenine; (2) $R^1$ is hydrogen; (3) $R^6$ is methyl; (4) $R^7$ and $R^9$ are hydroxyl; (5) $R^8$ and $R^{10}$ are hydrogen; and (6) X is S;

(1) Base is 8-methyladenine; (2) $R^1$ is hydrogen; (3) $R^6$ is methyl; (4) $R^7$ and $R^9$ are hydroxyl; (5) $R^8$ and $R^{10}$ are hydrogen; and (6) X is $SO_2$;

(1) Base is 8-methyladenine; (2) $R^1$ is hydrogen; (3) $R^6$ is methyl; (4) $R^7$ and $R^9$ are hydroxyl; (5) $R^8$ and $R^{10}$ are hydrogen; and (6) X is $CH_2$.

In a fifth principal embodiment, a compound of Formula (VIII), (IX) or (X) or a pharmaceutically acceptable salt or prodrug, or a stereoisomeric, tautomeric, or polymorphic form thereof, is provided, as well as a method for the treatment of a host infected with a Flaviviridae comprising administering an effective treatment amount of compound of Formula (VIII), (IX), or (X):

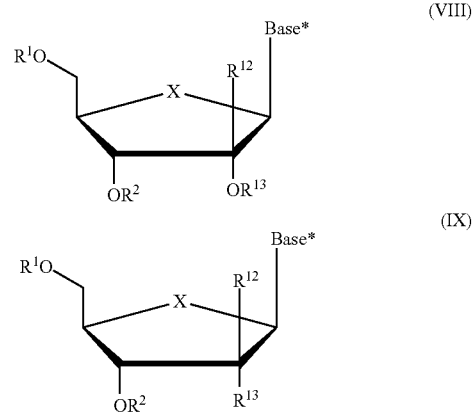

-continued

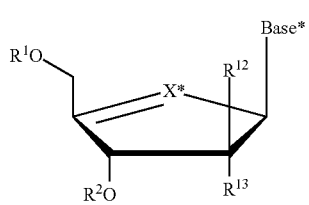
(X)

or a pharmaceutically acceptable salt or prodrug, or a stereoisomeric, tautomeric or polymorphic form thereof, wherein:
$R^1$, $R^2$, $R^3$, $R^4$, $R^5$, $Y^3$, X, and X* are as defined above;
Base* is a purine or pyrimidine base as defined herein;
each $R^{12}$ is independently a substituted alkyl (including lower alkyl), $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, substituted alkenyl, haloalkenyl (but not Br-vinyl), substituted alkynyl, haloalkynyl, —$CH_2C(O)OH$, —$CH_2C(O)OR^4$, —$CH_2C(O)O$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —$C(O)OH$, —$C(O)OR^4$, —$C(O)NH_2$, —$C(O)NHR^4$, —$C(O)NH$(lower alkyl), —$C(O)N(R^4)_2$, —$C(O)N$(lower alkyl)$_2$;
each $R^{13}$ is independently substituted alkyl (including lower alkyl), $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, substituted alkenyl, haloalkenyl (but not Br-vinyl), substituted alkynyl, haloalkynyl, optionally substituted carbocycle (preferably a 3-7 membered carbocyclic ring), optionally substituted heterocycle (preferably a 3-7 membered heterocyclic ring having one or more O, S and/or N), optionally substituted heteroaryl (preferably a 3-7 membered heteroaromatic ring having one or more O, S and/or N), —$CH_2C(O)OH$, —$CH_2C(O)OR^4$, —$CH_2C(O)O$(lower alkyl), —$CH_2C(O)SH$, —$CH_2C(O)SR^4$, —$CH_2C(O)S$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)SH$, —$(CH_2)_mC(O)SR^4$, —$(CH_2)_mC(O)S$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —$C(O)OH$, —$C(O)OR^4$, —$C(O)SH$, —$C(O)SR^4$, —$C(O)S$(lower alkyl), —$C(O)NH_2$, —$C(O)NHR^4$, —$C(O)NH$(lower alkyl), —$C(O)N(R^4)_2$, —$C(O)N$(lower alkyl)$_2$, —$O(R^4)$, —$O$(alkynyl), —$O$(aralkyl), —$O$(cycloalkyl), —$S$(acyl), —$S$(lower acyl), —$S(R^4)$, —$S$(lower alkyl), —$S$(alkenyl), —$S$(alkynyl), —$S$(aralkyl), —$S$(cycloalkyl), —$NHR^4$, —$NR^4R^5$, —$NH$(alkenyl), —$NH$(alkynyl), —$NH$(aralkyl), —$NH$(cycloalkyl), SCN, OCN, NCO or fluoro;
alternatively, $R^{12}$ and $R^{13}$ can come together to form a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N); and
each m is independently 0, 1 or 2.

In a sixth principal embodiment, a compound of Formula (XI) or (XII) or a pharmaceutically acceptable salt or prodrug, or a stereoisomeric, tautomeric, or polymorphic form thereof, is provided, as well as a method for the treatment of a host infected with a Flaviviridae comprising administering an effective treatment amount of compound of Formula (XI) or (XII):

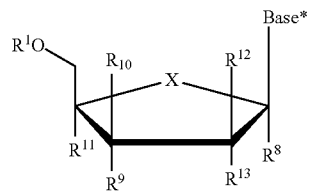
(XI)

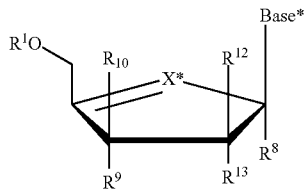
(XII)

or a pharmaceutically acceptable salt or prodrug, or a stereoisomeric, tautomeric or polymorphic form thereof, wherein:
Base*, R, $R^1$, $R^2$, $R^3$, $R^4$, $R^5$, $R^{12}$, $R^{13}$, Y, $Y^1$, $Y^2$, $Y^3$, W*, $W^1$, $W^2$, $W^3$, $W^4$, X, X*, $X^2$ and $X^3$ are as defined above;
wherein, in one embodiment, $R^8$ in Formula (XI) is —OH or —$NH_2$ only when X is carbon; and wherein;
each $R^8$ and $R^{11}$ is independently hydrogen, an optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, —$CH_2C(O)OH$, —$CH_2C(O)OR^4$, —$CH_2C(O)O$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —$C(O)OH$, —$C(O)OR^4$, —$C(O)O$(lower alkyl), —$C(O)NH_2$, —$C(O)NHR^4$, —$C(O)NH$(lower alkyl), —$C(O)N(R^4)_2$, —$C(O)N$(lower alkyl)$_2$, cyano, NH-acyl or N(acyl)$_2$;
each $R^9$ and $R^{10}$ are independently hydrogen, OH, $OR^2$, optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, optionally substituted carbocycle (preferably a 3-7 membered carbocyclic ring), optionally substituted heterocycle (preferably a 3-7 membered heterocyclic ring having one or more O, S and/or N), optionally substituted heteroaryl (preferably a 3-7 membered heteroaromatic ring having one or more O, S and/or N), —$CH_2C(O)OH$, —$CH_2C(O)OR^4$, —$CH_2C(O)O$(lower alkyl), —$CH_2C(O)SH$, —$CH_2C(O)SR^4$, —$CH_2C(O)S$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_m$ C(O)OH, —(CH₂)ₘC(O)OR⁴, —(CH₂)ₘC(O)O(lower alkyl), —(CH₂)ₘC(O)SH, —(CH₂)ₘC(O)SR⁴, —(CH₂)ₘC(O)S(lower alkyl), —(CH₂)ₘC(O)NH₂, —(CH₂)ₘC(O)NHR⁴, —(CH₂)ₘC(O)NH(lower alkyl), —(CH₂)ₘC(O)N(R⁴)₂, —(CH₂)ₘC(O)N(lower alkyl)₂, —C(O)OH, —C(O)OR⁴, —C(O)O(lower alkyl), —C(O)SH, —C(O)SR⁴, —C(O)S(lower alkyl), —C(O)NH₂, —C(O)NHR⁴, —C(O)NH(lower alkyl), —C(O)N(R⁴)₂, —C(O)N(lower alkyl)₂, —O(acyl), —O(lower acyl), —O(R⁴), —O(alkyl), —O(lower alkyl), —O(alkenyl), —O(alkynyl), —O(aralkyl), —O(cycloalkyl), —S(acyl), —S(lower acyl), —S(R⁴), —S(lower alkyl), —S(alkenyl), —S(alkynyl), —S(aralkyl), —S(cycloalkyl), NO₂, NH₂, —NH(lower alkyl), —NHR⁴, —NR⁴R⁵, —NH(acyl), —N(lower alkyl)₂, —NH(alkenyl), —NH(alkynyl), —NH(aralkyl), —NH(cycloalkyl), —N(acyl)₂, azido, cyano, SCN, OCN, NCO or halo (fluoro, chloro, bromo, iodo);

each m is independently 0, 1 or 2; and alternatively, R⁸ and R¹³, R⁹ and R¹³, R⁹ and R¹¹ or R¹⁰ and R¹² can come together to form a bridged compound selected from the group consisting of optionally substituted carbocycle (preferably a 3-7 membered carbocyclic ring) or optionally substituted heterocycle (preferably a 3-7 membered heterocyclic ring having one or more O, S and/or N); or alternatively, R¹² and R¹³ or R⁹ and R¹⁰ can come together to form a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N).

In a particular aspect of the invention, compounds of the Formula (XIII) or (XIV) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (XIII) or (XIV):

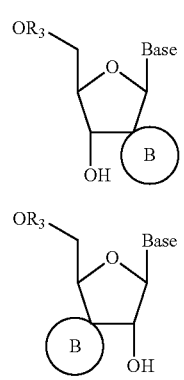

or a pharmaceutically acceptable salt or prodrug, or a stereoisomeric, tautomeric or polymorphic form thereof, wherein:

R₃ is selected from the group consisting of H; mono-, di-, and tri-phosphate or a stabilized phosphate prodrug; acyl; a sulfonate ester; optionally substituted alkyl sulfonyl; optionally substituted arylsulfonyl; a lipid; an amino acid; a carbohydrate; a peptide; cholesterol; and a pharmaceutically acceptable leaving group which when administered in vivo is capable of providing a compound wherein R₃ is independently H, or mono-, di- or triphosphate;

X″ is selected from the group consisting of one or more O, S, SO, SO₂, N, NH, NR and CH₂ wherein any of the aforementioned may be optionally substituted and may be variably positioned so as to form a 3-7 membered ring;

R is H, alkyl or acyl;

B indicates a spiro compound selected from the group consisting of optionally substituted carbocycle (preferably a 3-7 membered carbocyclic ring) or optionally substituted heterocycle (preferably a 3-7 membered heterocyclic ring having one or more O, S and/or N); and Base is selected from the group consisting of

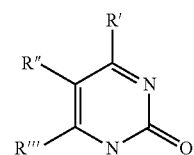
(a)

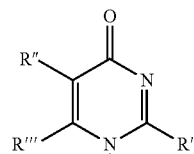
(b)

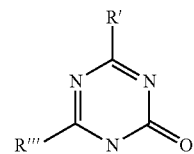
(c)

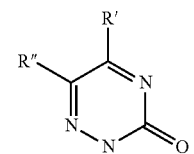
(d)

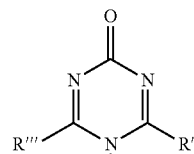
(f)

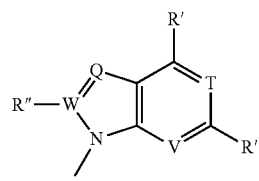
(g)

-continued (h)
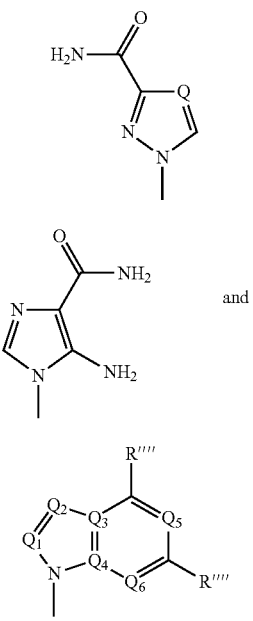

(i)

and (j)

wherein:
each R', R", R''' and R'''' are independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$ and $(CH_2)_mCONH_2$;
m is 0 or 1;
W is C—R" or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R;
R is H, alkyl or acyl;
$Q_3$, $Q_4$, $Q_5$ and $Q_6$ independently are N or CH; and
tautomeric forms thereof.

In a second particular aspect of the invention, a compound of Formula (XV), (XVI) or (XVII) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (XV), (XVI), or (XVII):

(XV)
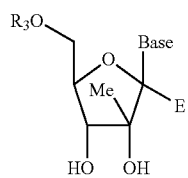

(XVI)

or (XVII)
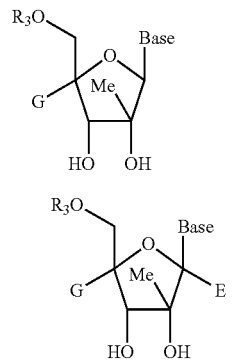

or its pharmaceutically acceptable salt or prodrug, or a stereoisomeric, tautomeric or polymorphic form thereof, wherein:
G and E independently are selected from the group consisting of H, $CH_3$, $CH_2OH$, $CH_2F$, $CH_2N_3$, $CH_2CN$, $(CH_2)_mCOOH$, $(CH_2)_mCOOR$, $(CH_2)_mCONH_2$, $(CH_2)_mCONR_2$, $(CH_2)_mCONHR$ and N-acyl;
R is H, alkyl or acyl;
m is 0 or 1; and
$R^3$ and Base are as defined for Formula (XIII).

Alternatively, for compound of Formula (XVII), at most one of G and E can further be hydrogen.

In a third particular aspect of the invention, a compound of Formula (XVIII) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (XVIII):

(XVIII)
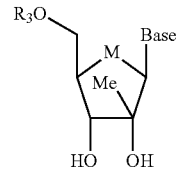

or its pharmaceutically acceptable salt or prodrug, or a stereoisomeric, tautomeric or polymorphic form thereof, wherein:
M is selected from the group consisting of S, SO, and $SO_2$; and
$R_3$ and Base are as defined for Formula (XIII).

In a fourth particular aspect of the invention, a compound of Formula (XIX), (XX), (XXI) (XXII) or (XXIII) or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (XIX), (XXI), (XXII), or (XXIII):

(XIX)
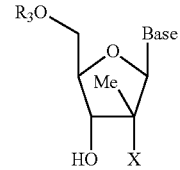

-continued

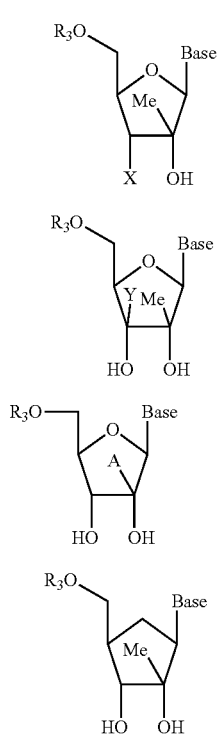

(XX)

(XXI)

or (XXII)

(XXIII)

or its pharmaceutically acceptable salt or prodrug or a stereoisomeric, tautomeric or polymorphic form thereof, wherein:

A is selected from the group consisting of optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mC(OOH)$, $(CH_2)_mCOOR$, $(CH_2)_mC(O-NH_2)$, $(CH_2)_mCONR_2$, and $(CH_2)_mCONHR$;

Y is selected from the group consisting of H, optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mCOOH$, $(CH_2)_mCOOR$, $(CH_2)_mCONH_2$, $(CH_2)_mCONR_2$, and $(CH_2)_mCONHR$;

R is H, alkyl or acyl;

X is selected from the group consisting of —OH, optionally substituted alkyl, cycloalkyl, alkenyl, alkynyl, —O-alkyl, —O-alkenyl, —O-alkynyl, —O-aryl, —O-aralkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aryl, NH-aralkyl, NH-cycloalkyl, SH, S-alkyl, S-alkenyl, S-alkynyl, S-aryl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mCOOH$, $(CH_2)_mCOOR$, $(CH_2)_mCONH_2$, $(CH_2)_mCONR_2$, $(CH_2)_mCONHR$, an optionally substituted 3-7 membered carbocyclic, and an optionally substituted 3-7 membered heterocyclic ring having O, S and/or N independently as a heteroatom taken alone or in combination;

m is 0 or 1;

$R_3$ is selected from the group consisting of H; mono-, di-, and tri-phosphate or a stabilized phosphate prodrug; substituted or unsubstituted alkyl; acyl; a sulfonate ester; optionally substituted alkyl sulfonyl; optionally substituted arylsulfonyl; a lipid; an amino acid; a carbohydrate; a peptide; cholesterol; and a pharmaceutically acceptable leaving group which when administered in vivo is capable of providing a compound wherein $R_1$ is independently H, or mono-, di- or triphosphate; and Base is a non-natural base selected from the group of:

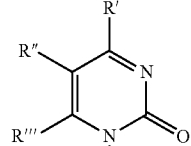
(a)

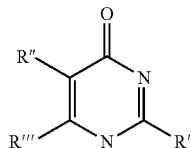
(b)

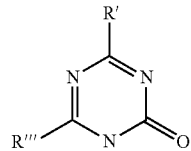
(c)

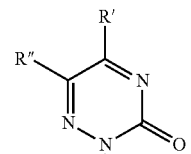
(d)

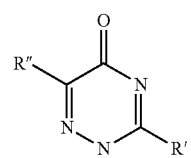
(e)

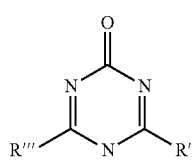
(f)

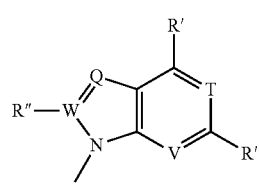
(g)

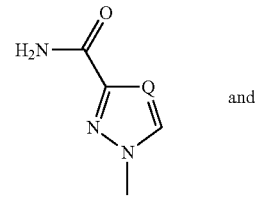
and (h)

-continued

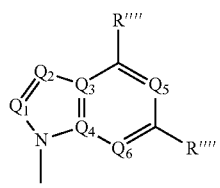
(j)

wherein:
each R', R", R''' and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mC(OOH$, $(CH_2)_mC(N$, $(CH_2)_mNO_2$ and $(CH_2)_mCONH_2$;
m is 0 or 1;
W is C—R" or N;
T and V independently are CH or N;
Q is CH, —CCl, —CBr, —CF, —CI, —CCN, —C—COOH, —C—$CONH_2$, or N;
$Q_1$ and $Q_2$ independently are N or C—R''''; and
$Q_3$, $Q_4$, $Q_5$ and $Q_6$ independently are N or CH;
with the proviso that in bases (g) and (i), R', R'''' are not H, OH, or $NH_2$; and Q, T, V, $Q_2$, $Q_5$ and $Q_6$ are not N.

In another preferred embodiment, a compound of Formula (IX), or a pharmaceutically acceptable salt or prodrug, or a stereoisomeric, tautomeric or polymorphic form thereof, is provided, as well as a method for the treatment of a host infected with a Flaviviridae comprising administering an effective treatment amount of compound of Formula (IX):

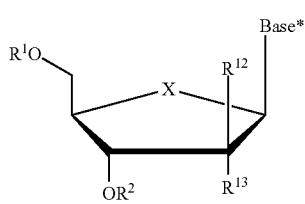
(IX)

or a stereoisomeric, tautomeric or polymorphic form thereof, or a pharmaceutically acceptable salt thereof, wherein:
$R^1$, $R^2$ and $R^3$ are independently H; phosphate; straight chained, branched or cyclic alkyl; acyl; CO-alkyl; CO-aryl; CO-alkoxyalkyl; CO-aryloxyalkyl; CO-substituted aryl; sulfonate ester; benzyl, wherein the phenyl group is optionally substituted with one or more substituents; alkylsulfonyl; arylsulfonyl; aralkylsulfonyl; a lipid; an amino acid; a carbohydrate; a peptide; cholesterol; or a pharmaceutically acceptable leaving group which when administered in vivo is capable of providing a compound wherein $R^1$, $R^2$ and/or $R^3$ is independently H or phosphate;
X is O, S, $SO_2$ or $CH_2$;
Base* is a purine or pyrimidine base;
$R^{12}$ is $C(Y^3)_3$;
$Y^3$ is independently H, F, Cl, Br or I; and
$R^{13}$ is fluoro.

In one subembodiment X is O, and $Y^3$ is H. In another subembodiment, when X is O and $Y^3$ is H, $R^1$, $R^2$ and $R^3$ are also H.

II. Stereochemistry

It is appreciated that nucleosides of the present invention have several chiral centers and may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein. It being well known in the art how to prepare optically active forms (for example, by resolution of the racemic form by recrystallization techniques, by synthesis from optically-active starting materials, by chiral synthesis, or by chromatographic separation using a chiral stationary phase).

In particular, since the 1' and 4' carbons of the nucleoside are chiral, their nonhydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a nonnaturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the nonnaturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.
i) physical separation of crystals—a technique whereby macroscopic crystals of the individual enantiomers are manually separated. This technique can be used if crystals of the separate enantiomers exist, i.e., the material is a conglomerate, and the crystals are visually distinct;
ii) simultaneous crystallization—a technique whereby the individual enantiomers are separately crystallized from a solution of the racemate, possible only if the latter is a conglomerate in the solid state;
iii) enzymatic resolutions—a technique whereby partial or complete separation of a racemate by virtue of differing rates of reaction for the enantiomers with an enzyme;
iv) enzymatic asymmetric synthesis—a synthetic technique whereby at least one step of the synthesis uses an enzymatic reaction to obtain an enantiomerically pure or enriched synthetic precursor of the desired enantiomer;
v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;
vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

III. Definitions

The term "alkyl", as used herein, unless otherwise specified, refers to a saturated straight, branched, or cyclic, primary, secondary, or tertiary hydrocarbon of typically $C_1$ to $C_{10}$, and specifically includes methyl, $CF_3$, $CCl_3$, $CFCl_2$, $CF_2Cl$, ethyl, $CH_2CF_3$, $CF_2CF_3$, propyl, isopropyl, cyclopropyl, butyl, isobutyl, secbutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups, and particularly includes halogenated alkyl groups, and even more particularly fluorinated alkyl groups. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "lower alkyl", as used herein, and unless otherwise specified, refers to a $C_1$ to $C_4$ saturated straight, branched, or if appropriate, a cyclic (for example, cyclopropyl) alkyl group, including both substituted and unsubstituted moieties.

The term "alkylamino" or "arylamino" refers to an amino group that has one or two alkyl or aryl substituents, respectively. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "aryl", as used herein, and unless otherwise specified, refers to phenyl, biphenyl, or naphthyl, and preferably phenyl. The term includes both substituted and unsubstituted moieties. The aryl group can be substituted with any described moiety, including, but not limited to, one or more moieties selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "alkaryl" or "alkylaryl" refers to an alkyl group with an aryl substituent.

The term aralkyl or arylalkyl refers to an aryl group with an alkyl substituent.

The term "halo", as used herein, includes chloro, bromo, iodo, and fluoro. The term "purine" or "pyrimidine" base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-alkylaminopurine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-iodo-pyrimidine, $C^5$-Br-vinyl pyrimidine, $C^6$-Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" refers to a group of the formula C(O)R', wherein R' is an straight, branched, or cyclic alkyl (including lower alkyl), amino acid, aryl including phenyl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclopropylacetyl, cyclopropyl carboxy, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoroheptanoyl, 7H-dodeca-fluoroheptanoyl, 7-chlorododecafluoro-heptanoyl, 7-chloro-dodecafluoro-heptanoyl, 7H-dodecafluoroheptanoyl, 7H-dodeca-fluoro-heptanoyl, nonafluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxybenzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl. When the term acyl is used, it is meant to be a specific and independent disclosure of acetyl, trifluoroacetyl, methylacetyl, cyclopropylacetyl, propionyl, butyryl, hexanoyl, heptanoyl, octanoyl, neo-heptanoyl, phenylacetyl, diphenylacetyl, α-trifluoromethyl-phenylacetyl, bromoacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, 2-thiopheneacetyl, tert-butylacetyl, trichloroacetyl, monochloro-acetyl, dichloroacetyl, methoxybenzoyl, 2-bromo-propionyl, decanoyl, n-pcntadecanoyl, stearyl, 3-cyclopentyl-propionyl, 1-benzene-carboxyl, pivaloyl acetyl, 1-adamantane-carboxyl, cyclohexane-carboxyl, 2,6-pyridinedicarboxyl, cyclopropane-carboxyl, cyclobutane-carboxyl, 4-methylbenzoyl, crotonyl, 1-methyl-1H-indazole-3-carbonyl, 2-propenyl, isovaleryl, 4-phenylbenzoyl.

The term "amino acid" includes naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. Tables 1-24 set out examples of species within the present invention. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L configurations.

As used herein, the term "substantially free of" or "substantially in the absence of" refers to a nucleoside composition that includes at least 85 or 90% by weight, preferably 95%, 98%, 99% or 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85%, 90%, 95%, 98%, 99%, or 100% by weight, of the nucleoside, the remainder comprising other chemical species or enantiomers.

The term "host", as used herein, refers to an unicellular or multicellular organism in which the virus can replicate, including cell lines and animals, and preferably a human. Alternatively, the host can be carrying a part of the Flaviviridae viral genome, whose replication or function can be altered by the compounds of the present invention. The term host specifically refers to infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

The term "pharmaceutically acceptable salt or prodrug" is used throughout the specification to describe any pharmaceutically acceptable form (such as an ester, phosphate ester, salt of an ester or a related group) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against a Flaviviridae, or are metabolized to a compound that exhibits such activity.

IV. Prodrugs and Derivatives

The active compound can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts"), and a compound, which has been alkylated, acylated, or otherwise modified at the 5'-position, or on the purine or pyrimidine base (a type of "pharmaceutically acceptable prodrug"). Further, the modifications can affect the biological activity of the compound, in some cases increasing the activity over the parent compound.

This can easily be assessed by preparing the salt or prodrug and testing its antiviral activity according to the methods described herein, or other methods known to those skilled in the art.

A. Pharmaceutically Acceptable Salts

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed by addition of acids, which form a physiological acceptable anion, for example, tosylate, methanesulfonate, acetate, citrate, malonate, tartarate, succinate, benzoate, ascorate, α-ketoglutarate, α-glycerophosphate, formate, fumarate, propionate, glycolate, lactate, pyruvate, oxalate, maleate, and salicylate. Suitable inorganic salts may also be formed, including, sulfate, nitrate, bicarbonate, carbonate salts, hydrobromate and phosphoric acid. In a preferred embodiment, the salt is a mono- or di-hydrochloride salt.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made. In one embodiment, the salt is a hydrochloride salt of the compound. In another embodiment, the pharmaceutically acceptable salt is a dihydrochloride salt.

B. Nucleotide Prodrug Formulations

The nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono-, di- or triphosphate of the nucleoside reduces polarity and allows passage into cells. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischoferger, *Antiviral Research,* 1995, 27:1-17. Any of these can be used in combination with the disclosed nucleosides to achieve a desired effect.

In an alternative embodiment, the nucleoside is delivered as a phosphonate or a SATE derivative.

The active nucleoside can also be provided as a 2', 3' and/or 5'-phosphoether lipid or a 2', 3' and/or 5'-ether lipid. Nonlimiting examples are described include the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hostetler, K. Y., D. D. Richman, D. A. Carson, L. M. Stuhmiller, G. M. T. van Wijk, and H. van den Bosch. 1992. "Greatly enhanced inhibition of human immunodeficiency virus type replication in CEM and HT4-6C cells by 3'-deoxythymine diphosphate dimyristoylglycerol, a lipid prodrug of 3,-deoxythymine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymine and other antiviral nucleosides." *J. Biol. Chem.* 265:61127.

Nonlimiting examples of U.S. patents that disclose suitable lipophilic substituents that can be covalently incorporated into the nucleoside, preferably at the 2', 3' and/or 5'-OH position of the nucleoside or lipophilic preparations, include U.S. Pat. Nos. 5,149,794 (Sep. 22, 1992, Yatvin et al.); 5,194,654 (Mar. 16, 1993, Hostetler et al., 5,223,263 (Jun. 29, 1993, Hostetler et al.); 5,256,641 (Oct. 26, 1993, Yatvin et al.); 5,411,947 (May 2, 1995, Hostetler et al.); 5,463,092 (Oct. 31, 1995, Hostetler et al.); 5,543,389 (Aug. 6, 1996, Yatvin et al.); 5,543,390 (Aug. 6, 1996, Yatvin et al.); 5,543,391 (Aug. 6, 1996, Yatvin et al.); and 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Aryl esters, especially phenyl esters, are also provided. Nonlimiting examples are disclosed in DeLambert et al., J. Med. Chem. 37: 498 (1994). Phenyl esters containing a carboxylic ester ortho to the phosphate are also provided. Khamnei and Torrence, J. Med. Chem.; 39:4109-4115 (1996). In particular, benzyl esters, which generate the parent compound, in some cases using substituents at the ortho- or para-position to accelerate hydrolysis, are provided. Examples of this class of prodrugs are described by Mitchell et al., J. Chem. Soc. Perkin Trans. 12345 (1992); Brook, et al. WO 91/19721; and Glazier et al. WO 91/19721.

Cyclic and noncyclic phosphonate esters are also provided. Nonlimiting examples are disclosed in Hunston et al., J. Med. Chem. 27: 440-444 (1984) and Starrett et al. J. Med. Chem. 37: 1857-1864 (1994). Additionally, cyclic 3',5'-phosphate esters are provided. Nonlimiting examples are disclosed in Meier et al. J. Med. Chem. 22: 811-815 (1979). Cyclic 1',3'-propanyl phosphonate and phosphate esters, such as ones containing a fused aryl ring, i.e. the cyclosaligenyl ester, are also provided (Meier et al., Bioorg. Med. Chem. Lett. 7: 99-104 (1997)). Unsubstituted cyclic 1',3'-propanyl esters of the monophosphates are also provided (Farquhar et al., 3. Med. Chem. 26: 1153 (1983); Farquhar et al., J. Med. Chem. 28: 1358 (1985)) were prepared. In addition, cyclic 1',3'-propanyl esters substituted with a pivaloyloxy methyloxy group at C-1' are provided (Freed et al., Biochem. Pharmac. 38: 3193 (1989); Biller et al., U.S. Pat. No. 5,157,027).

Cyclic phosphoramidates are known to cleave in vivo by an oxidative mechanism. Therefore, in one embodiment of the present invention, a variety of substituted 1',3' propanyl cyclic phosphoramidates are provided. Non-limiting examples are disclosed by Zon, Progress in Med. Chem. 19, 1205 (1982). Additionally, a number of 2'- and 3'-substituted proesters are provided. 2'-Substituents include methyl, dimethyl, bromo, trifluoromethyl, chloro, hydroxy, and methoxy; 3'-substituents including phenyl, methyl, trifluoromethyl, ethyl, propyl, i-propyl, and cyclohexyl. A variety of 1'-substituted analogs are also provided.

Cyclic esters of phosphorus-containing compounds are also provided. Non-limiting examples are described in the following:

[1] di and tri esters of phosphoric acids as reported in Nifantyev et al., Phosphorus, Sulfur Silicon and Related Eelements, 113: 1 (1996); Wijnberg et al., EP-180276 A1;

[2] phosphorus (III) acid esters. Kryuchkov et al., Izv. Akad. Nauk SSSR, Ser. Khim. 6: 1244 (1987). Some of the compounds were claimed to be useful for the asymmetric synthesis of L-Dopa precursors. Sylvain et al., DE3512781 A1;

[3] phosphoramidates. Shih et al., Bull. Inst. Chem. Acad. Sin, 41: 9 (1994); Edmundson et al., J. Chem. Res. Synop. 5: 122 (1989); and

[4] phosphonates. Neidlein et al., Heterocycles 35: 1185 (1993).

Further, nonlimiting examples of U.S. and International Patent Applications that disclose suitable cyclic phosphoramidate prodrugs include U.S. Pat. No. 6,312,662; WO 99/45016; WO 00/52015; WO 01/47935; and WO 01/18013 to Erion, et al. from Metabasis Therapeutics, Inc. Specifically, prodrugs of the formula below are provided:

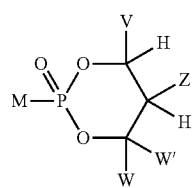

(A*)

wherein:
together V and Z are connected via an additional 3-5 atoms to form a cyclic group containing 5-7 atoms, optionally 1 heteroatom, substituted with hydroxy, acyloxy, alkoxycarbonyloxy, or aryloxycarbonyloxy attached to a carbon atom that is three atoms from both O groups attached to the phosphorus; or together V and Z are connected via an additional 3-5 atoms to form a cyclic group, optionally containing 1 heteroatom, that is fused to an aryl group at the beta and gamma position to the O attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from an O attached to the phosphorus;

together Z and W are connected via an additional 3-5 atoms to form a cyclic group, optionally containing one heteroatom, and V must be aryl, substituted aryl, heteroaryl, or substituted heteroaryl;

together W and W' are connected via an additional 2-5 atoms to form a cyclic group, optionally containing 0-2 heteroatoms, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$^2$ aryl, —CH(aryl)OH, —CH(CH=CR$^2$$_2$)OH, —CH(C.ident.CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{12}$, and —(CH$_2$)$_p$—SR$^{12}$;

p is an integer 2 or 3;

with the provisos that:
a) V, Z, W, W' are not all —H; and
b) when Z is —R$^2$, then at least one of V, W, and W' is not —H, alkyl, aralkyl, or alicyclic;

R$^2$ is selected from the group consisting of R$^3$ and —H;
R$^3$ is selected from the group consisting of alkyl, aryl, alicyclic, and aralkyl;
R$^{12}$ is selected from the group consisting of —H, and lower acyl;
M is the biologically active agent, and that is attached to the phosphorus in formula I via the 2', 3' and/or 5'-hydroxyl.

V. Combination or Alternation Therapy

The active compounds of the present invention can be administered in combination or alternation with another anti-flavivirus or pestivirus agent, or in particular an anti-HCV agent to treat any of the conditions described herein. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In preferred embodiments, an anti-HCV (or anti-pestivirus or anti-flavivirus) compound that exhibits an EC$_{50}$ of 10-15 µM, or preferably less than 1-5 µM, is desirable.

It has been recognized that drug-resistant variants of flaviviruses, pestiviruses or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Any of the viral treatments described in the Background of the Invention can be used in combination or alternation with the compounds described in this specification. Nonlimiting examples include:

1) Protease inhibitors

Examples include substrate-based NS3 protease inhibitors (Attwood et al., Antiviral peptide derivatives, PCT WO 98/22496, 1998; Attwood et al., Antiviral Chemistry and Chemotherapy 1999, 10, 259-273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734); Non-substrate-based NS3 protease inhibitors such as 2,4,6-trihydroxy-3-nitro-benzamide derivatives (Sudo K. et al., Biochemical and Biophysical Research Communications, 1997, 238, 643-647; Sudo K. et al. Antiviral Chemistry and Chemotherapy, 1998, 9, 186), including RD3-4082 and RD3-4078, the former substituted on the amide with a 14 carbon chain and the latter processing a para-phenoxyphenyl group; and Sch 68631, a phenanthrenequinone, an HCV protease inhibitor (Chu M. et al., Tetrahedron Letters 37:7229-7232, 1996).

Sch 351633, isolated from the fungus *Penicillium griseofulvum*, was identified as a protease inhibitor (Chu M. et al., Bioorganic and Medicinal Chemistry Letters 9:1949-1952). Eglin c, isolated from leech, is a potent inhibitor of several serine proteases such as *S. griseus* proteases A and B, α-chymotrypsin, chymase and subtilisin. Qasim M. A. et al., Biochemistry 36:1598-1607, 1997.

U.S. patents disclosing protease inhibitors for the treatment of HCV include, for example, U.S. Pat. No. 6,004,933 to Spruce et al. which discloses a class of cysteine protease inhibitors for inhibiting HCV endopeptidase 2; U.S. Pat. No. 5,990,276 to Zhang et al. which discloses synthetic inhibitors of hepatitis C virus NS3 protease; U.S. Pat. No. 5,538,865 to Reyes et a; WO 02/008251 to Corvas International, Inc, and WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 to Schering Corporation. Imidazoleidinones as NS3 serine protease inhibitors of HCV are disclosed in WO 02/08198 to Schering Corporation and WO 02/48157 to Bristol Myers Squibb. WO 98/17679 to Vertex Pharmaceuticals and WO 02/48116 to Bristol Myers Squibb also disclose HCV protease inhibitors.

2) Thiazolidine derivatives which show relevant inhibition in a reverse-phase HPLC assay with an NS3/4A fusion protein and NS5A/5B substrate (Sudo K. et al., Antiviral Research, 1996, 32, 9-18), especially compound RD-1-6250, possessing a fused cinnamoyl moiety substituted with a long alkyl chain, RD4 6205 and RD4 6193;

3) Thiazolidines and benzanilides identified in Kakiuchi N. et al. J. EBS Letters 421, 217-220; Takeshita N. et al. Analytical Biochemistry, 1997, 247, 242-246;

4) A phenan-threnequinone possessing activity against protease in a SDS-PAGE and autoradiography assay isolated from the fermentation culture broth of *Streptomyces* sp., Sch 68631 (Chu M. et al., Tetrahedron Letters, 1996, 37, 7229-7232), and Sch 351633, isolated from the fungus *Penicillium griseofulvum*, which demonstrates activity in a scintillation proximity assay (Chu M. et al., Bioorganic and Medicinal Chemistry Letters 9, 1949-1952);

5) Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

6) Nucleotide polymerase inhibitors and gliotoxin (Ferrari R. et al. Journal of Virology, 1999, 73, 1649-1654), and the natural product cerulenin (Lohmann V. et al., Virology, 1998, 249, 108-118);

7) Antisense phosphorothioate oligodeoxynucleotides (S-ODN) complementary to sequence stretches in the 5' non-coding region (NCR) of the virus (Alt M. et al., Hepatology, 1995, 22, 707-717), or nucleotides 326-348 comprising the 3' end of the NCR and nucleotides 371-388 located in the core coding region of the HCV RNA (Alt M. et al., Archives of Virology, 1997, 142, 589-599; Galderisi U. et al., Journal of Cellular Physiology, 1999, 181, 251-257);

8) Inhibitors of IRES-dependent translation (Ikeda N et al., Agent for the prevention and treatment of hepatitis C, Japanese Patent Pub. JP-08268890; Kai Y. et al. Prevention and treatment of viral diseases, Japanese Patent Pub. JP-10101591);

9) Ribozymes, such as nuclease-resistant ribozymes (Maccjak, D. J. et al., Hepatology 1999, 30, abstract 995) and those disclosed in U.S. Pat. No. 6,043,077 to Barber et al., and U.S. Pat. Nos. 5,869,253 and 5,610,054 to Draper et al.; and 10) Nucleoside analogs have also been developed for the treatment of Flaviviridae infections.

11) any of the compounds described by Idenix Pharmaceuticals in International Publication Nos. WO 01/90121 and WO 01/92282;

12) Compound in other patent applications disclosing the use of certain nucleoside analogs to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc., PCT/EP01/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48165 by Pharmasset, Ltd.

13) PCT Publication No. WO 99/43691 to Emory University, entitled "2'-Fluoronucleosides" discloses the use of certain 2'-fluoronucleosides to treat HCV.

14) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperidenes (U.S. Pat. No. 5,830,905 to Diana et al.).

15) Other compounds currently in preclinical or clinical development for treatment of hepatitis c virus include: Interleukin-10 by Schering-Plough, IP-501 by Interneuron, Merimebodib (VX-497) by Vertex, AMANTADINE® (Symmetrel) by Endo Labs Solvay, HEPTAZYME® by RPI, IDN-6556 by Idun Pharma., XTL-002 by XTL., HCV/MF59 by Chiron, CIVACIR® (Hepatitis C Immune Globulin) by NABI, LEVOVIRIN® by ICN/Ribapharm, VIRAMIDINE® by ICN/Ribapharm, ZADAXIN® (thymosin alpha-1) by Sci Clone, thymosin plus pegylated interferon by Sci Clone, CEPLENE® (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc., JTK 003 by AKROS Pharma, BILN-2061 by Boehringer Ingelheim, CellCept (mycophenolate mofetil) by Roche, T67, a β-tubulin inhibitor, by Tularik, a therapeutic vaccine directed to E2 by Innogenetics, FK788 by Fujisawa Healthcare, Inc., IdB 1016

(Siliphos, oral silybin-phosphatdylcholine phytosome), RNA replication inhibitors (VP50406) by ViroPharma/Wyeth, therapeutic vaccine by Intercell, therapeutic vaccine by Epimmune/Genencor, IRES inhibitor by Anadys, ANA 245 and ANA 246 by Anadys, immunotherapy (Therapore) by Avant, protease inhibitor by Corvas/SChering, helicase inhibitor by Vertex, fusion inhibitor by Trimeris, T cell therapy by CellExSys, polymerase inhibitor by Biocryst, targeted RNA chemistry by PTC Therapeutics, Dication by Immtech, Int., protease inhibitor by Agouron, protease inhibitor by Chiron/Medivir, antisense therapy by AVI BioPharma, antisense therapy by Hybridon, hemopurifier by Aethlon Medical, therapeutic vaccine by Merix, protease inhibitor by Bristol-Myers Squibb/Axys, Chron-VacC, a therapeutic vaccine, by Tripep, Utah 231B by United Therapeutics, protease, helicase and polymerase inhibitors by Genelabs Technologies, IRES inhibitors by Immusol, R803 by Rigel Pharmaceuticals, INFERGEN® (interferon alphacon-1a) by InterMune, OMNIFERON® (natural interferon) by Viragen, ALBUFERON® by Human Genome Sciences, REBIF® (interferon beta-1a) by Ares-Serono, Omega Interferon by BioMedicine, Oral Interferon Alpha by Amarillo Biosciences, interferon gamma, interferon tau, and Interferon gamma-1b by InterMune.

VI. Pharmaceutical Compositions

Hosts, including humans, infected with pestivirus, flavivirus, HCV infection, or any other condition described herein, or another organism replicating through a RNA-dependent RNA viral polymerase, or for treating any other disorder described herein, can be treated by administering to the patient an effective amount of the active compound or a pharmaceutically acceptable prodrug or salt thereof in the presence of a pharmaceutically acceptable carrier or dilutent. The active materials can be administered by any appropriate route, for example, orally, parenterally, intravenously, intradermally, subcutaneously, or topically, in liquid or solid form.

A preferred dose of the compound for pestivirus, flavivirus or HCV will be in the range from about 1 to 50 mg/kg, preferably 1 to 20 mg/kg, of body weight per day, more generally 0.1 to about 100 mg per kilogram body weight of the recipient per day. Lower doses may be preferable, for example doses of 0.5-100 mg, 0.5-50 mg, 0.5-10 mg, or 0.5-5 mg per kilogram body weight per day. Even lower doses may be useful, and thus ranges can include from 0.1-0.5 mg per kilogram body weight per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3000 mg, preferably 70 to 1400 mg of active ingredient per unit dosage form. An oral dosage of 50-1000 mg is usually convenient, including in one or multiple dosage forms of 50, 100, 200, 250, 300, 400, 500, 600, 700, 800, 900 or 1000 mgs. Lower doses may be preferable, for example from 10-100 or 1-50 mg. Also contemplated are doses of 0.1-50 mg, or 0.1-20 mg or 0.1-10.0 mg. Furthermore, lower doses may be utilized in the case of administration by a non-oral route, as, for example, by injection or inhalation.

Ideally the active ingredient should be administered to achieve peak plasma concentrations of the active compound of from about 0.2 to 70 µM, preferably about 1.0 to 10 µM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, sucutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VII. Processes for the Preparation of Active Compounds

The nucleosides of the present invention can be synthesized by any means known in the art. In particular, the synthesis of the present nucleosides can be achieved by either alkylating the appropriately modified sugar, followed by glycosylation or glycosylation followed by alkylation of the nucleoside. The following non-limiting embodiments illustrate some general methodology to obtain the nucleosides of the present invention.

A. General Synthesis of 1'-C-Branched Nucleosides

1'-C-Branched ribonucleosides of the following structure:

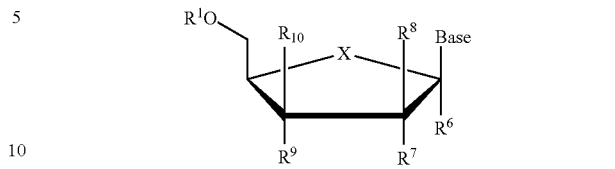

wherein Base, $R^1$, $R^2$, $R^3$, $R^4$, $R^5$, $R^6$, $R^7$, $R^8$, $R^9$, $R^{10}$, Y, $W^1$, $W^2$, $W^3$, X, $X^1$, $X^2$ and $X^3$ are as defined herein can be prepared by one of the following general methods.

I) Modification from the Lactone

The key starting material for this process is an appropriately substituted lactone. The lactone can be purchased or can be prepared by any known means including standard epimerization, substitution and cyclization techniques. The lactone can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991. The protected lactone can then be coupled with a suitable coupling agent, such as an organometallic carbon nucleophile, such as a Grignard reagent, an organolithium, lithium dialkylcopper or $R^6$—$SiMe_3$ in TBAF with the appropriate non-protic solvent at a suitable temperature, to give the 1'-alkylated sugar.

The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 1'-C-branched ribonucleoside is desired. The synthesis of a ribonucleoside is shown in Scheme 1. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 1

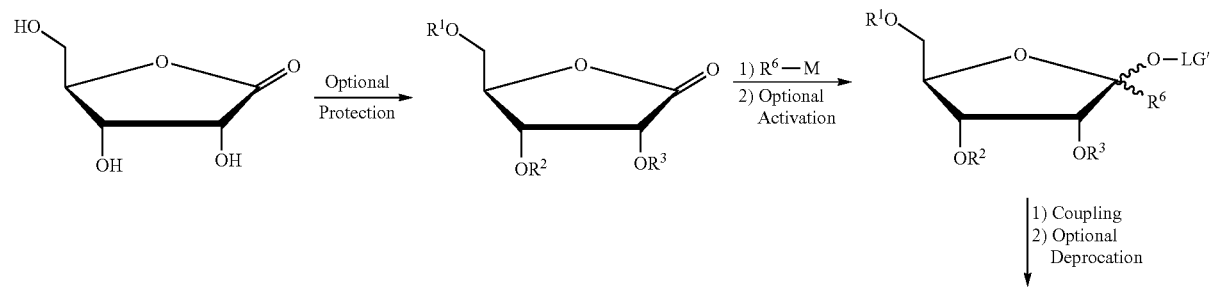

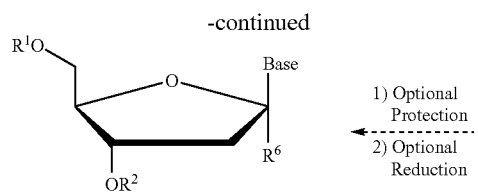
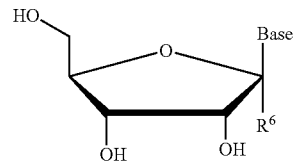

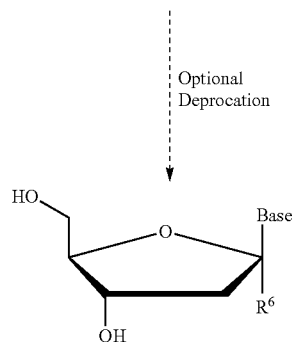

2. Alternative Method for the Preparation of 1'-C-Branched Nucleosides

The key starting material for this process is an appropriately substituted hexose. The hexose can be purchased or can be prepared by any known means including standard epimerization (e.g. via alkaline treatment), substitution and coupling techniques. The hexose can be selectively protected to give the appropriate hexa-furanose, as taught by Townsend *Chemistry of Nucleosides and Nucleotides*, Plenum Press, 1994.

The 1'-hydroxyl can be optionally activated to a suitable leaving group such as an acyl group or a halogen via acylation or halogenation, respectively. The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

The 1'-$CH_2$—OH, if protected, can be selectively deprotected by methods well known in the art. The resultant primary hydroxyl can be functionalized to yield various C-branched nucleosides. For example, the primary hydroxyl can be reduced to give the methyl, using a suitable reducing agent. Alternatively, the hydroxyl can be activated prior to reduction to facilitate the reaction; i.e. via the Barton reduction. In an alternate embodiment, the primary hydroxyl can be oxidized to the aldehyde, then coupled with a carbon nucleophile, such as a Grignard reagent, an organolithium, lithium dialkylcopper or $R^6$—$SiMe_3$ in TBAF with the appropriate non-protic solvent at a suitable temperature.

In a particular embodiment, the 1'-C-branched ribonucleoside is desired. The synthesis of a ribonucleoside is shown in Scheme 2. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction: i.e. via the Barton reduction.

Scheme 2

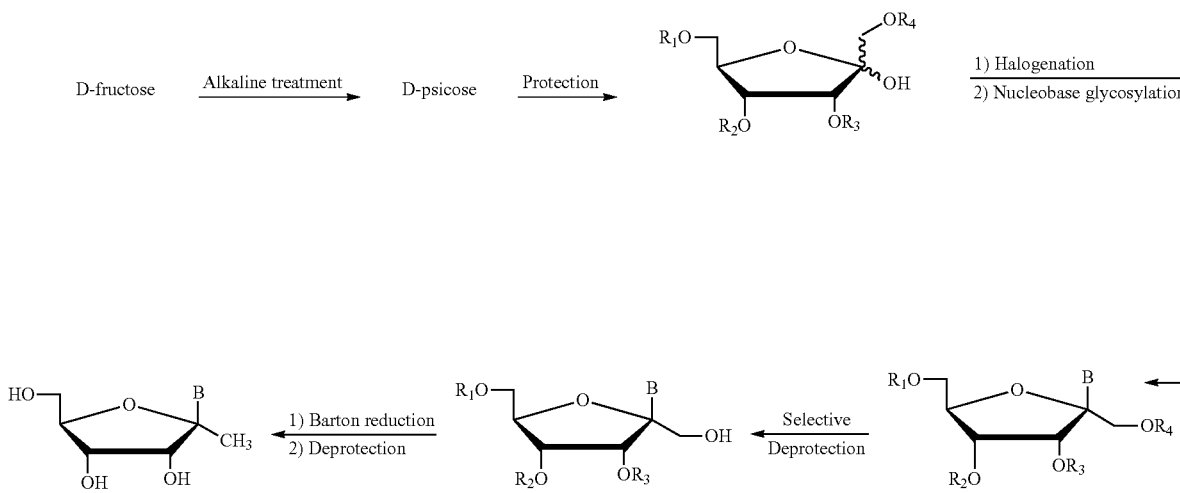

In addition, the L-enantiomers corresponding to the compounds of the invention can be prepared following the same general methods (1 or 2), beginning with the corresponding L-sugar or nucleoside L-enantiomer as starting material.

B. General Synthesis of 2'-C-Branched Nucleosides

2'-C-Branched ribonucleosides of the following structure:

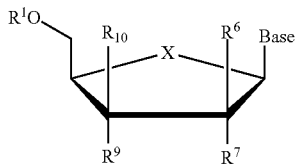

wherein Base, $R^1$, $R^2$, $R^3$, $R^4$, $R^5$, $R^6$, $R^7$, $R^9$, $R^{10}$, Y, $W^1$, $W^2$, $W^3$, X, $X^1$, $X^2$ and $X^3$ are as defined herein can be prepared by one of the following general methods.

1. Glycosylation of the Nucleobase with an Appropriately Modified Sugar

The key starting material for this process is an appropriately substituted sugar with a 2'-OH and 2'-H, with the appropriate leaving group (LG), for example an acyl group or a halogen. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $CH_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or $R^6$—$SiMe_3$ in TBAF with the ketone with the appropriate non-protic solvent at a suitable temperature, yields the 2'-alkylated sugar. The alkylated sugar can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991.

The optionally protected sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 3. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 3

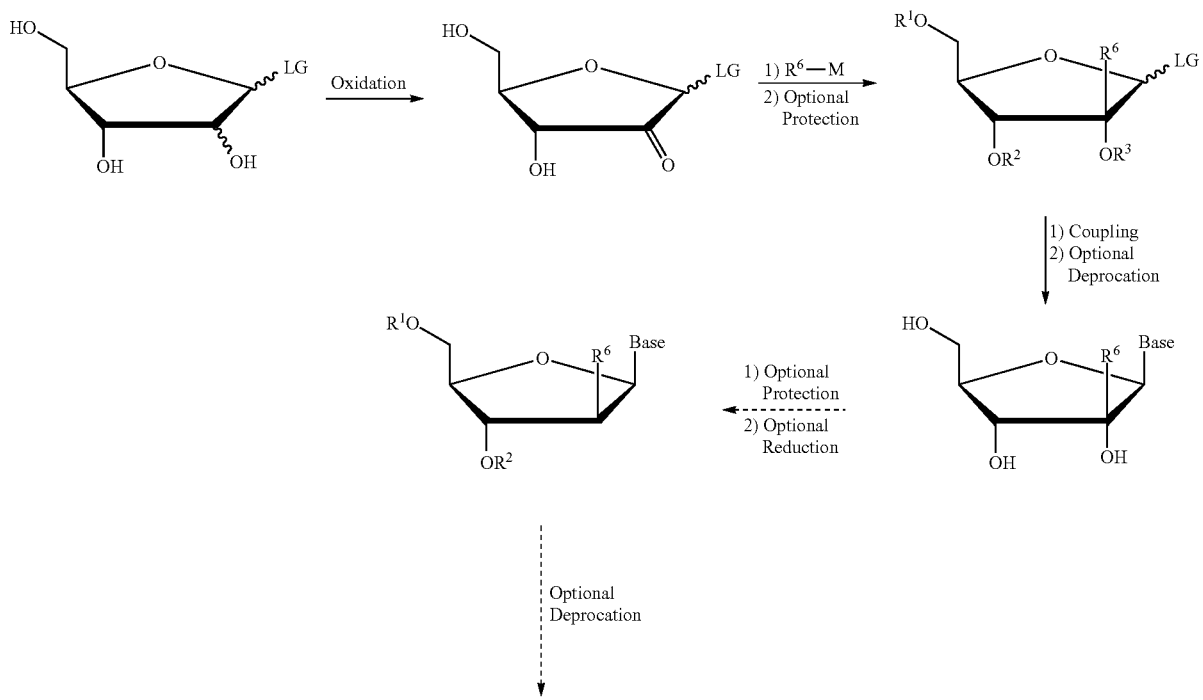

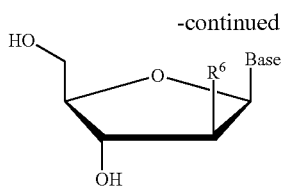

2. Modification of a Pre Formed Nucleoside

The key starting material for this process is an appropriately substituted nucleoside with a 2'-OH and 2'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $CH_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as taught by GreeneGreene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 4. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 4

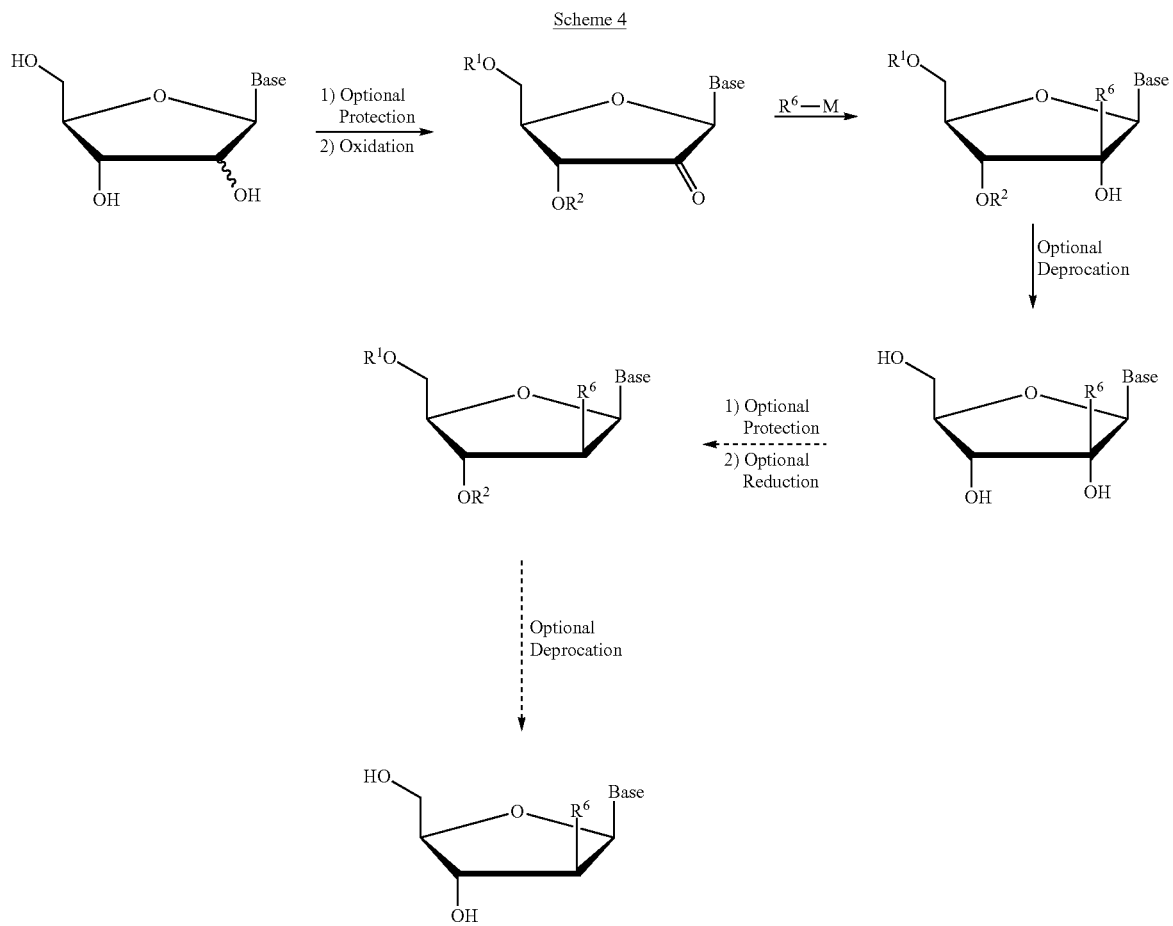

In another embodiment of the invention, the L-enantiomers are desired. Therefore, the L-enantiomers can be corresponding to the compounds of the invention can be prepared following the same foregoing general methods, beginning with the corresponding L-sugar or nucleoside L-enantiomer as starting material.

C. General Synthesis of 3'-C-Branched Nucleosides

3'-C-Branched ribonucleosides of the following structure:

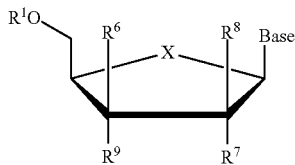

wherein Base, $R^1$, $R^2$, $R^3$, $R^4$, $R^5$, $R^6$, $R^7$, $R^8$, $R^9$, Y, $W^1$, $W^2$, $W^3$, X, $X^1$, $X^2$ and $X^3$ are as defined herein can be prepared by one of the following general methods.

1 Glycosylation of the Nucleobase with an Appropriately Modified Sugar

The key starting material for this process is an appropriately substituted sugar with a 3'-OH and 3'-H, with the appropriate leaving group (LG), for example an acyl group or a halogen. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 3'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $CH_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or $R^6$—$SiMe_3$ in TBAF with the ketone with the appropriate non-protic solvent at a suitable temperature, yields the 3'-C-branched sugar. The 3'-C-branched sugar can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991.

The optionally protected sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 3'-C-branched ribonucleoside is desired. The synthesis of a ribonucleoside is shown in Scheme 5. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 5

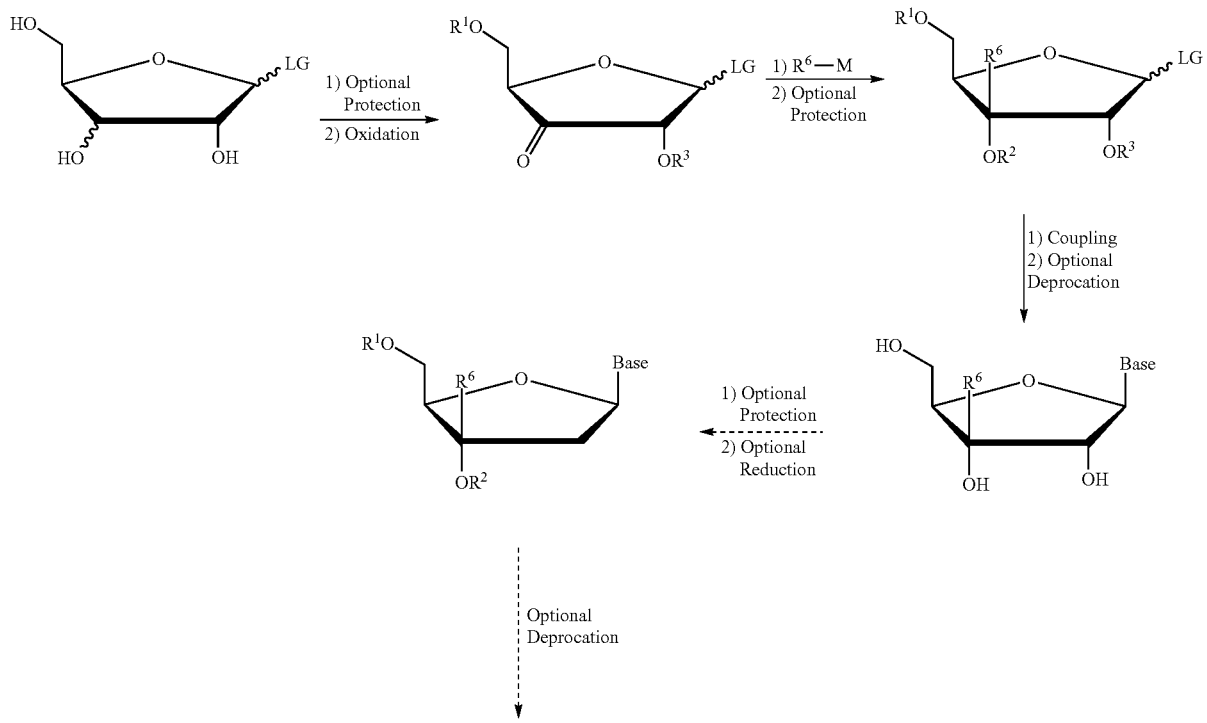

-continued

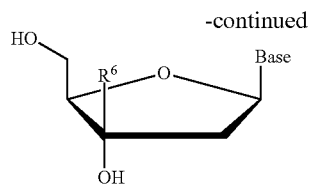

2. Modification of a Pre-Formed Nucleoside

The key starting material for this process is an appropriately substituted nucleoside with a 3'-OH and 3'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $CH_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 3'-C-branched ribonucleoside is desired. The synthesis of a ribonucleoside is shown in Scheme 6. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 6

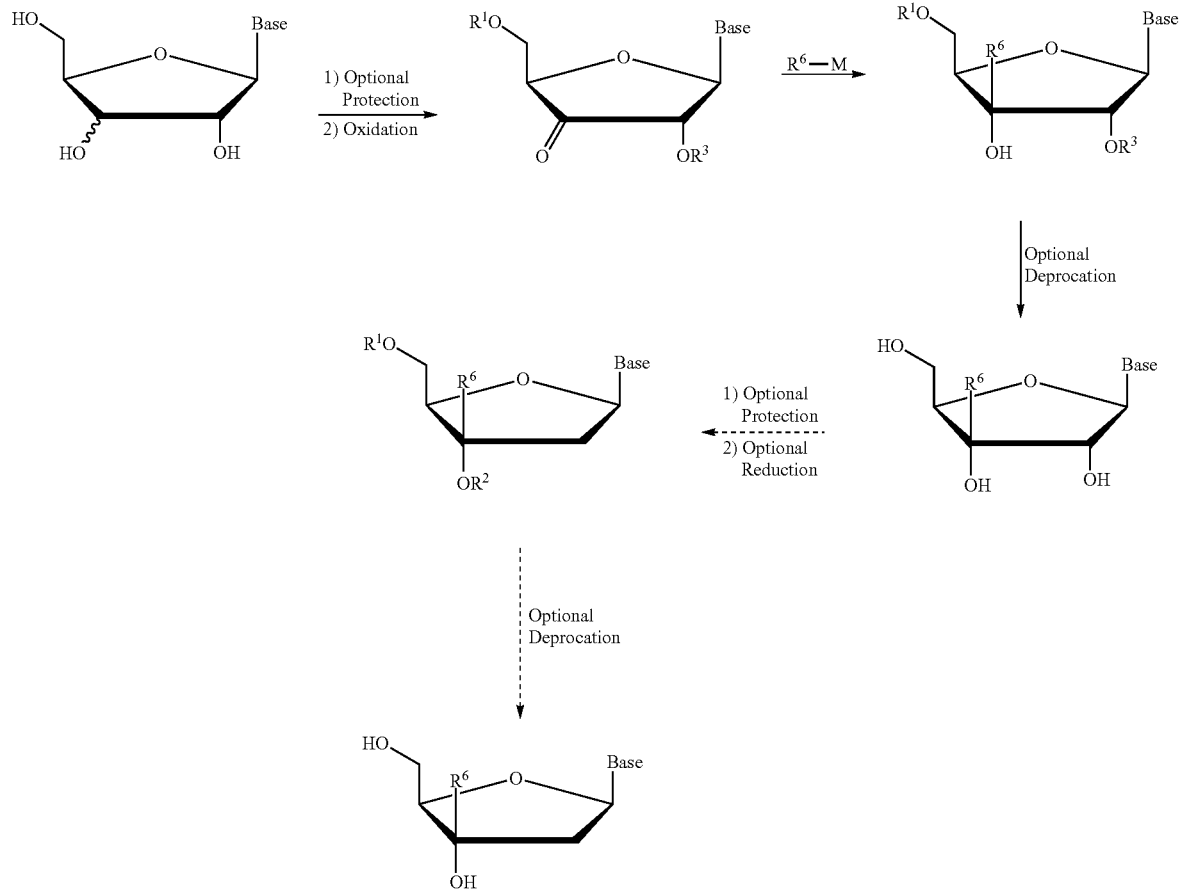

In another embodiment of the invention, the L-enantiomers are desired. Therefore, the L-enantiomers can be corresponding to the compounds of the invention can be prepared following the same foregoing general methods, beginning with the corresponding L-sugar or nucleoside L-enantiomer as starting material.

D. General Synthesis of 4'-C-Branched Nucleosides

4'-C-Branched ribonucleosides of the following structure:

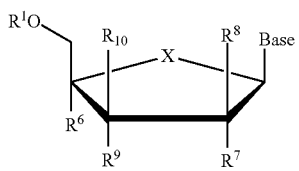

wherein Base, $R^1$, $R^2$, $R^3$, $R^4$, $R^5$, $R^6$, $R^7$, $R^8$, $R^9$, $R^{10}$, Y, $W^1$, $W^2$, $W^3$, X, $X^1$, $X^2$ and $X^3$ are as defined herein can be prepared by one of the following general methods.

1. Modification from the Pentodialdo-Furanose

The key starting material for this process is an appropriately substituted pentodialdo-furanose. The pentodialdo-furanose can be purchased or can be prepared by any known means including standard epimerization, substitution and cyclization techniques.

In a preferred embodiment, the pentodialdo-furanose is prepared from the appropriately substituted hexose. The hexose can be purchased or can be prepared by any known means including standard epimerization (e.g. via alkaline treatment), substitution and coupling techniques. The hexose can be either in the furanose form, or cyclized via any means known in the art, such as methodology taught by Townsend *Chemistry of Nucleosides and Nucleotides*, Plenum Press, 1994, preferably by selectively protecting the hexose, to give the appropriate hexafuranose.

The 4'-hydroxymethylene of the hexafuranose then can be oxidized with the appropriate oxidizing agent in a compatible solvent at a suitable temperature to yield the 4% aldo-modified sugar. Possible oxidizing agents are Swern reagents, Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $CH_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide, though preferably using $H_3PO_4$, DMSO and DCC in a mixture of benzene/pyridine at room temperature.

Then, the pentodialdo-furanose can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991. In the presence of a base, such as sodium hydroxide, the protected pentodialdo-furanose can then be coupled with a suitable electrophilic alkyl, halogeno-alkyl (i.e. $CF_3$), alkenyl or alkynyl (i.e. allyl), to obtain the 4'-alkylated sugar. Alternatively, the protected pentodialdo-furanose can be coupled with the corresponding carbonyl, such as formaldehyde, in the presence of a base, such as sodium hydroxide, with the appropriate polar solvent, such as dioxane, at a suitable temperature, which can then be reduced with an appropriate reducing agent to give the 4'-alkylated sugar. In one embodiment, the reduction is carried out using PhOC(S)Cl, DMAP, preferably in acetonitrile at room temperature, followed by treatment of ACCN and TN/BS refluxed in toluene.

The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 4'-C-branched ribonucleoside is desired. Alternatively, deoxyribonucleoside is desired. To obtain these deoxyribo-nucleosides, a formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

In another embodiment of the invention, the L-enantiomers are desired. Therefore, the L-enantiomers can be corresponding to the compounds of the invention can be prepared following the same foregoing general methods, beginning with the corresponding L-pentodialdo-furanose as starting material.

E. General Synthesis of 2' and/or 3'-Prodrugs

The key starting material for this process is an appropriately substituted 1', 2', 3' or 4'-branched β-D or β-L nucleosides. The branched nucleoside can be purchased or can be prepared by any known means including the techniques disclosed herein. The branched nucleoside can be optionally protected with a suitable protecting group, preferably with a silyl group, by methods well known to those skilled in the art, as taught by Greene et al. *Protective Groups in Organic Synthesis*, John Wiley and Sons, Second Edition, 1991. The protected branched nucleoside can then be coupled with a suitable acyl donor, such as an acyl chloride and/or an acyl anhydride with the appropriate protic or aprotic solvent at a suitable temperature, to give the 2' and/or 3' prodrug of 1', 2', 3' or 4'-branched β-D or β-L nucleoside. Alternatively, the protected branched nucleoside can then be coupled with a suitable acyl, such as a carboxylic acid, such as alkanoic acid and/or amino acid residue, optionally with a suitable coupling agent, with the appropriate aprotic solvent at a suitable temperature, to give the 2' and/or 3' prodrug of 1', 2', 3' or 4'-branched β-D or β-L nucleoside. Possible coupling reagents are any reagents that promote coupling, including but are not limiting to, Mitsunobu reagents (e.g. diisopropyl azodicarboxylate and diethyl azodicarboxylate) with triphenylphosphine or various carbodiimides.

Figure 2:
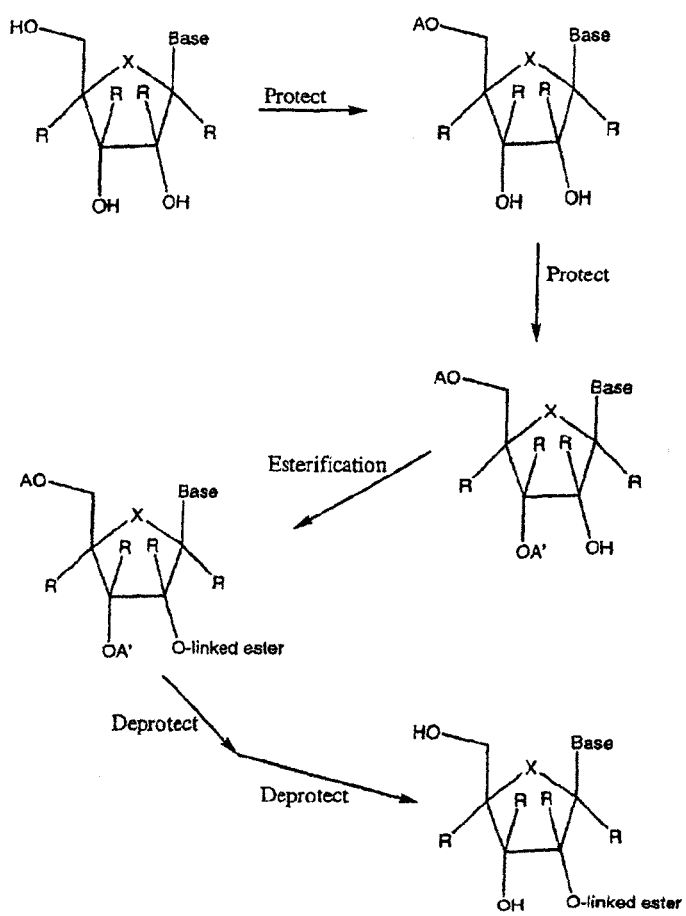
FIG. 2 provides a non-limiting example of the steps involved in esterification of the 1', 2', 3' or 4'-branched β-D or β-L nucleoside to obtain a 2'-prodrug. The same general procedure can be used to obtain the 3'-prodrug by selectively protecting the 2' and 5'-hydroxyl groups or protecting the 2',3' and 5'-hydroxyl groups and selectively deprotecting the 3'-hydroxyl.
Figure 3:
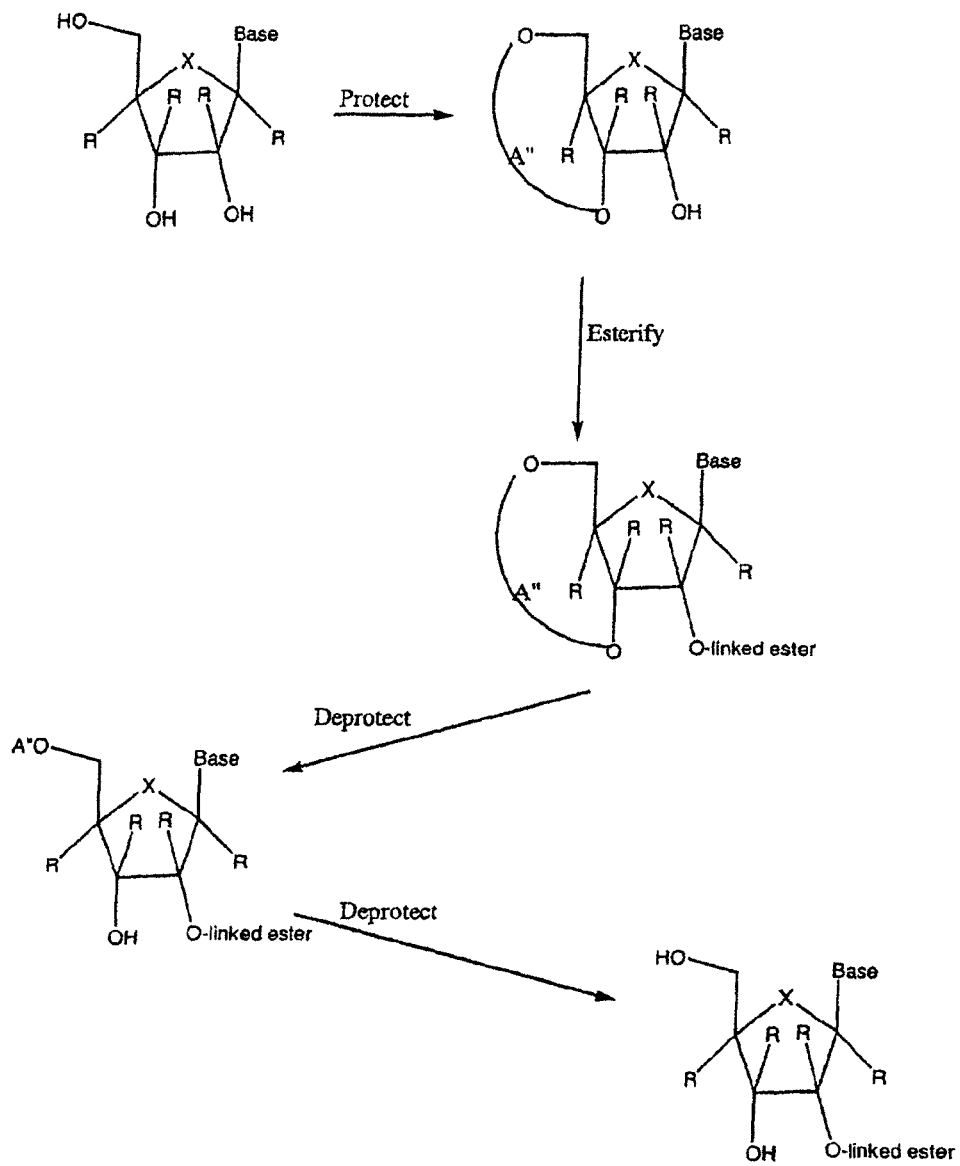
FIG. 3 provides a non-limiting example of the steps involved in esterification of the 1', 2', 3' or 4'-branched β-D or β-L nucleoside to obtain a 3'-prodrug.
Figure 4:
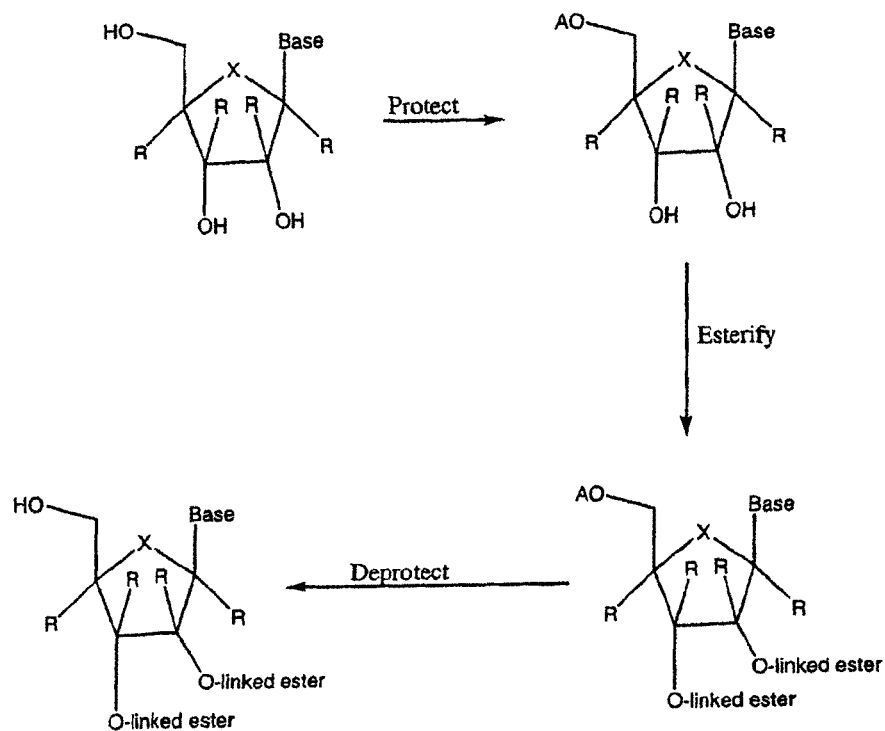
FIG. 4 provides a non-limiting example of the steps involved in esterification of the 1', 2', 3' or 4'-branched β-D or β-L nucleoside to obtain a 2',3'-prodrug.

For example, simple amino-alcohols can be esterified using acid chlorides in refluxing acetonitrile-benzene mixture (See Scheme 7 below: *Synthetic Communications*, 1978, 8(5), 327-333; hereby incorporated by reference). Alternatively, esterification can be achieved using an anhydride, as described in *J. Am. Chem. Soc.*, 1999, 121(24), 5661-5664, which is hereby incorporated by reference. See FIGS. 2, 3 and 4.

Scheme 7

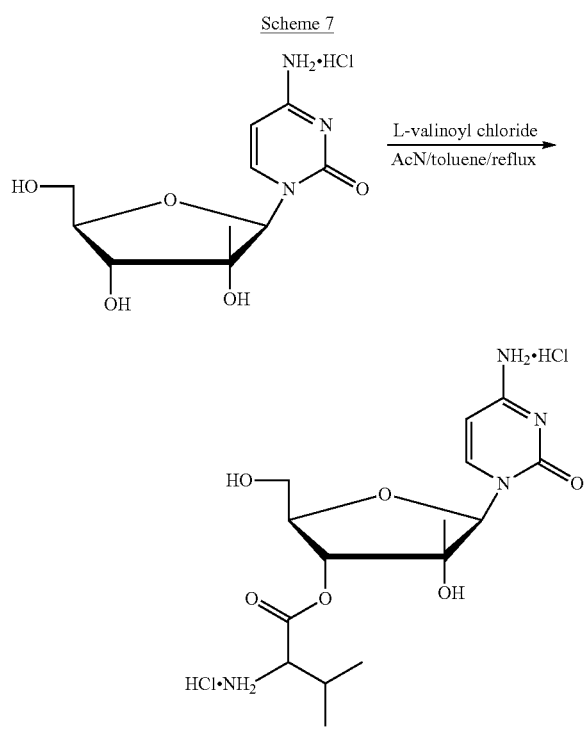

ACN: acetonitrile

The present invention is described by way of illustration, in the following examples. It will be understood by one of ordinary skill in the art that these examples are in no way limiting and that variations of detail can be made without departing from the spirit and scope of the present invention.

Example 1

Preparation of 1'-C-Methylriboadenine Via 6-Amino-9-(1-Deoxy-β-D-Psicofuranosyl)Purine Melting points were determined on a MeI-temp 11 apparatus and are uncorrected. NMR spectra were recorded on a Bruker 400 AMX spectrometer at 400 MHz for $^1$H NMR and 100 MHz for $^{13}$C NMR with TMS as internal standard. Chemical shifts (δ) are reported in parts per million (ppm), and signals are reported as s (singlet), d (doublet), t (triplet), q (quartet), m (multiplet), or bs (broad singlet). IR spectra were measured on a Nicolet 510P FT-IR spectrometer. Mass spectra were recorded on a Micromass Autospec high-resolution mass spectrometer. TLC were performed on Uniplates (silica gel) purchased from Analtech Co. Column chromatography was performed using either silica gel-60 (220-440 mesh) for flash chromatography or silica gel G (TLC grade, >440 mesh) for vacuum flash column chromatography. UV spectra were obtained on a Beckman DU 650 spectrophotometer. Elemental analysis was performed by Atlantic Microlab, Inc., Norcross, Ga., or Galbraith Laboratories, Inc., Knoxyille, Tenn. HPLC was performed with a Waters HPLC system (Millipore Corporation, Milford, Mass.) equipped with a Model 600 controller, a Model 996 photodiode array detector and a Model 717 plus autosampler. Millennium 2010 software was used for system control, data acquisition and processing. A chiralyser polarimetric detector, Perkin-Elmer Model 241MC polarimeter (Wilton, Conn.), was used for the determination of optical rotations.

Synthesis of 1'-C-methylribo-8-methyladenine

The title compound could also be prepared according to a published procedure (J. Farkas, and F. Sorm, "Nucleic acid components and their analogues. XCIV. Synthesis of 6-amino-9-(1-deoxy-β-D-psicofuranosyl)purine" *Collect. Czech. Chem. Commun.* 1967, 32, 2663-2667; J. Farkas", *Collect. Czech. Chem. Commun.* 1966, 31, 1535) (Scheme 8).

Scheme 8

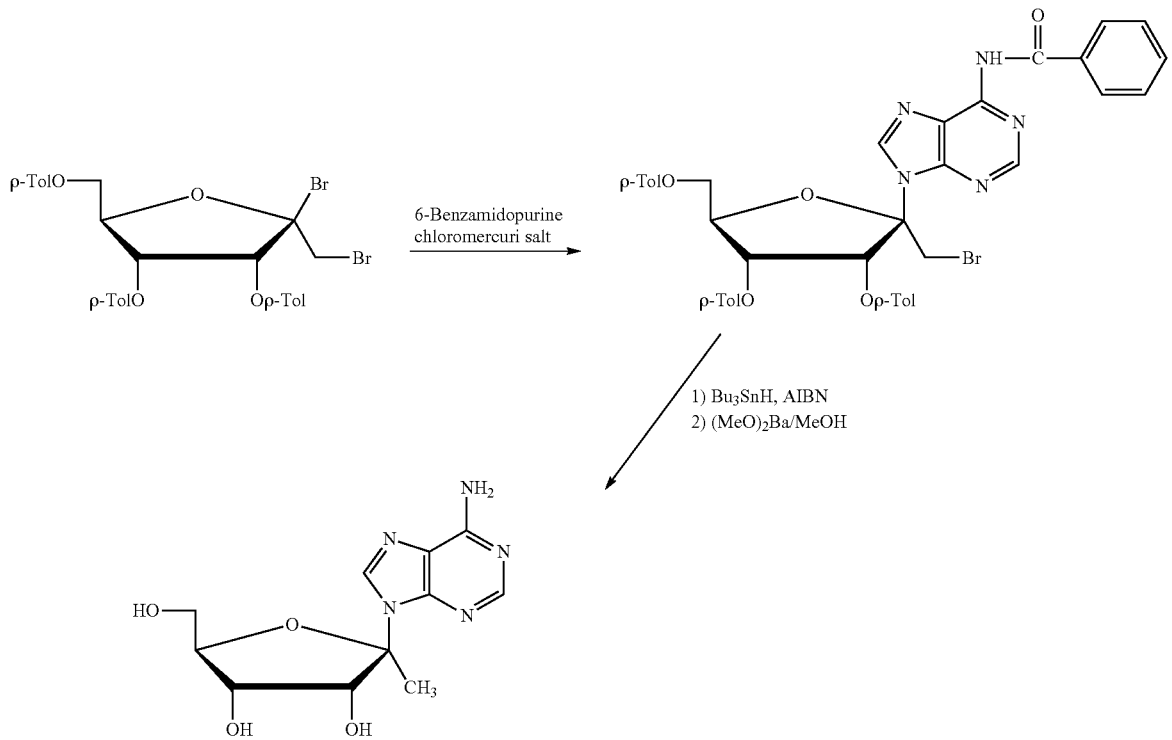

In a similar manner, but using the appropriate sugar and purine bases, the following nucleosides of Formula XXIV are prepared.

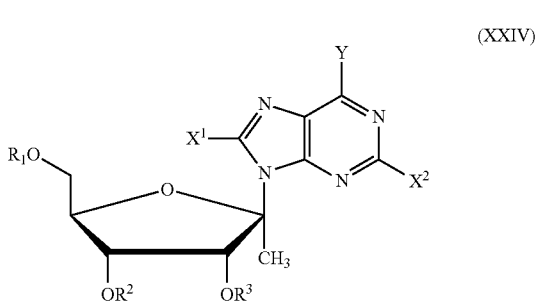

(XXIV)

wherein $R^1$, $R^2$, $R^3$, $X^1$, $X^2$, and Y are defined in Table 1.

Alternatively, the following nucleosides of Formula XXV are prepared, using the appropriate sugar and pyrimidine bases.

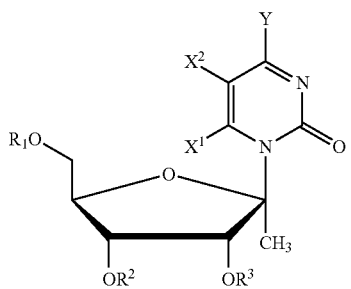

(XXV)

wherein $R^1$, $R^2$, $R^3$, $X^1$, $X^2$, and Y are defined in Table 2.

Alternatively, the following nucleosides of Formula XXVI are prepared, using the appropriate sugar and pyrimidine or purine bases.

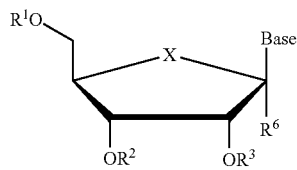

(XXVI)

wherein $R^1$, $R^2$, $R^3$, $R^6$, X, and Base are defined in Table 3.

Alternatively, the following nucleosides of Formula XXVII are prepared, using the appropriate sugar and pyrimidine or purine bases.

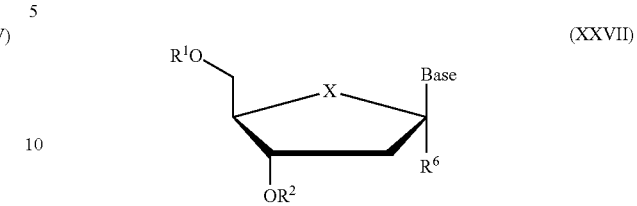

(XXVII)

wherein $R^1$, $R^2$, $R^6$, X, and Base are defined in Table 4.

Alternatively, the following nucleosides of Formula XXVIII are prepared, using the appropriate sugar and pyrimidine or purine bases.

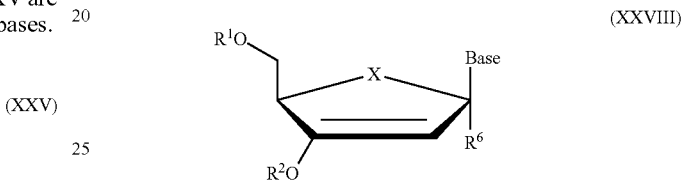

(XXVIII)

wherein $R^1$, $R^2$, $R^6$, X, and Base are defined in Table 5.

Alternatively, the following nucleosides of Formula XXIX are prepared, using the appropriate sugar and pyrimidine or purine bases.

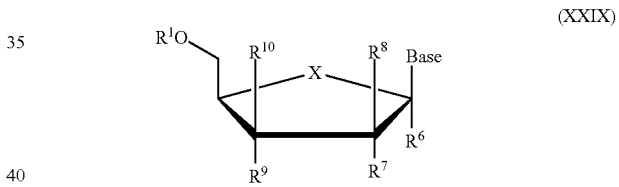

(XXIX)

wherein $R^1$, $R^6$, $R^7$, $R^8$, X, $R^9$, $R^{10}$, and Base are defined in Table 6.

Example 2

Preparation of 2'-C-Methylribo-8-Methyladenine

The title compound was prepared according to a published procedure (R. E. Harry-O'kuru, J. M. Smith, and M. S. Wolfe, "A short, flexible route toward 2'-C-branched ribonucleosides", *J. Org. Chem.* 1997, 62, 1754-1759) (Scheme 9).

Scheme 9

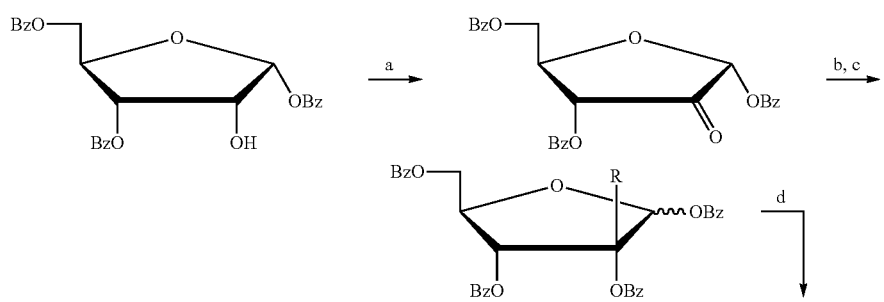

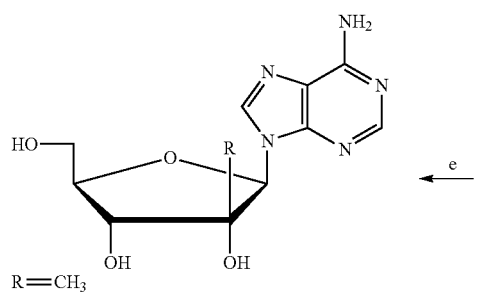
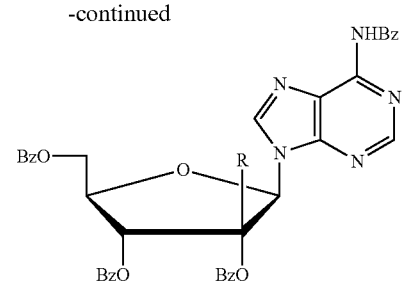

R=CH₃
(a) Dess-Martin periodinane;
(b) MeMgBr/TiCl₄;
(c) BzCl, DMAP, Et₃N;
(d) bis(trimethylsilyl)acetamide, N⁶-benzoyl adenine, TMSOTf;
(e) NH₃/MeOH (a) Dess-Martin periodinane; (b) MeMgBr I TiCl₄; (c) BzCl, DMAP, Et₃N; (d) bis(trimethylsilyl)acetamide, N⁶-benzoyl adenine, TMSOTf; (e) NH₃/MeOH The 3'-prodrug of the 2'-branched nucleoside was prepared according to published procedure (*Synthetic Communications,* 1978, 8(5), 327-333; *J. Am. Chem. Soc.,* 1999, 121(24), 5661-5664). Alternatively, the 2'-branched nucleoside can be esterified without protection (Scheme 9b). Carbonyldiimidazole (377 mg, 2.33 mmol) was added to a solution of N-(tert-butoxycarbonyl)-L-valine (507 mg, 2.33 mmol) in 15 mL of anhydrous tetrahydrofuran. The mixture was stirred at 20° C. for one hour and at 50° C. for 10 minutes and then added to a solution of 4-Amino-1-(3,4-dihydroxy-5-hydroxymethyl-3-methyl-tetrahydro-furan-2-yl)-1H-pyrimidine-2-one (500 mg, 1.95 mmol), 4-(dimethylamino)pyridine (25 mg, 0.195 mmol), triethylamine (5 mL) in anhydrous N,N-dimethylformamide (10 mL), which is also stirring at 50° C. The reaction mixture was stirred at 50° C. for one hour and then examined by HPLC. HPLC analysis indicated the formation of 52% of the desired ester, 17% of starting material in addition to undesired by-products. The 3'-OH of 4-amino-1-(3,4-dihydroxy-5-hydroxymethyl-3-methyl-tetrahydro-furan-2-yl)-1H-pyrimidine-2-one tends to react selectively when coupled with BOC-Val.

In a similar manner, but using the appropriate sugar and purine bases, the following nucleosides of Formula XXX are prepared.

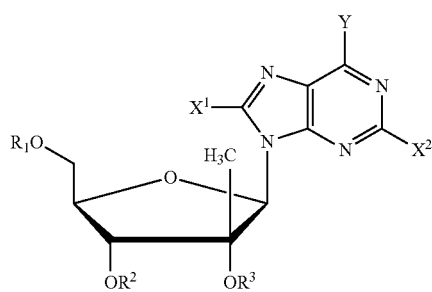

(XXX)

wherein $R^1$, $R^2$, $R^3$, $X^1$, $X^2$, and Y are defined in Table 7.

Alternatively, the following nucleosides of Formula XXXI are prepared, using the appropriate sugar and pyrimidine bases.

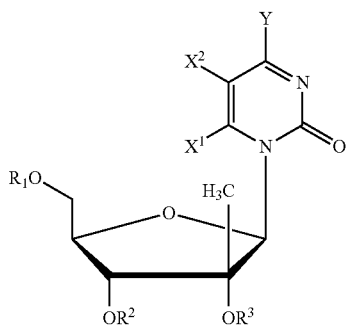

(XXXI)

wherein $R^1$, $R^2$, $R^3$, $X^1$, $X^2$, and Y are defined in Table 8.

Alternatively, the following nucleosides of Formula XXXII are prepared, using the appropriate sugar and pyrimidine or purine bases.

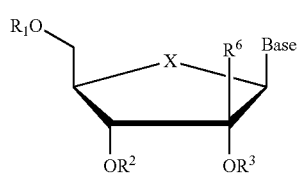

(XXXII)

wherein $R^1$, $R^2$, $R^3$, $R^6$, X, and Base are defined in Table 9.

Alternatively, the following nucleosides of Formula XXXIII are prepared, using the appropriate sugar and pyrimidine or purine bases.

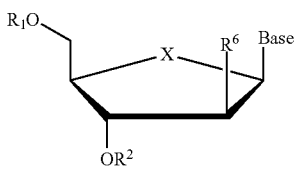

wherein $R^1$, $R^2$, $R^6$, X, and Base are defined in Table 10.

Alternatively, the following nucleosides of Formula XXXIV are prepared, using the appropriate sugar and pyrimidine or purine bases.

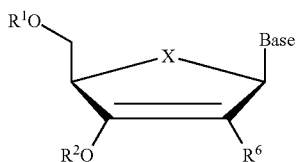

(XXXIV)

wherein R¹, R², R⁶, X, and Base are defined in Table 11. Alternatively, the following nucleosides of Formula XXXV are prepared, using the appropriate sugar and pyrimidine or purine bases.

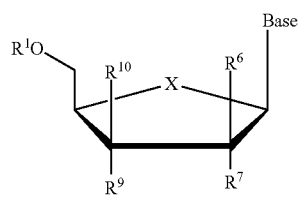

(XXXV)

wherein R¹, R⁶, R⁷, R⁹, R¹⁰, X, and Base are defined in Table 12.

Example 3

Preparation of 3'-C-Methylribo-8-Methyladenine

The title compound can be prepared according to a published procedure (R. F. Nutt, M. J. Dickinson, F. W. Holly, and E. Walton, "Branched-chain sugar nucleosides. III. 3'-C-methyladenine", *J. Org. Chem.* 1968, 33, 1789-1795) (Scheme 10).

In a similar manner, but using the appropriate sugar and purine bases, the following nucleosides of Formula XXXVI are prepared.

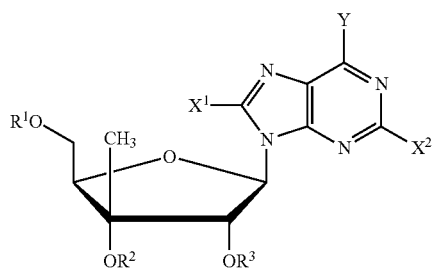

(XXXVI)

wherein R¹, R², R³, X¹, X², and Y are defined in Table 13. Alternatively, the following nucleosides of Formula XXXVII are prepared, using the appropriate sugar and pyrimidine bases.

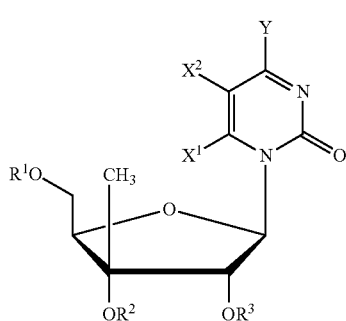

(XXXVII)

wherein R¹, R², R³, X¹, X², and Y are defined in Table 14.

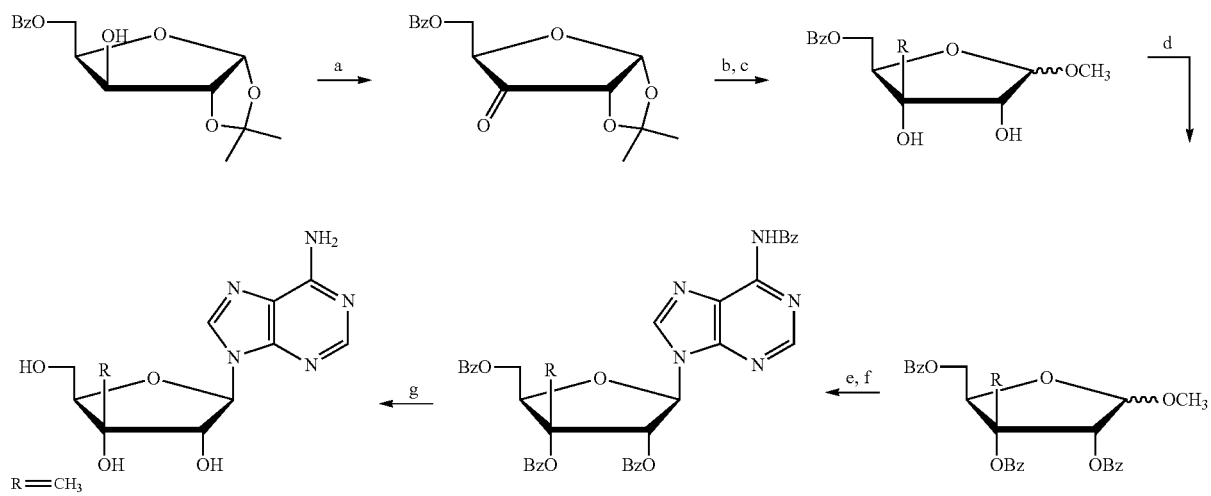

Scheme 10

R = CH₃
(a) RuO₂/NaIO₄;
(b) MeMgI/TiCl₄;
(c) HCl/MeOH/H₂O;
(d) BzCl/pyridine;
(e) AcBr, HBr/AcOH;
(f) chloromercuri-6-benzamidopurine;
(g) NH₃/MeOH.

Alternatively, the following nucleosides of Formula XXX-VIII are prepared, using the appropriate sugar and pyrimidine or purine bases.

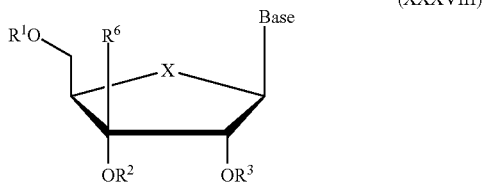

(XXXVIII)

wherein $R^1$, $R^2$, $R^3$, $R^6$, X, and Base are defined in Table 15. Alternatively, the following nucleosides of Formula XXXIX are prepared, using the appropriate sugar and pyrimidine or purine bases.

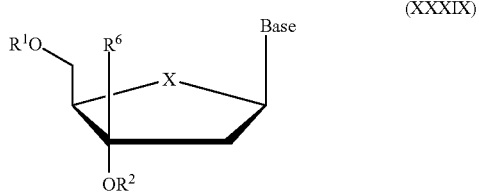

(XXXIX)

wherein $R^1$, $R^2$, $R^6$, X, and Base are defined in Table 16. Alternatively, the following nucleosides of Formula XXXX are prepared, using the appropriate sugar and pyrimidine or purine bases.

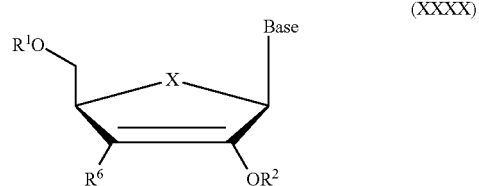

(XXXX)

wherein $R^1$, $R^2$, $R^6$, X, and Base are defined in Table 17. Alternatively, the following nucleosides of Formula XXXXI are prepared, using the appropriate sugar and pyrimidine or purine bases.

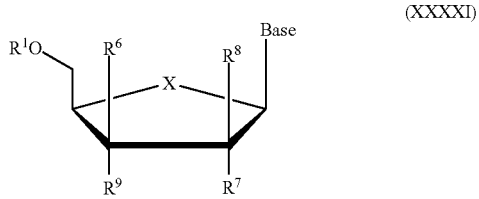

(XXXXI)

wherein $R^1$, $R^6$, $R^7$, $R^8$, $R^9$, X, and Base are defined in Table 18.

Example 4

Preparation of 1-O-Methyl-2,3-O-Isopropylidene-β-D-Ribofuranose-(1)

The title compound can be prepared according to a published procedure (Leonard, N.J.; Carraway, K. L. "5-Amino-5-deoxyribose derivatives. Synthesis and use in the preparation of "reversed" nucleosides" *J. Heterocycl. Chem.* 1966, 3, 485-489).

A solution of 50.0 g (0.34 mole) of dry D-ribose in 1.0 L of acetone, 100 mL of 2,2-dimethoxypropane, 200 mL of methanol containing 20 mL of methanol saturated with hydrogen chloride at 0° C. was stirred overnight at room temperature. The resulting solution was neutralized with pyridine and evaporated under reduced pressure. The resulting oil was partitioned between 400 mL of water and 400 mL of methylene chloride. The water layer was extracted twice with methylene chloride (400 mL). The combined organic extracts were dried over sodium sulfate and evaporated under reduced pressure. The residue was purified by silica gel column chromatography [eluent: stepwise gradient of methanol (1-2%) in methylene chloride] to give pure 1 (52.1 g, 75%) as a yellow syrup. $^1$H-NMR (CDCl$_3$): δ 5.00 (s, 1H, H-1), 4.86 (d, 1H, H-2, $J_{2-3}$=5.9 Hz), 4.61 (d, 1H, H-3, $J_{3-2}$=5.9 Hz), 4.46 (t, H-1, H-4, $J_{4-5}$=2.7 Hz), 3.77-3.61 (m, 2H, H-5 and H-5'), 3.46 (s, 1H, OCH$_3$), 3.0-2.4 (br s, 1H, OH-5), 1.51 (s, 3H CH$_3$), 1.34 (s, 3H CH$_3$); MS (matrix GT): FAB>0 m/z 173 (M-OCH$_3$)$^+$.

Example 5

Preparation of 1-O-Methyl-2,3-O-Isopropylidene-β-D-Pentodialdo-Ribofuranose-(2)

The title compound can be prepared according to a published procedure (Jones, G. H.; Moffatt, J. G. Oxidation of carbohydrates by the sulfoxide-carbodiimide and related methods. Oxidation with dicyclohexylcarbodiimide-DMSO, diisopropylcarbodiimide-DMSO, acetic anhydride-DMSO, and phosphorus pentoxide-DMSO: in *Methods in Carbohydrate Chemistry*; Whisler, R. L. and Moffatt, J. L. Eds; Academic Press: New York, 1972; 315-322).

Compound 1 was co-evaporated twice with anhydrous pyridine. Dicyclohexylcarbodi-imide (DCC, 137.8 g, 0.67 mol) was added to a solution of 1 (68.2 g, 0.33 mole) in anhydrous benzene (670 mL), DMSO (500 mL) and pyridine (13.4 mL). To the resulting solution, cooled to 0° C., was added a solution of anhydrous crystalline orthophosphoric acid (16.4 g, 0.167 mmol) in anhydrous DMSO (30 mL). The mixture was stirred for 1.5 hours at 0° C. and 18 hours at room temperature under argon atmosphere, diluted with ethyl acetate (1000 mL). A solution of oxalic acid dihydrate (63.1 g, 038 mol) in DMSO (30 mL) was added and the reaction mixture was stirred at room temperature during 1 hour and then filtered to eliminate precipitated dicyclohexylurea (DCU). The filtrate was concentrated to a volume of about 600 mL under reduced pressure and neutralized with a saturated aqueous sodium hydrogen carbonate solution (400 mL). Brine (200 mL) was added and the organic layer was extracted with ethyl acetate (4×1000 mL). The combined organic layers were concentrated to a volume of about 2000 mL, washed with a saturated aqueous sodium hydrogen carbonate solution (2×700 mL), and with brine (2×700 mL) before being dried over sodium sulfate and evaporated under reduced pressure. A small fraction of the crude residue was purified on silica gel chromatography [eluent: chloroform/ethyl ether, 8:2] in order to confirm the structure of 2 which was obtained as a pale yellow solid. $^1$H-NMR (CDCl$_3$): δ 9.61 (s, 1H, H-5), 5.12 (s, 1H, H-1), 5.08 (d, 1H, H-2, $J_{2-3}$=5.9 Hz), 4.53 (d, 1H, H-3, J3.2=6.0 Hz), 4.51 (s, 1H, H-4), 3.48 (s, 1H, OCH$_3$), 1.56 (s, 3H CH$_3$), 1.36 (s, 3H CH$_3$); MS (matrix GT): FAB>0 m/z 203 (M+H)$^+$, 171 (M-OCH$_3$)$^+$.

Example 6

Preparation of 4-C-Hydroxymethyl-1-O-Methyl-2,3-O-Isopropylidene-β-D-Ribofuranose-(3)

The title compound can be prepared according to a published procedure (Leland, D. L.; Kotick, M. P. "Studies on 4-C-(hydroxymethyl)pentofuranoses. Synthesis of 9-[4-C-(hydroxymethyl)-α-L-threo-pentofuranosyl]adenine" *Carbohydr. Res.* 1974, 38, C9-C11; Jones, G. II.; Taniguchi, M.; Tegg, D.; Moffatt, J. G. "4'-substituted nucleosides. 5. Hydroxylation of nucleoside 5'-aldehydes" *J. Org. Chem.* 1979, 44, 1309-1317; Gunic, E.; Girardet, J.-L.; Pietrzkowski, Z.; Ester, C.; Wang, G. "Synthesis and cytotoxicity of 4'-C- and 5'-C-substituted Toyocamycins" *Bioorg. Med. Chem.* 2001, 9, 163-170).

To a solution of the crude material (2) obtained above and 37% aqueous formaldehyde (167 mL) in dioxane (830 mL) was added aqueous sodium hydroxide (2N, 300 mL). The mixture was stirred at room temperature for 4 hours and neutralized by addition of Dowex 50 W×2 (H$^+$ form). The resin was filtered, washed with methanol, and the combined filtrates were concentrated to dryness and coevaporated several times with absolute ethanol. Sodium formate which was precipitated from absolute ethanol was removed by filtration, the filtrate was concentrated to dryness and the residue was purified by silica gel column chromatography [eluent: stepwise gradient of methanol (0-4%) in chloroform] to give pure 3 (42.2 g, 54% from 1), which was recrystallized from cyclohexane. Mp=94-95 (dec.) (lit. 94-96.5; 97-98: Refs: 3,4), $^1$H-NMR (DMSO-d$_6$): 4.65 (s, 1H, H-1), 4.44-4.37 (m, 3H, H-2, H-3 and OH-6), 4.27 (t, 1H, OH-5, J=5.6 Hz, J=6.0 Hz), 3.42-3.34 (m, 2H, H-5 and H-6) 3.29 (dd, 1H, H-5', J$_{5'-OH}$=5.4 Hz, J5-5'=11.4 Hz), 3.11 (dd, 1H, H-6', J$_{6'-OH}$=5.7 Hz, J6-6'=10.9 Hz), 3.03 (s, 31-1, OCH$_3$), 1.48 (s, 3H CH$_3$), 1.05 (s, 3H CH$_3$); MS (matrix GT): FAB>0 m/z 469 (2M+H)$^+$, 235 (M+H)$^+$, 203 (M-OCH$_3$)+ FAB<0 m/z 233 (M-H)$^-$.

Example 7

Preparation of 6-O-Monomethoxytrityl-4-C-Hydroxymethyl-1-O-Methyl-2,3-O-Isopropylidene-β-D-Ribofuranose-(4)

The title compound can be prepared according to a published procedure (Gunk, E.; Girardet, J.-L.; Pietrzkowski, Z.; Esler, C.; Wang, G. "Synthesis and cytotoxicity of 4'-C- and 5'-C-substituted Toyocamycins" *Bioorg. Med. Chem.* 2001, 9, 163-170).

To a solution of 3 (41.0 g, 175 mmol) in pyridine (700 ml) was added by portions dimethoxytrityl chloride (60.5 g, 178 mmol) at +4° C. The reaction mixture was stirred for 3 hours at room temperature. After addition of methanol, the reaction mixture was concentrated (200 ml) and then dissolved with ethyl acetate (2 L). The organic layer was washed with a 5% aqueous sodium hydrogen carbonate solution, with water and dried over sodium sulfate and then evaporated to dryness. Purification by silica gel column chromatography [eluent: ethyl acetate/hexane 15/85] afforded pure 4 (63.0 g, 68%) as a syrup. $^1$H-NMR (CDCl$_3$): δ 7.5-6.9 (m, 13H, MMTr), 4.89 (s, 1H, H-1), 4.72-4.62 (m, 3H, H-2, H-3 and OH-5), 3.82 (dd, 1H, H-5, J$_{5-OH}$=5.5 Hz, J5-5'=10.5 Hz), 3.79 (s, 6H, OCH3), 3.54 (dd, 1H, H-5', J$_{5'-OH}$=4.9 Hz, J$_{5'-5}$=10.5 Hz), 3.31 (s, 3H, OCH$_3$), 3.24 (d, 1H, H-6, J$_{6-6'}$=9.2 Hz), 3.13 (d, 1H, H-6', J$_{6'-6}$=9.2 Hz), 1.24 (s, 3H CH$_3$), 1.15 (s, 3H CH$_3$); MS (matrix GT): FAB>0 m/z 303 (DMTr)$^+$.

Example 8

Preparation of 5-O-Benzoyl-4-C-Hydroxymethyl-1-O-Methyl-2,3-O-Isopropylidene-β-D-Ribo-Furanose-(5)

The title compound can be prepared according to a published procedure (Gunk, E.; Girardet, J.-L.; Pietrzkowski, Z.; Esler, C.; Wang, G. "Synthesis and cytotoxicity of 4'-C- and 5'-C-substituted Toyocamycins" *Bioorg. Med. Chem.* 2001, 9, 163-170).

To a solution of 4 (2.51 g, 4.68 mmol) in anhydrous pyridine (37 mL) was added under argon benzoyl chloride (1.09 mL, 9.36 mmol) and the reaction mixture was stirred for 13 hours at to room temperature. Then the reaction was cooled to 0° C. and stopped with ice-cold water (100 mL). The water layer was extracted with methylene chloride (3□ 200 mL). The combined organic layers were washed with a saturated aqueous sodium hydrogen carbonate solution (2×150 mL), with water (1×150 mL) and then dried over sodium sulfate and evaporated under reduced pressure. The residue was dissolved in 80% acetic acid (70.2 mL) and the mixture was stirred at room temperature for 3 hr and concentrated to dryness. Purification by silica gel column chromatography [eluent: chloroform] afforded pure 5 (1.40 g, 88%) as a syrup. $^1$H-NMR (CDCl$_3$): δ 8.1-7.4 (m, 5H, C$_6$H$_5$CO), 5.08 (s, 1H, H-1), 4.77 (dd, 2H, H-2 and H-3, J=6.1 Hz, J=8.2 Hz), 4.51 (q, 2H, H-5 and H-5', J=11.5 Hz, J$_{5-5'}$=23.8 Hz), 3.91 (t, 2H, H-6 and H-6', J=12.3 Hz), 4.38 (s, 1H, OCH$_3$), 2.2-1.8 (brs, 1H, OH-6), 1.57 (s, 3H CH$_3$), 1.38 (s, 31-1 CH$_3$); MS (matrix GT): FAB>0 m/z 677 (2M+H)$^+$, 339 (M+H)$^+$, 307 (M-OCH$_3$)$^+$, 105 (C$_6$H$_5$CO)$^+$ FAB<0 m/z 121 (C$_6$H$_5$CO$_2$)$^-$.

Example 9

Preparation of 5-O-Benzoyl-4-C-Methyl-1-O-Methyl-2,3-O-Isopropylidene-β-D-Ribofuranose-(6)

The title compound can be prepared according to a published procedure (Gunic, F.; Girardet, J.-L.; Pietrzkowski, Z.; Esler, C.; Wang, G. "Synthesis and cytotoxicity of 4'-C- and 5'-C-substituted Toyocamycins" *Bioorg. Med. Chem.* 2001, 9, 163-170).

A solution of 5 (37.6 g, 0.111 mol), 4-dimethylaminopyridine (DMAP, 40.7 g, 0.333 mol) and phenoxythiocarbonyle chloride in anhydrous acetonitrile (1000 mL) was stirred at room temperature for 1 hour and concentrated to dryness. The residue was dissolved in methylene chloride (500 mL) and successively washed with 0.2 M hydrochloric acid (2×500 mL) and water (500 mL) before being dried over sodium sulfate, evaporated under reduced pressure and coevaporated several times with anhydrous toluene. The crude material was dissolved in anhydrous toluene (880 mL) and tris(trimethylsilyl)silane (TMSS, 42.9 mL, 0.139 mol), and 1,1'-azobis (cyclohexanecarbonitrile) (ACCN, 6.8 g, 27.8 mmol) were added. The reaction mixture was stirred under reflux for 45 minutes, cooled to room temperature and concentrated under reduced pressure. The resulting residue was purified by silica gel column chromatography [eluent: stepwise gradient of diethyl ether (5-20%) in petroleum ether] to give pure 6 (26.4 g, 74%) as a pale yellow syrup. $^1$H-NMR (DMSO-d$_6$): δ 8.0-7.5 (m, 5H, C$_6$H$_5$CO), 4.85 (s, 1H, H-1), 4.63 (dd, 2H, H-2 and H-3, J=6.1 Hz, J=11.6 Hz), 4.24 (d, 1H, H-5, J$_{5-5'}$=11.1 Hz), 4.10 (d, 1H, H-5', J$_{5'-5}$=11.1 Hz), 3.17 (s, 1H, OCH$_3$), 1.38 (s, 3H CH$_3$), 1.30 (s, 3H CH$_3$), 1.25 (s, 3H CH$_3$); MS (matrix GT): FAB>0 m/z 291 (M-OCH$_3$)$^+$, 105 (C$_6$H$_5$CO)$^+$ FAB<0 m/z 121 (C$_6$H$_5$CO$_2$)$^-$.

Example 10

Preparation of 5-O-Benzoyl-4-C-Methyl-1,2,3-O-Acetyl-α,β-D-Ribofuranose-(7)

Compound 6 (22.5 g, 70 mmol) was suspended in a 80% aqueous acetic acid solution (250 mL). The solution was heated at 100° C. for 3 hours. The volume was then reduced by half and coevaporated with absolute ethanol and pyridine. The oily residue was dissolved in pyridine (280 mL) and then cooled at 0° C. Acetic anhydride (80 mL) and 4-dimethylamino-pyridine (500 mg) were added. The reaction mixture was stirred at room temperature for 3 hours and then concentrated under reduced pressure. The residue was dissolved with ethyl acetate (1 L) and successively washed with a saturated aqueous sodium hydrogen carbonate solution, a 1 M hydrochloric acid and water. The organic layer was dried over sodium sulfate and evaporated under reduced pressure. The resulting residue was purified by silica gel column chromatography [eluent: stepwise gradient of diethyl ether (30-40%) in petroleum ether] to give pure 7 (16.2 g, 60%) as a pale yellow syrup. A small fraction of the material was re-purified on silica gel chromatography [same eluent: system] in order separate the α and the β anomers.

α anomer: $^1$H-NMR (DMSO-d$_6$): δ 8.1-7.5 (m, 5H, C$_6$H$_5$CO), 6.34 (pt, 1H, H-1, J=2.4 Hz, J=2.1 Hz), 5.49 (m, 2H, H-2 and H-3), 4.33 (q, 2H, H-5 and H-5', J=11.6 Hz, J=18.7 Hz), 2.15 (s, 3H, CH$_3$CO$_2$), 2.11 (s, 3H, CH$_3$CO$_2$), 2.07 (s, 3H, CH$_3$CO$_2$), 1.37 (s, 3H, CH$_3$); MS (matrix GT): FAB>0 m/z 335 (M-CH$_3$CO$_2^-$)$^+$, 275 (M-CH$_3$CO$_2^-$+H)$^+$, 105 (C$_6$H$_5$CO)$^+$, 43 (CH$_3$CO)$^+$ FAB<0 m/z 121 (C$_6$H$_5$CO$_2^-$)$^+$, 59 (CH$_3$CO$_2$)$^-$.

β anomer: $^1$H-NMR (DMSO-d$_6$): δ 8.1-7.5 (m, 5H, C$_6$H$_5$CO), 5.99 (s, 1H, H-1), 5.46 (d, 1H, H-2, J$_{2-3}$=5.3 HZ), 5.30 (d, 1H, H-2, J$_{2-3}$=5.3 Hz), 4.39 (d, 1H, H-5, J$_{5-5'}$=11.7 Hz), 4.19 (d, 1H, H-5', J$_{5'-5}$=11.7 Hz), 2.10 (s, 3H, CH$_3$CO$_2$), 2.06 (s, 3H, CH$_3$CO$_2$), 2.02 (s, 3H, CH$_3$CO$_2$), 1.30 (s, 3H, CH$_3$); MS (matrix GT): FAB>0 m/z 335 (M-CH$_3$CO$_2^-$)$^+$, 275 (M-CH$_3$CO$_2^-$+H)$^+$, 105 (C$_6$H$_5$CO)$^+$, 43 (CH$_3$CO)$^+$ FAB<0 m/z 121 (C$_6$H$_5$CO$_2$)$^-$, 59 (CH$_3$CO$_2$)$^-$.

Example 11

Preparation of O-6-Diphenylcarbamoyl-N$^2$-Isobutyryl-9-(2,3-Di-O-Acetyl-5-O-Benzoyl-4-C-Methyl-β-D-Ribofuranosyl)-8-Methylguanine-(18)

To a suspension of O-6-diphenylcarbamoyl-8-methyl-N$^2$-isobutyrylguanine in anhydrous toluene (20 mL) was added N,O-bis(trimethylsilyl)acetamide (1.92 mL, 7.9 mmol). The reaction mixture was allowed to warm under reflux for 1 hour. Compound 7 (1.55 g, 3.93 mmol) was dissolved in toluene (10 mL) and trimethylsilyltrifluoro-methanesulfonate (TMSTf) (915 mL, 4.72 mmol) was added. The mixture was heated under reflux for 30 minutes. The solution was then cooled to room temperature and neutralized with a 5% aqueous sodium hydrogen carbonate solution. The reaction mixture was diluted with ethyl acetate (200 mL). The organic phase was washed with a 5% aqueous sodium hydrogen carbonate solution (150 mL) and with water (2×150 mL). The organic layer was dried over Na$_2$SO$_4$ and evaporated to dryness. The residue was purified by silica gel column chromatography [eluent: stepwise gradient of diethyl ether (70-90%) in petroleum ether] to afford 18.

Example 12

Preparation of 9-(4-C-Methyl-β-D-Ribofuranosyl)-8-Methylguanine-(19)

The title compound can be prepared according to a published procedure from 18 (Waga, T.; Nishizaki, T.; Miyakawa, I.; Orhui, H.; Meguro, H. "Synthesis of 4'-C-methylnucleosides" *Biosci. Biotechnol. Biochem.* 1993, 57, 1433-1438).

A solution of 18 in methanolic ammonia (previously saturated at −10° C.) (20 mL) was stirred at room temperature overnight. The solvent was evaporated under reduced pressure and the residue was partitioned between methylene chloride (60 mL) and water (60 mL). The aqueous layer was washed with methylene chloride (2×60 mL), concentrated under reduced pressure. The residue was purified by an RP18 column chromatography [eluent water/acetonitrile 95/5] to afford 19.

Example 13

9-(2,3-Di-O-Acetyl-5-O-Benzoyl-4-C-Methyl-β-D-Ribofuranosyl)-8-Methyladenine-(20)

A solution of 7 (1.10 g, 2.79 mmol) in anhydrous acetonitrile (50 ml) was treated with 8-methyladenine and stannic chloride (SnCl$_4$, 660 µL, 5.58 mmol) and stirred at room temperature overnight. The solution was concentrated under reduced pressure, diluted with chloroform (100 mL) and treated with a cold saturated aqueous solution of NaHCO$_3$ (100 ml). The mixture was filtered on celite, and the precipitate was washed with hot chloroform. The filtrates were combined, washed with water (100 ml) and brine (100 ml), dried (Na$_2$SO$_4$), and evaporated under reduced pressure. The residue was purified by silica gel column chromatography [eluent: stepwise gradient of methanol β-5%) in dichloromethane] to afford 20.

Example 14

Preparation of 9-(4-C-Methyl-β-D-Ribofuranosyl)-8-Methyladenine-(21)

The title compound can be prepared according to a published procedure from 20 (Waga, T.; Nishizaki, T.; Miyakawa, I.; Orhui, H.; Meguro, H. "Synthesis of 4'-C-methylnucleosides" *Biosci. Biotechnol. Biochem.* 1993, 57, 1433-1438).

A solution of 20 in methanolic ammonia (previously saturated at −10° C.) (50 mL) was stirred at room temperature overnight. The solvent was evaporated under reduced pressure and the residue was partitioned between methylene chloride (100 ml) and water (100 ml). The aqueous layer was washed with methylene chloride (2×100 mL), and concentrated under reduced pressure. The residue was purified by silica gel column chromatography [eluent: stepwise gradient of methanol (10-30%) in ethyl acetate] to afford 21.

In a similar manner, but using the appropriate sugar and purine bases, the following nucleosides of Formula XXXXII are prepared.

(XXXXII)

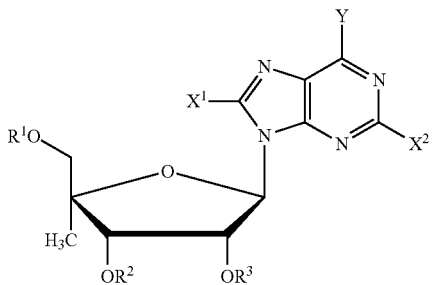

wherein $R^1$, $R^2$, $R^3$, $X^1$, $X^2$, and Y are defined in Table 19.

Example 15

Preparation of 1-(5-O-Benzoyl-4-C-Methyl-2,3-O-Acetyl-β-D-Ribofuranosyl)-6-Methyluracil-(8)

A suspension of 6-methyluracil was treated with hexamethyldisilazane (HMDS, 21 mL) and a catalytic amount of ammonium sulfate during 17 hours under reflux. After cooling to room temperature, the mixture was evaporated under reduced pressure, and the residue, obtained as a colorless oil, was diluted with anhydrous 1,2-dichloroethane (7.5 mL). To the resulting solution was added 7 (0.99 g, 2.51 mmol) in anhydrous 1,2-dichloroethane (14 mL), followed by addition of trimethylsilyl trifluoromethanesulfonate (TMSTf, 0.97 mL, 5.02 mmol). The solution was stirred for 2.5 hours at room temperature under argon atmosphere, then diluted with chloroform (150 mL), washed with the same volume of a saturated aqueous sodium hydrogen carbonate solution and finally with water (2×100 mL). The organic phase was dried over sodium sulfate, then evaporated under reduced pressure. The resulting crude material was purified by silica gel column chromatography [eluent: stepwise gradient of methanol (0-2%) in chloroform] to afford pure 8.

Example 16

Preparation of 1-(4-C-Methyl-β-D-Ribofuranosyl)-6-Methyluracil-(9)

The title compound can be prepared according to a published procedure from 8 (Waga, T.; Nishizaki, T.; Miyakawa, I.; Orhui, H.; Meguro, H. "Synthesis of 4'-C-methylnucleosides" *Biosci. Biotechnol. Biochem.* 1993, 57, 1433-1438).

A solution of 8 in methanolic ammonia (previously saturated at −10° C.) (27 mL) was stirred at room temperature overnight. The solvent was evaporated under reduced pressure and the residue was partitioned between methylene chloride (40 mL) and water (40 mL). The aqueous layer was washed with methylene chloride (2×40 mL), concentrated under reduced pressure and coevaporated several times with absolute ethanol. Recrystallization from a mixture absolute ethanol/methanol gave 9.

Example 17

Preparation of 1-(5-O-Benzoyl-4-C-Methyl-2,3-O-Acetyl-β-D-Ribofuranosyl)-4-Thio-6-Methyl-Uracil-(10)

Lawesson's reagent (926 mg, 2.29 mmol) was added under argon to a solution of 8 in anhydrous 1,2-dichloroethane (65 mL) and the reaction mixture was stirred overnight under reflux. The solvent was evaporated under reduced pressure and the residue was purified by silica gel column chromatography [eluent: stepwise gradient of methanol (1-2%) in chloroform] to give pure 10.

Example 18

Preparation of 1-(4-C-Methyl-β-D-Ribofuranosyl)-4-Thio-6-Methyluracil-(11)

A solution of 10 in methanolic ammonia (previously saturated at −10° C.) (27 mL) was stirred at room temperature overnight. The solvent was evaporated under reduced pressure and the residue was partitioned between methylene chloride (40 ml) and water (40 mL). The aqueous layer was washed with methylene chloride (2×40 mL), concentrated under reduced pressure. The crude material was purified by silica gel column chromatography [eluent: stepwise gradient of methanol (5-7%) in methylene chloride] to give 11, which was lyophilized.

Example 19

Preparation of 1-(4-C-Methyl-β-D-Ribofuranosyl)-6-Methylcytosine, Hydrochloric Form-(12)

Compound II was treated with methanolic ammonia (previously saturated at −10° C.), (12 mL) at 100° C. in a stainless-steel bomb for 3 hours, then cooled to room temperature. The solvent was evaporated under reduced pressure and the residue was partitioned between methylene chloride (40 mL) and water (40 mL). The aqueous layer was washed with methylene chloride (2×40 mL), concentrated under reduced pressure. The crude material was purified by silica gel column chromatography [eluent: methylene chloride/methanol/ammonium hydroxide 65:30:5]. The collected fractions were evaporated under reduced pressure and in absolute ethanol (6.3 mL). To the solution was added a 2N hydrochloric acid solution (1.5 mL) and the mixture was stirred before being concentrated under reduced pressure. The procedure was repeated twice and 12 was precipitated from absolute ethanol.

Example 20

Preparation of 1-(5-O-Benzoyl-4-C-Methyl-2,3-O-Acetyl-β-D-Ribofuranosyl)-6-Methylthymine-(13)

A suspension of 6-methylthymine was treated with hexamethyldisilazane (HMDS, 17 mL) and a catalytic amount of ammonium sulfate overnight under reflux. After cooling to room temperature, the mixture was evaporated under reduced pressure, and the residue, obtained as a colorless oil, was diluted with anhydrous 1,2-dichloroethane (6 mL). To the resulting solution was added 7 (1.0 g, 2.53 mmol) in anhydrous 1,2-dichloroethane (14 mL), followed by addition of trimethylsilyl trifluoromethanesulfonate (TMSTf, 0.98 mL, 5.06 mmol). The solution was stirred for 5 hours at room temperature under argon atmosphere, then diluted with chloroform (150 mL), washed with the same volume of a saturated aqueous sodium hydrogen carbonate solution and finally with water (2×100 mL). The organic phase was dried over sodium sulfate, then evaporated under reduced pressure. The resulting crude material was purified by silica gel column chromatography [eluent: 2% of methanol in chloroform] to afford pure 13.

Example 21

Preparation of 1-(4-C-Methyl-β-D-Ribofuranosyl)-6-Methylthymine-(14)

The title compound can be prepared according to a published procedure from 13 (Waga, T.; Nishizaki, T.; Miyakawa, I.; Orhui, H.; Meguro, H. "Synthesis of 4'-C-methylnucleosides" *Biosci. Biotechnol. Biochem.* 1993, 57, 1433-1438).

A solution of 13 in methanolic ammonia (previously saturated at −10° C.) (60 mL) was stirred at room temperature overnight. The solvent was evaporated under reduced pressure and the residue was partitioned between methylene chloride (60 mL) and water (60 mL). The aqueous layer was washed with methylene chloride (2×60 mL), concentrated under reduced pressure and coevaporated several times with absolute ethanol. Recrystallization from methanol gave 14.

Example 22

Preparation of 1-(5,2,3-Tri-O-Acetyl-4-C-Methyl-β-D-Ribofuranosyl)-6-Methylthymine-(15)

A solution of 14 in anhydrous pyridine (7.4 mL) was treated with acetic anhydride (1.2 mL) and stirred at room temperature for 3 hours. The solvent was evaporated under reduced pressure, and the residue was purified by silica gel column chromatography [eluent: stepwise gradient of methanol (0-5%) in methylene chloride] to afford 15.

Example 23

Preparation of 1-(5,2,3-Tri-O-Acetyl-4-C-Methyl-β-D-Ribofuranosyl)-4-Thio-6-Methylthymine-(16)

Lawesson's reagent (119 mg, 0.29 mmol) was added under argon to a solution of 15 in anhydrous 1,2-dichloroethane (11 mL) and the reaction mixture was stirred overnight under reflux. The solvent was evaporated under reduced pressure and the residue was purified by silica gel column chromatography [eluent: stepwise gradient of methanol (1-2%) in chloroform] to give 16.

Example 24

Preparation of 1-(4-C-Methyl-β-D-Ribofuranosyl)-5-Methyl-6-Methylcytosine-(17), Hydrochloride Form Compound 16 was treated with methanolic ammonia (previously saturated at −10° C.), (10 mL) at 100° C. in a stainless-steel bomb for 3 hours, then cooled to room temperature. The solvent was evaporated under reduced pressure and the residue was partitioned between methylene chloride (30 mL) and water (30 mL). The aqueous layer was washed with methylene chloride (2×30 mL), concentrated under reduced pressure. The crude material was purified by silica gel column chromatography [eluent: 20% methanol in methylene chloride] to afford 17. This compound was dissolved in EtOH 100 (1.5 mL), treated with a 2N hydrochloric acid solution (0.3 mL), and the mixture was stirred before being concentrated under reduced pressure. The procedure was repeated twice and 17 was precipitated from absolute ethanol.

Alternatively, the following nucleosides of Formula XXXXIII are prepared, using the appropriate sugar and pyrimidine bases.

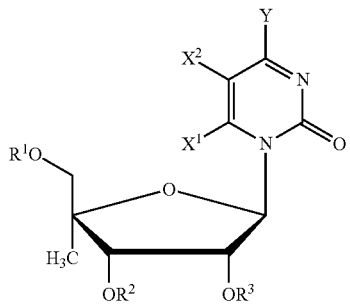

(XXXXIII)

wherein $R^1$, $R^2$, $R^3$, $X^1$, $X^2$, and Y are defined in Table 20.

Alternatively, the following nucleosides of Formula XXXXIV are prepared, using the appropriate sugar and pyrimidine or purine bases.

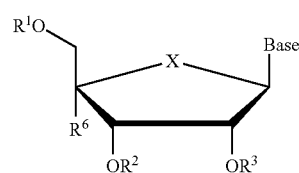

(XXXXIV)

wherein $R^1$, $R^2$, $R^3$, $R^6$, X, and Base are defined in Table 21.

Alternatively, the following nucleosides of Formula XXXXV are prepared, using the appropriate sugar and pyrimidine or purine bases.

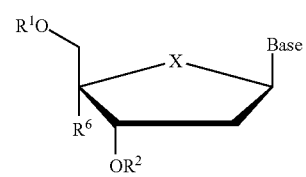

(XXXXV)

wherein $R^1$, $R^2$, $R^6$, X, and Base are defined in Table 22.

Alternatively, the following nucleosides of Formula XXXXVI are prepared, using the appropriate sugar and pyrimidine or purine bases.

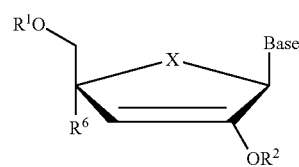

(XXXXVI)

wherein $R^1$, $R^2$, $R^6$, X, and Base are defined in Table 23

Alternatively, the following nucleosides of Formula XXXXVII are prepared, using the appropriate sugar and pyrimidine or purine bases.

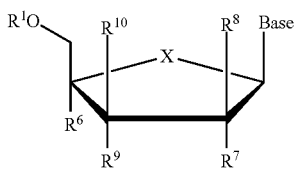

(XXXXVII)

wherein $R^1$, $R^6$, $R^7$, $R^8$, $R^9$, $R^{10}$, X, and Base are defined in Table 24.

Tables 1-24 set out examples of species within the present invention. When the amino acid appears in the table, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations. When the term acyl is used in the tables, it is meant to be a specific and independent disclosure of any of the acyl groups as defined herein, including, but not limited to, acetyl, trifluoroacetyl, methylacetyl, cyclopropylacetyl, propionyl, butyryl, hexanoyl, heptanoyl, octanoyl, neo-heptanoyl, phenylacetyl, diphenylacetyl, α-trifluoromethyl-phenylacetyl, bromoacetyl, 4-chloro-benzeneacetyl, 2-chloro-2, 2-diphenylacetyl, 2-chloro-2-phenylacetyl, trimethylacetyl, chlorodifluoroacetyl, perfluoroacetyl, fluoroacetyl, bromodifluoroacetyl, 2-thiopheneacetyl, tert-butylacetyl, trichloroacetyl, monochloro-acetyl, dichloroacetyl, methoxybenzoyl, 2-bromo-propionyl, decanoyl, n-pentadecanoyl, stearyl, 3-cyclopentyl-propionyl, 1-benzene-carboxyl, pivaloyl acetyl, 1-adamantane-carboxyl, cyclohexane-carboxyl, 2,6-pyridinedicarboxyl, cyclopropane-carboxyl, cyclobutane-carboxyl, 4-methylbenzoyl, crotonyl, 1-methyl-1H-indazole-3-carbonyl, 2-propenyl, isovaleryl, 4-phenylbenzoyl.

VIII. Biological Assays

A number of assays are available to determine the potency of test compounds against viruses. Several of these biological assays are described in the examples below.

Example 25

Anti-Flavivirus or Pestivirus Activity

Compounds can exhibit anti-flavivirus or pestivirus activity by inhibiting flavivirus or pestivirus polymerase, by inhibiting other enzymes needed in the replication cycle, or by other pathways.

Phosphorylation Assay of Nucleoside to Active Triphosphate

To determine the cellular metabolism of the compounds, HepG2 cells are obtained from the American Type Culture Collection (Rockville, Md.), and are grown in 225 cm² tissue culture flasks in minimal essential medium supplemented with non-essential amino acids, 1% penicillin-streptomycin. The medium is renewed every three days, and the cells are subcultured once a week. After detachment of the adherent monolayer with a 10 minute exposure to 30 mL of trypsin-EDTA and three consecutive washes with medium, confluent HepG2 cells are seeded at a density of 2.5×10⁶ cells per well in a 6-well plate and exposed to 10 μM of [³H] labeled active compound (500 dpm/pmol) for the specified time periods. The cells are maintained at 37° C. under a 5% $CO_2$ atmosphere. At the selected time points, the cells are washed three times with ice-cold phosphate-buffered saline (PBS). Intracellular active compound and its respective metabolites are extracted by incubating the cell pellet overnight at −20° C. with 60% methanol followed by extraction with an additional 20 μL of cold methanol for one hour in an ice bath. The extracts are then combined, dried under gentle filtered air flow and stored at −20° C. until HPLC analysis.

Bioavailability Assay in Cynomolgus Monkeys

Within 1 week prior to the study initiation, the cynomolgus monkey is surgically implanted with a chronic venous catheter and subcutaneous venous access port (VAP) to facilitate blood collection and underwent a physical examination including hematology and serum chemistry evaluations and the body weight was recorded. Each monkey (six total) receives approximately 250 μCi of ³H activity with each dose of active compound at a dose level of 10 mg/kg at a dose concentration of 5 mg/mL, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1, 2, 3, 6, 8, 12 and 24 hours post-dosage) via the chronic venous catheter and YAP or from a peripheral vessel if the chronic venous catheter procedure should not be possible. The blood and urine samples are analyzed for the maximum concentration ($C_{max}$), time when the maximum concentration is achieved ($T_{max}$), area under the curve (AUC), half life of the dosage concentration ($T_{1/2}$), clearance (CL), steady state volume and distribution ($V_{ss}$) and bioavailability (F).

Bone Marrow Toxicity Assay

Human bone marrow cells are collected from normal healthy volunteers and the mononuclear population are separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl) guanine for normal human hematopoietic progenitor cells in vitro" Antimicrobial Agents and Chemotherapy 1987; 31:452-454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human bone marrow progenitor cells" Biochemical Pharmacology 1992; 44:1921-1925. The culture assays for CFU-GM and BFU-E are performed using a bilayer soft agar or methylcellulose method. Drugs are diluted in tissue culture medium and filtered. After 14 to 18 days at 37° C. in a humidified atmosphere of 5% $CO_2$ in air, colonies of greater than 50 cells are counted using an inverted microscope. The results are presented as the percent inhibition of colony formation in the presence of drug compared to solvent control cultures.

Mitochondria Toxicity Assay

HepG2 cells are cultured in 12-well plates as described above and exposed to various concentrations of drugs as taught by Pan-Zhou X—R, Cui L, Zhou X-J, Sommadossi J-P, Darley-Usmer V M. "Differential effects of antiretroviral nucleoside analogs on mitochondrial function in HepG2 cells" Antimicrob. Agents Chemother. 2000; 44:496-503. Lactic acid levels in the culture medium after 4 day drug exposure are measured using a Boehringer lactic acid assay kit. Lactic acid levels are normalized by cell number as measured by hemocytometer count.

Cytotoxicity Assay

Cells are seeded at a rate of between 5×10³ and 5×10⁴/well into 96-well plates in growth medium overnight at 37° C. in a humidified $CO_2$ (5%) atmosphere. New growth medium containing serial dilutions of the drugs is then added. After incubation for 4 days, cultures are fixed in 50% TCA and stained with sulforhodamineB. The optical density was read at 550 nm. The cytotoxic concentration was expressed as the concentration required to reduce the cell number by 50% ($CC_{50}$).

Cell Protection Assay (CPA)

The assay is performed essentially as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" *PNAS USA* 2000, 97(14), 7981-7986. MDBK cells (ATCC) are seeded onto 96-well culture plates (4,000 cells per well) 24 hours before use. After infection with BVDV (strain NADL, ATCC) at a multiplicity of infection (MOI) of 0.02 plaque forming units (PFU) per cell, serial dilutions of test compounds are added to both infected and uninfected cells in a final concentration of 0.5% DMSO in growth medium. Each dilution is tested in quadruplicate. Cell densities and virus inocula are adjusted to ensure continuous cell growth throughout the experiment and to achieve more than 90% virus-induced cell destruction in the untreated controls after four days post-infection. After four days, plates are fixed with 50% TCA and stained with sulforhodamine B. The optical density of the wells is read in a microplate reader at 550 nm. The 50% effective concentration ($EC_{50}$) values are defined as the compound concentration that achieved 50% reduction of cytopathic effect of the virus.

Plaque Reduction Assay

For each compound the effective concentration is determined in duplicate 24-well plates by plaque reduction assays. Cell monolayers are infected with 100 PFU/well of virus. Then, serial dilutions of test compounds in MEM supplemented with 2% inactivated serum and 0.75% of methyl cellulose are added to the monolayers. Cultures are further incubated at 37° C. for 3 days, then fixed with 50% ethanol and 0.8% Crystal Violet, washed and air-dried. Then plaques are counted to determine the concentration to obtain 90% virus suppression.

Yield Reduction Assay

For each compound the concentration to obtain a 6-log reduction in viral load is determined in duplicate 24-well plates by yield reduction assays. The assay is performed as described by Baginski, S. G.; Pevcar, D. C.; Seipel, M.; Sun, S. C. C.; Benetatos, C. A.; Chunduru, S. K.; Rice, C. M. and M. S. Collett "Mechanism of action of a pestivirus antiviral compound" *PNAS USA* 2000, 97(14), 7981-7986, with minor modifications. Briefly, MDBK cells are seeded onto 24-well plates ($2 \times 10^5$ cells per well) 24 hours before infection with BVDV (NADL strain) at a multiplicity of infection (MOI) of 0.1 PFU per cell. Serial dilutions of test compounds are added to cells in a final concentration of 0.5% DMSO in growth medium. Each dilution is tested in triplicate. After three days, cell cultures (cell monolayers and supernatants) are lysed by three freeze-thaw cycles, and virus yield is quantified by plaque assay. Briefly, MDBK cells are seeded onto 6-well plates ($5 \times 10^5$ cells per well) 24 h before use. Cells are inoculated with 0.2 mL of test lysates for 1 hour, washed and overlaid with 0.5% agarose in growth medium. After 3 days, cell monolayers are fixed with 3.5% formaldehyde and stained with 1% crystal violet (w/v in 50% ethanol) to visualize plaques. The plaques are counted to determine the concentration to obtain a 6-log reduction in viral load.

Example 26

In Vitro Anti-Viral Activity

In vitro anti-viral activity was tested in the following cell lines: MT-4 for HIV; Vero 76, African green monkey kidney cells for SARS; BHK for Bovine Viral Diarrhea Virus; Sb-1 for poliovirus Sabin type-1; CVB-2, CVB-3, CVB-4, and CVA-9 for Coxsackieviruses B-2, B-3, B-4 and A-9; and REO-1 for double-stranded RNA viruses. Note: BVDV=bovine viral diarrhea virus; YFV=yellow fever virus; DENV=dengue virus; WNV=West Nile virus; CVB-2=Coxsackie B-2 virus; Sb-1=Sabin type 1 poliomyelitis virus; and REO=double-stranded RNA Reovirus.

$CC_{50}$ and $EC_{50}$ Test Results for β-D-2'-C-methyl-7-methyl-6-phenyl-3,3a,5,8a-tetrahydro-1,3,4,5,7a-penta-aza-s-indacen-8-one (Compound F)

| Compound | $CC_{50}$ MT-4 | $CC_{50}$ Vero76 | $CC_{50}$ BHK | $EC_{50}$ Sb-1 | $EC_{50}$ CVB-2 | $EC_{50}$ CVB-3 | $EC_{50}$ CVB-4 | $EC_{50}$ CVA-9 | $EC_{50}$ REO-1 |
|---|---|---|---|---|---|---|---|---|---|
| F | >100 | >100 | >100 | 43 | 37 | 49 | 39 | 60 | 2 |

$CC_{50}$ Test Results for β-D-2'-C-methyl-7-methyl-6-phenyl-3,3a,5,8a-tetrahydro-1,3,4,5,7a-penta-aza-s-indacen-8-one (Compound F)

| Compound | $CC_{50}$ | BVDV | YFV | DENV2 | WNV | CVB-2 | Sb-1 | REO |
|---|---|---|---|---|---|---|---|---|
| F | >100 | 10 | 2.5 | 1.3 | 1 | 37 | 43 | 2 |

This invention has been described with reference to its preferred embodiments. Variations and modifications of the invention, will be obvious to those skilled in the art from the foregoing detailed description of the invention.

What is claimed is:

1. A compound of the Formula (XIII):

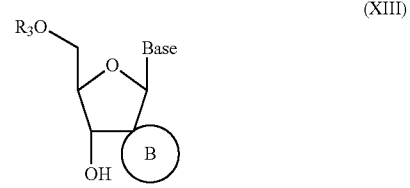

(XIII)

or a pharmaceutically acceptable salt thereof, wherein:
$R_3$ is selected from the group consisting of H; mono-, di-, and tri-phosphate or a stabilized phosphate prodrug; acyl; a sulfonate ester; optionally substituted alkyl sulfonyl; optionally substituted arylsulfonyl; a lipid; an amino acid; a carbohydrate; a peptide; cholesterol; and a pharmaceutically acceptable leaving group which when administered in vivo is capable of providing a compound wherein $R_3$ is independently H, or mono-, di- or triphosphate;

B is an optionally substituted 3-7 membered heterocyclic ring consisting of C, O and/or S atoms;

Base is selected from the group consisting of:

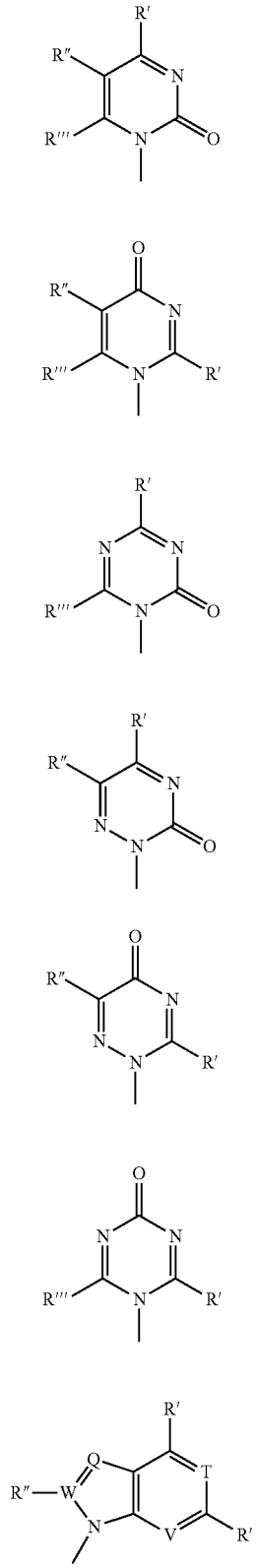

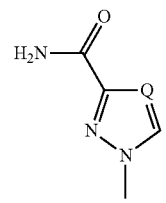

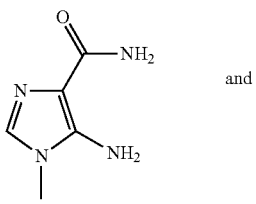

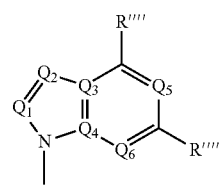

wherein
- each R', R'', R''' and R'''' are independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$ and $(CH_2)_mCONH_2$;
- m is 0 or 1;
- W is C—R'' or N;
- T and V independently are CH or N;
- Q is CH, —CCl, —CBr, —CF, —CI, —CCN, —C—COOH, —C—$CONH_2$, or N;
- $Q_1$ and $Q_2$ independently are N or C—R;
- R is H, alkyl, or acyl; and
- $Q_3$, $Q_4$, $Q_5$ and $Q_6$ independently are N or CH.

2. A pharmaceutical composition comprising a compound of claim 1, and a pharmaceutically acceptable carrier.

3. A method for the treatment of a host infected with a hepatitis C virus, comprising administering an effective treatment amount of a compound as claimed in claim 1, or a pharmaceutically acceptable salt thereof.

4. The method of claim 3, wherein the compound or pharmaceutically acceptable salt thereof is administered in combination or alternation with a second anti-viral agent.

5. The method of claim 4, wherein the second anti-viral agent is selected from the group consisting of an interferon, a ribavirin, an interleukin, a NS3 protease inhibitor, a cysteine protease inhibitor, a phenan-threnequinone, a thiazolidine derivative, a thiazolidine, a benzanilide, a phenan-threnequinone, a helicase inhibitor, a polymerase inhibitor, a nucleotide analogue, a gliotoxin, a cerulenin, an antisense phosphorothioate oligodeoxynucleotide, an inhibitor of IRES-dependent translation, and a ribozyme.

6. The method of claim 5, wherein the second anti-viral agent is an interferon.

7. The method of claim 6, wherein the second anti-viral agent is selected from the group consisting of pegylated interferon alpha 2a, interferon alphacon-1, natural interferon, albuferon, interferon beta-1a, omega interferon, interferon alpha, interferon gamma, interferon tau, interferon delta and interferon gamma-1b.

8. The method of claim 3, wherein the compound or pharmaceutically acceptable salt thereof is in the form of a dosage unit.

9. The method of claim 8, wherein the dosage unit contains 50 to 1000 mg or 0.1 to 50 mg of the compound.

10. The method of claim 8, wherein the dosage unit is a tablet or capsule.

11. The method of claim 3, wherein the host is a human.

* * * * *